(12) United States Patent
Matsumoto

(10) Patent No.: US 9,173,928 B2
(45) Date of Patent: Nov. 3, 2015

(54) DNA VACCINE FOR ALZHEIMER'S DISEASE

(71) Applicant: Yoh Matsumoto, Tokyo (JP)

(72) Inventor: Yoh Matsumoto, Tokyo (JP)

(73) Assignee: Yoh Matsumoto, Saitama (JP)

( * ) Notice: Subject to any disclaimer, the term of this patent is extended or adjusted under 35 U.S.C. 154(b) by 0 days.

(21) Appl. No.: 13/744,223

(22) Filed: Jan. 17, 2013

(65) Prior Publication Data

US 2013/0122026 A1 May 16, 2013

Related U.S. Application Data

(63) Continuation-in-part of application No. 13/257,713, filed as application No. PCT/JP2010/055308 on Mar. 26, 2010, now abandoned.

(30) Foreign Application Priority Data

Mar. 26, 2009 (JP) ................. 2009-075832

(51) Int. Cl.
*A61K 39/00* (2006.01)
*C07K 14/47* (2006.01)
*C07K 16/16* (2006.01)

(52) U.S. Cl.
CPC ......... *A61K 39/0007* (2013.01); *C07K 14/4711* (2013.01); *C07K 16/16* (2013.01); *A61K 2039/53* (2013.01); *A61K 2039/55522* (2013.01); *A61K 2039/55527* (2013.01); *A61K 2039/6056* (2013.01)

(58) Field of Classification Search
None
See application file for complete search history.

(56) References Cited

U.S. PATENT DOCUMENTS 7,030,098 B2 * 4/2006 Steinman et al. ........... 514/44 R
2012/0014987 A1 1/2012 Matsumoto

FOREIGN PATENT DOCUMENTS

| WO | WO 03045316 A2 * | 6/2003 |
| WO | WO 2005/014041 A2 | 2/2005 |
| WO | WO 2008/097927 A2 | 8/2008 |
| WO | WO 2009/029272 A2 | 3/2009 |
| WO | WO 2010/110408 A1 | 9/2010 |

OTHER PUBLICATIONS

Almeida, O.P. Can we prevent Alzheimer's disease? Revista Brasileira de Psiquiatria, vol. 27, No. 4, pp. 264-265, Dec. 2005.*
Szekely et al. Prevention of Alheimer's disease. International Review of Psychiatry, vol. 19, No. 6, pp. 693-706, Dec. 2007.*
Lewin, B. Glossary entry for "Gene." Genes V. Oxford University Press, New York, 1995.*
Frazer et al. Reduced pathology and improved behavioral performance in Alxheimer's disease mice vaccinated with HSV amplicons expressing amyloid-beta and interleukin-4. Molecular Therapy, vol. 16, No. 5, pp. 845-853, May 2008.*
Janus et al. Abeta peptide immunization reduces behavioural impairment and plaques in a model of Alzheimer's disease. Nature, vol. 408, pp. 979-982, Dec. 2000.*
de Felipe. Use of the 2A seqeunce from foot-and-mouth disease virus in the generation of retroviral vectors for gene therapy. Gene Therapy, vol. 6, pp. 198-208, 1999.*
Ghiso et al., "Genetic Alterations of the BR12 gene: Familial British and Danish Dementias," Brain Pathol. (2006), vol. 16, pp. 71-79.
Ghochikyan et al., "Generation and characterization of the humoral immune response to DNA immunization with a chimeric beta-amyloid-interleukin-4 minigene," Eur. J. Immunol. (2003), vol. 33, pp. 3232-3241.
Masters, C. L. and K. Beyreuther, "Alzheimer's centennial legacy: prospects for rational therapeutic intervention targeting the Ab amyloid pathway," Brain (2006), vol. 129, pp. 2823-2339.
Okura et al., "Nonviral Ab DNA vaccine therapy against Alzheimer's disease: Long-term effects and safety," PNAS (Jun. 20, 2006), vol. 103, No. 25, pp. 9619-9624.
Okura et al., "Nonviral DNA Vaccination Augments Microglial Phagocytosis of B-Amyloid Deposits as a Major Clearance Pathway in an Alzheimer Disease Mouse Model," J. Neuropathol. Exp. Neurol. (Nov. 2008), vol. 67, No. 11, pp. 1063-1071.
Okura Y. and Y. Matsumoto, "Development of Anti-Ab Vaccination as a Promising Therapy for Alzheimer's Disease," Drug News Perspect (Jul./Aug. 2007), vol. 20, No. 6, pp. 379-386.
Okura, Y. and Y. Matsumoto, "DNA Vaccine Therapy for Alzheimer's Disease: Present Status and Future Direction," Rejuvenation Research (2008) vol. 11, No. 2, pp. 301-308.
Okura, Y. and Y. Matsumoto, "Novel Vaccine Therapy for Alzheimer's Disease—Recent Progress and Our Approach," Brain and Nerve (2008), vol. 60, No. 8, pp. 931-940.
Saido et al., "Amino- and carboxyl-terminal heterogeneity of B-amyloid peptides deposited in human brain," Neuroscience Letters (1996), vol. 215, pp. 173-176.
Schenk et al., "Immunization with amyloid-b attenuates Alzheimer-disease-like pathology in the PDAPP mouse," Nature (Jul. 8, 1999), vol. 400, pp. 173-177.
Schlenzig et al., "Pyroglutamate Formation Influences Solubility and Amyloidogenicity of Amyloid Peptides," Biochemistry (2009), vol. 48, pp. 7072-7078.
Tokita et al., "Nonviral Abeta DNA vaccine therapy against Alzheimer's disease: Effects and safety in rhesus monkey," Proceedings of the Japanese Society for Immunology, 2008, vol. 38, p. 146 (2-D-W23-12-P) (partial English translation).

(Continued)

*Primary Examiner* — Jennifer Dunston
(74) *Attorney, Agent, or Firm* — Birch, Stewart, Kolasch & Birch, LLP

(57) ABSTRACT

The invention provides a recombinant vector, which includes repeats of Amyloid β 1-42 (Aβ1-42) gene, an immunoglobulin Fc gene, a spacer sequence and interleukin-4 gene in this order, the repeats of the Aβ1-42 gene contain spacer sequences between the individual Aβ1-42 genes. The invention also provides a DNA vaccine for Alzheimer's disease, which includes the recombinant vector.

17 Claims, 34 Drawing Sheets
(19 of 34 Drawing Sheet(s) Filed in Color)

(56) References Cited

OTHER PUBLICATIONS

Zou et al., "Vaccination of Alzheimer's model mice with adenovirus vector containing quadrivalent foldable Ab1-15 reduces AB burden and behavioral impairment without Ab-specific T cell repsonse," Journal of Neurological Sciences (2008), vol. 272, pp. 87-98.

Extended European Search Report issued Nov. 2, 2012, in European Patent Application No. 10756204.3.

Matsumoto, V. and K. Kohyama, "Development of a new DNA vaccine for Alzheimer disease targeting Abeta species and amyloiditogenic peptides in the brain," Brain Pathology (2010), vol. 2 (Suppl. 1), 2010, Po3-1, p. 16.

Movsesyan et al., "Reducing AD-Like Pathology in 3xTg-AD Mouse MOdel by DNA Epitope Vaccine—A Novel Immunotherapeutic Strategy," PLoS One (May 2008), vol. 3, No. 5, e2124, pp. 1-13.

Okura, Y. and Y. Matsumoto, "Recent advance in immunotherapies for Alzheimer Disease," Human Vaccines (Jun. 2009), vol. 5, No. 6, pp. 373-380.

* cited by examiner

Figure 7    Ig leader-(hu Aβ$_{1-42}$)x4-hu IgFc-spacer-hu IL-4 (YM3711)

Figure 8   Ig leader-(hu Aβ$_{1-42}$)x4-mo IgFc-spacer-mo IL-4

Figure 25
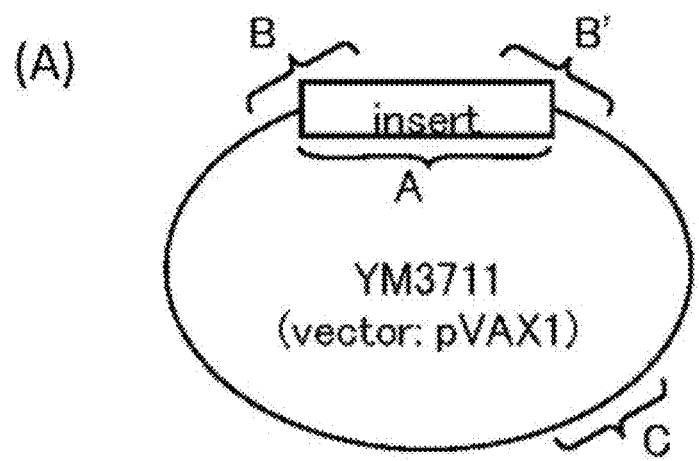
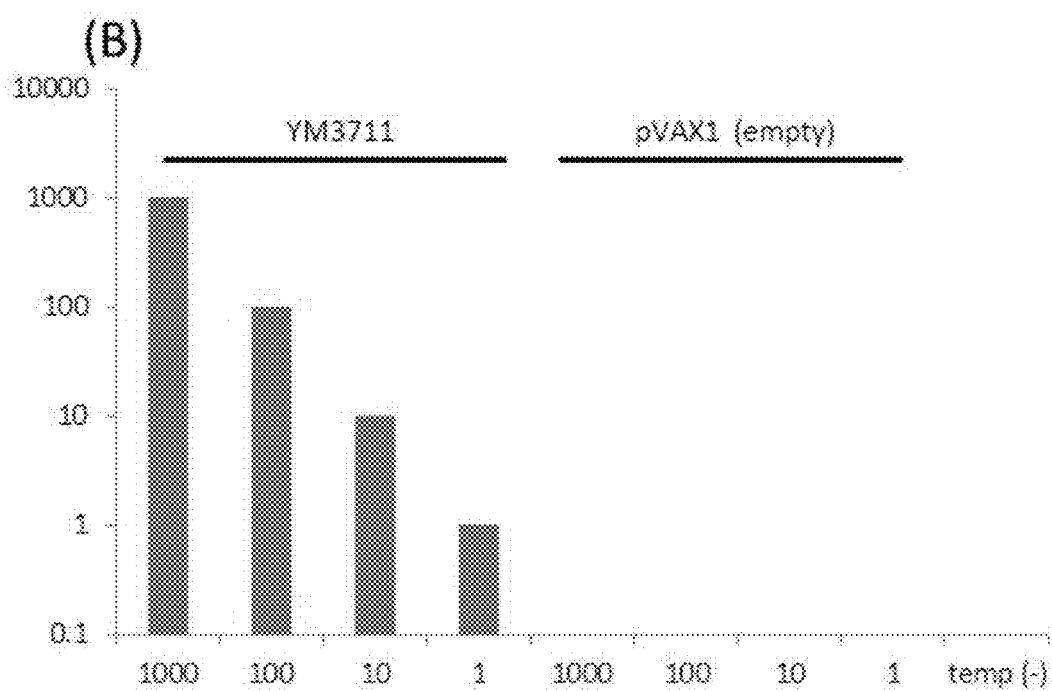

Figure 29
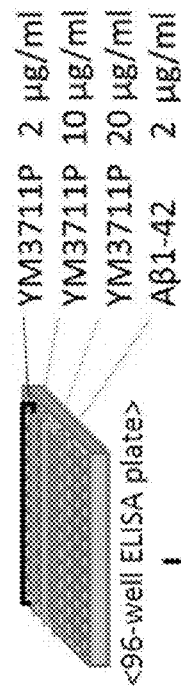
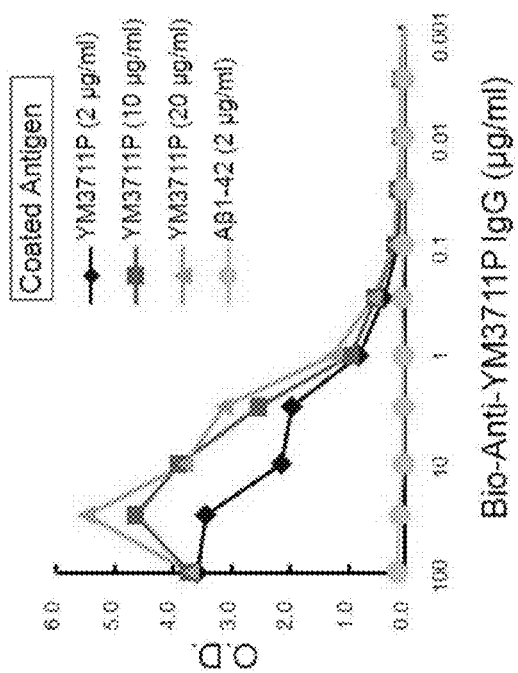

Toxicology study of YM3711 in *Macaca fascicularis* monkeys (B)

Figure 34:
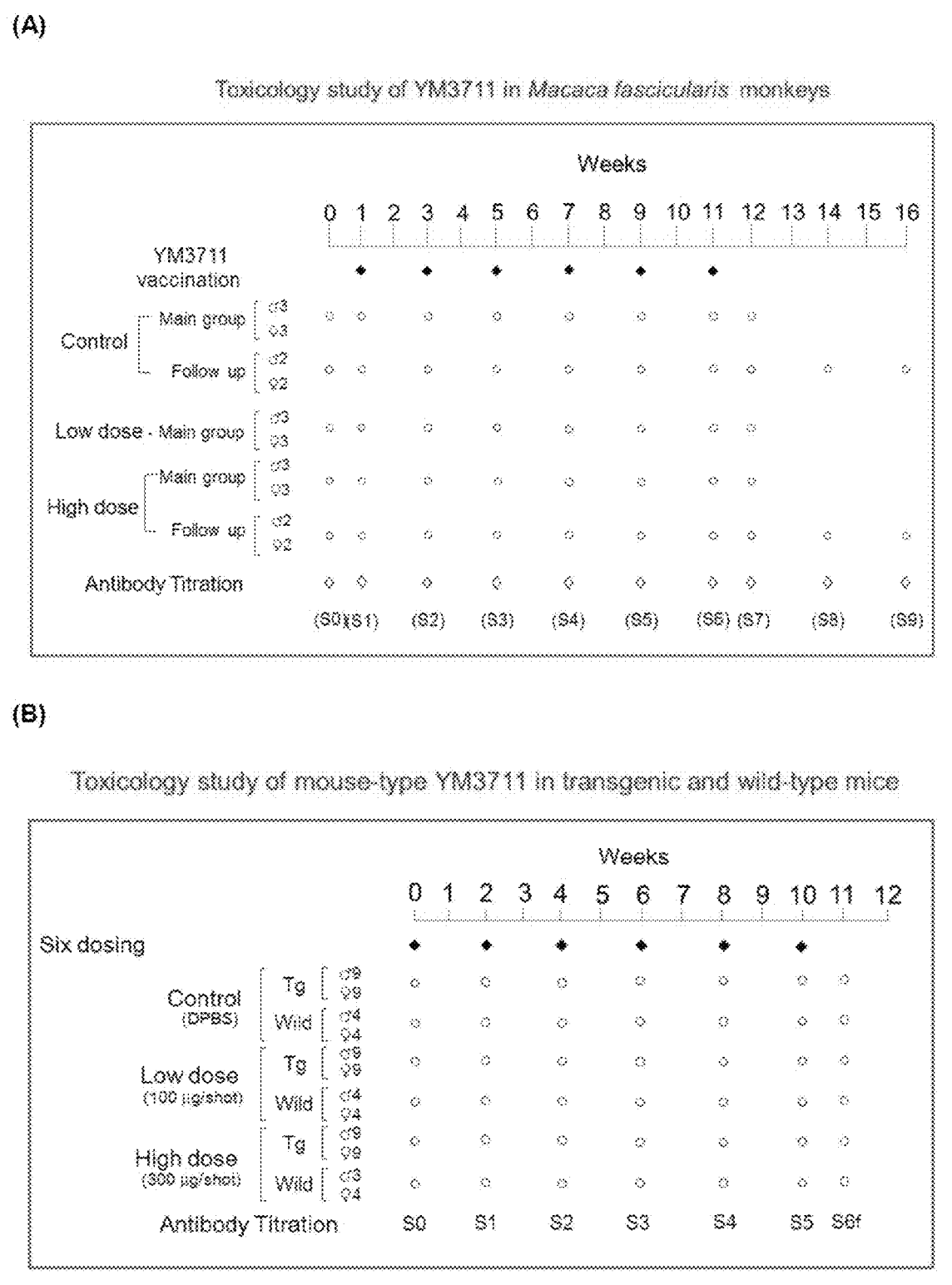

Toxicology study of mouse-type YM3711 in transgenic and wild-type mice

SEQUENCE LISTING

<160> NUMBER OF SEQ ID NOS: 35

<210> SEQ ID NO 1
<211> LENGTH: 129
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(129)

<400> SEQUENCE: 1

```
gat gca gaa ttc cga cat gac tca gga tat gaa gtt cat cat caa aaa     48
Asp Ala Glu Phe Arg His Asp Ser Gly Tyr Glu Val His His Gln Lys
1               5                   10                  15 ttg gtg ttc ttt gca gaa gat gtg ggt tca aac aaa ggt gca atc att     96
Leu Val Phe Phe Ala Glu Asp Val Gly Ser Asn Lys Gly Ala Ile Ile
            20                  25                  30 gga ctc atg gtg ggc ggt gtt gtc ata gcg aca                        129
Gly Leu Met Val Gly Gly Val Val Ile Ala Thr
        35                  40
```

<210> SEQ ID NO 2
<211> LENGTH: 43
<212> TYPE: PRT
<213> ORGANISM: Artificial
<220> FEATURE:
<223> OTHER INFORMATION: Synthetic Construct

<400> SEQUENCE: 2

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```

<210> SEQ ID NO 3
<211> LENGTH: 60
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(60)

<400> SEQUENCE: 3

```
gat gca gaa ttc cga cat gac tca gga tat gaa gtt cat cat caa aaa     48
Asp Ala Glu Phe Arg His Asp Ser Gly Tyr Glu Val His His Gln Lys
1               5                   10                  15 ttg gtg ttc ttt                                                     60
Leu Val Phe Phe
            20
```

<210> SEQ ID NO 4
<211> LENGTH: 20
<212> TYPE: PRT
<213> ORGANISM: Artificial

<220> FEATURE:
<223> OTHER INFORMATION: Synthetic Construct

<400> SEQUENCE: 4

```
Asp Ala Glu Phe Arg His Asp Ser Gly Tyr Glu Val His His Gln Lys
1               5                   10                  15

Leu Val Phe Phe
            20
```

<210> SEQ ID NO 5
<211> LENGTH: 120
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(120)

<400> SEQUENCE: 5

```
gat gca gaa ttc cga cat gac tca gga tat gaa gtt cat cat caa aaa      48
Asp Ala Glu Phe Arg His Asp Ser Gly Tyr Glu Val His His Gln Lys
1               5                   10                  15 ttg gtg ttc ttt gca gaa gat gtg ggt tca aac aaa ggt gca atc att      96
Leu Val Phe Phe Ala Glu Asp Val Gly Ser Asn Lys Gly Ala Ile Ile
            20                  25                  30 gga ctc atg gtg ggc ggt gtt gtc                                     120
Gly Leu Met Val Gly Gly Val Val
        35                  40
```

<210> SEQ ID NO 6
<211> LENGTH: 40
<212> TYPE: PRT
<213> ORGANISM: Artificial
<220> FEATURE:
<223> OTHER INFORMATION: Synthetic Construct

<400> SEQUENCE: 6

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40
```

<210> SEQ ID NO 7
<211> LENGTH: 126
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(126)

<400> SEQUENCE: 7

```
gat gca gaa ttc cga cat gac tca gga tat gaa gtt cat cat caa aaa      48
Asp Ala Glu Phe Arg His Asp Ser Gly Tyr Glu Val His His Gln Lys
1               5                   10                  15 ttg gtg ttc ttt gca gaa gat gtg ggt tca aac aaa ggt gca atc att      96
Leu Val Phe Phe Ala Glu Asp Val Gly Ser Asn Lys Gly Ala Ile Ile
            20                  25                  30 gga ctc atg gtg ggc ggt gtt gtc ata gcg                             126
Gly Leu Met Val Gly Gly Val Val Ile Ala
        35                  40
```

```
<210> SEQ ID NO 8
<211> LENGTH: 42
<212> TYPE: PRT
<213> ORGANISM: Artificial
<220> FEATURE:
<223> OTHER INFORMATION: Synthetic Construct

<400> SEQUENCE: 8

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 9
<211> LENGTH: 129
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(129)

<400> SEQUENCE: 9 gat gca gaa ttc gga cat gat tca gga ttt gaa gtc cgc cat caa aaa        48
Asp Ala Glu Phe Gly His Asp Ser Gly Phe Glu Val Arg His Gln Lys
1               5                   10                  15 ctg gtg ttc ttt gct gaa gat gtg ggt tcg aac aaa ggc gcc atc atc        96
Leu Val Phe Phe Ala Glu Asp Val Gly Ser Asn Lys Gly Ala Ile Ile
                20                  25                  30 gga ctc atg gtg ggc ggc gtt gtc ata gca acc                           129
Gly Leu Met Val Gly Gly Val Val Ile Ala Thr
            35                  40

<210> SEQ ID NO 10
<211> LENGTH: 43
<212> TYPE: PRT
<213> ORGANISM: Artificial
<220> FEATURE:
<223> OTHER INFORMATION: Synthetic Construct

<400> SEQUENCE: 10

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
            35                  40

<210> SEQ ID NO 11
<211> LENGTH: 60
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(60)
```

```
<400> SEQUENCE: 11 gat gca gaa ttc gga cat gat tca gga ttt gaa gtc cgc cat caa aaa      48
Asp Ala Glu Phe Gly His Asp Ser Gly Phe Glu Val Arg His Gln Lys
1               5                   10                  15 ctg gtg ttc ttt                                                      60
Leu Val Phe Phe
            20

<210> SEQ ID NO 12
<211> LENGTH: 20
<212> TYPE: PRT
<213> ORGANISM: Artificial
<220> FEATURE:
<223> OTHER INFORMATION: Synthetic Construct

<400> SEQUENCE: 12

Asp Ala Glu Phe Gly His Asp Ser Gly Phe Glu Val Arg His Gln Lys
1               5                   10                  15

Leu Val Phe Phe
            20

<210> SEQ ID NO 13
<211> LENGTH: 120
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(120)

<400> SEQUENCE: 13 gat gca gaa ttc gga cat gat tca gga ttt gaa gtc cgc cat caa aaa      48
Asp Ala Glu Phe Gly His Asp Ser Gly Phe Glu Val Arg His Gln Lys
1               5                   10                  15 ctg gtg ttc ttt gct gaa gat gtg ggt tcg aac aaa ggc gcc atc atc      96
Leu Val Phe Phe Ala Glu Asp Val Gly Ser Asn Lys Gly Ala Ile Ile
            20                  25                  30 gga ctc atg gtg ggc ggc gtt gtc                                     120
Gly Leu Met Val Gly Gly Val Val
        35                  40

<210> SEQ ID NO 14
<211> LENGTH: 40
<212> TYPE: PRT
<213> ORGANISM: Artificial
<220> FEATURE:
<223> OTHER INFORMATION: Synthetic Construct

<400> SEQUENCE: 14

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 15
<211> LENGTH: 126
<212> TYPE: DNA
<213> ORGANISM: Artificial
<220> FEATURE:
<223> OTHER INFORMATION: synthetic DNA
```

```
<220> FEATURE:
<221> NAME/KEY: CDS
<222> LOCATION: (1)..(126)

<400> SEQUENCE: 15 gat gca gaa ttc gga cat gat tca gga ttt gaa gtc cgc cat caa aaa     48
Asp Ala Glu Phe Gly His Asp Ser Gly Phe Glu Val Arg His Gln Lys
1               5                   10                  15 ctg gtg ttc ttt gct gaa gat gtg ggt tcg aac aaa ggc gcc atc atc     96
Leu Val Phe Phe Ala Glu Asp Val Gly Ser Asn Lys Gly Ala Ile Ile
            20                  25                  30 gga ctc atg gtg ggc ggc gtt gtc ata gca                            126
Gly Leu Met Val Gly Gly Val Val Ile Ala
        35                  40

<210> SEQ ID NO 16
<211> LENGTH: 42
<212> TYPE: PRT
<213> ORGANISM: Artificial
<220> FEATURE:
<223> OTHER INFORMATION: Synthetic Construct

<400> SEQUENCE: 16

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 17
<211> LENGTH: 462
<212> TYPE: DNA
<213> ORGANISM: Homo sapiens

<400> SEQUENCE: 17
atgggtctca cctcccaact gcttcccct ctgttcttcc tgctagcatg tgccggcaac      60
tttgtccacg acacaagtg cgatatcacc ttacaggaga tcatcaaaac tttgaacagc     120
ctcacagagc agaagactct gtgcaccgag ttgaccgtaa cagacatctt tgctgcctcc    180
aagaacacaa ctgagaagga aaccttctgc agggctgcga ctgtgctccg gcagttctac    240
agccaccatg agaaggacac tcgctgcctg ggtgcgactg cacagcagtt ccacaggcac    300
aagcagctga tccgattcct gaaacggctc gacaggaacc tctggggcct ggcgggcttg    360
aattcctgtc ctgtgaagga agccaaccag agtacgttgg aaaacttctt ggaaaggcta    420
aagacgatca tgagagagaa atattcaaag tgttcgagct ga                      462

<210> SEQ ID NO 18
<211> LENGTH: 423
<212> TYPE: DNA
<213> ORGANISM: Mus musculus

<400> SEQUENCE: 18
atgggtctca cccccagct agttgtcatc ctgctcttct ttctcgaatg taccaggagc      60
catatccacg gatgcgacaa aaatcacttg agagagatca tcggcatttt gaacgaggtc    120
acaggagaag ggacgccatg cacggagatg gatgtgccaa cgtcctcac agcaacgaag    180 aacaccacag agagtgagct cgtctgtagg gcttccaagg tgcttcgcat atttatttta    240
aaacatggga aaactccatg cttgaagaag aactctagtg ttctcatgga gctgcagaga    300
```

```
ctctttcggg cttttcgatg cctggattca tcgataagct gcaccatgaa tgagtccaag    360
tccacatcac tgaaagactt cctggaaagc ctaaagagca tcatgcaaat ggattactcg    420
tag                                                                  423
```

```
<210> SEQ ID NO 19
<211> LENGTH: 1665
<212> TYPE: DNA
<213> ORGANISM: Homo sapiens

<400> SEQUENCE: 19
atgaccgcgc cgggcgccgc cgggcgctgc cctcccacga catggctggg ctccctgctg     60
ttgttggtct gtctcctggc gagcaggagt atcaccgagg aggtgtcgga gtactgtagc    120
cacatgattg ggagtggaca cctgcagtct ctgcagcggc tgattgacag tcagatggag    180
acctcgtgcc aaattacatt tgagtttgta gaccaggaac agttgaaaga tccagtgtgc    240
taccttaaga aggcatttct cctggtacaa gacataatgg aggacaccat gcgcttcaga    300
gataacaccc ccaatgccat cgccattgtg cagctgcagg aactctcttt gaggctgaag    360
agctgcttca ccaaggatta tgaagagcat gacaaggcct gcgtccgaac tttctatgag    420
acacctctcc agttgctgga aaggtcaag aatgtcttta tgaaacaaa gaatctcctt    480 gacaaggact ggaatatttt cagcaagaac tgcaacaaca gctttgctga atgctccagc    540
caagatgtgg tgaccaagcc tgattgcaac tgcctgtacc caaagccat ccctagcagt    600 gacccggcct ctgtctcccc tcatcagccc ctcgcccct ccatggcccc tgtggctggc    660
ttgacctggg aggactctga gggaactgag ggcagctccc tcttgcctgg tgagcagccc    720
ctgcacacag tggatccagg cagtgccaag cagcggccac caggagcac ctgccagagc    780 tttgagccgc cagagacccc agttgtcaag gacagcacca tcggtggctc accacagcct    840 cgccccctctg tcgggccctt caaccccggg atggaggata ttcttgactc tgcaatgggc    900
actaattggg tcccagaaga agcctctgga gaggccagtg agattcccgt accccaaggg    960
acagagcttt cccccctccag gccaggaggg gggcagcatgc agacagagcc cgccagaccc   1020
agcaacttcc tctcagcatc ttctccactc cctgcatcag caaagggcca acagccggca   1080
gatgtaactg gtaccgcctt gcccagggtg ggccccgtga ggcccactgg ccaggactgg   1140
aatcacaccc cccagaagac agaccatcca tctgccctgc tcagagaccc cccggagcca   1200
ggctctccca ggatctcatc actgcgcccc cagggcctca gcaaccctc caccctctct   1260 gctcagccac agctttccag aagccactcc tcgggcagcg tgctgcccct tggggagctg   1320
gagggcagga ggagcaccag ggatcggagg agcccgcag agccagaagg aggaccagca   1380
agtgaagggg cagccaggcc cctgccccgt tttaactccg ttcctttgac tgacacaggc   1440
catgagaggc agtccgaggg atcctccagc ccgcagctcc aggagtctgt cttccacctg   1500
ctggtgccca gtgtcatcct ggtcttgctg gccgtcggag gcctcttgtt ctacaggtgg   1560
aggcggcgga gccatcaaga gcctcagaga gcggattctc ccttggagca accagagggc   1620
agccccctga ctcaggatga cagacaggtg gaactgccag tgtag                   1665
```

```
<210> SEQ ID NO 20
<211> LENGTH: 1659
<212> TYPE: DNA
<213> ORGANISM: Mus musculus
```

<400> SEQUENCE: 20

```
atgaccgcgc ggggcgccgc ggggcgctgc ccttcttcga catggctggg ctcccggctg      60
ctgctggtct gtctcctcat gagcaggagt attgccaagg aggtgtcaga acactgtagc     120
cacatgattg ggaatggaca cctgaaggtc ctgcagcagt tgatcgacag tcaaatggag     180
acttcatgcc agattgcctt tgaatttgta gaccaggaac agctggatga tcctgtttgc     240
tacctaaaga aggccttttt tctggtacaa gacataatag atgagaccat gcgctttaaa     300
gacaacaccc ccaatgctaa cgccaccgag aggctccagg aactctccaa taacctgaac     360
agctgcttca ccaaggacta tgaggagcag aacaaggcct gtgtccgaac tttccatgag     420
actcctctcc agctgctgga agatcaaga acttcttta atgaaacaaa gaatctcctt     480
gaaaaggact ggaacatttt taccaagaac tgcaacaaca gctttgctaa gtgctctagc     540
cgagatgtgg tgaccaagcc tgattgcaac tgcctgtacc ctaaagccac ccctagcagt     600
gacccggcct ctgcctcccc tcaccagccc ccgcccccct ccatggcccc tctggctggc     660
ttggcttggg atgattctca gaggacagag ggcagctccc tcttgcccag tgagcttccc     720
cttcgcatag aggacccagg cagtgccaag cagcgaccac caggagtac ctgccagacc     780
ctcgagtcaa cagagcaacc aaaccatggg acagactca ctgaggactc acaacctcat     840
ccttctgcgg gggggcccgt ccctggggtg aagacattc ttgaatcttc actgggcact     900
aactgggtcc tagaagaagc ttctggagag gctagtgagg gattttttgac ccaggaagca     960
aagtttttccc cctccacgcc tgtaggggc agcatccagg cagagactga cagacccagg    1020
gccctctcag catctccatt ccctaaatca acagaggacc aaaagccagt ggatataaca    1080
gacaggccgt tgacagaggt gaaccctatg agacccattg ccagacaca gaataatact    1140
cctgagaaga ctgatggtac atccacgctg cgtgaagacc accaggagcc aggctctccc    1200
catattgcga caccgaatcc ccaacgagtc agcaactcag ccaccccgt tgctcagtta    1260
ctgcttccca aaagccactc ttggggcatt gtgctgcccc ttggggagct tgagggcaag    1320
agaagtacca gggatcgaag gagccccgca gagctggaag gaggatcagc aagtgagggg    1380
gcagccaggc ctgtggcccg tttttaattcc attcctttga ctgacacagg ccatgtggag    1440
cagcatgagg gatcctctga cccccagatc cctgagtctg tcttccacct gctggtgccg    1500
ggcatcatcc tagtcttgct gactgttggg ggcctcctgt tctacaagtg aagtggagg    1560
agccatcgag accctcagac attggattct tctgtggggc gaccagagga cagctccctg    1620
acccaggatg aggacagaca ggtggaactg ccagtatag                            1659
```

<210> SEQ ID NO 21
<211> LENGTH: 693
<212> TYPE: DNA
<213> ORGANISM: Artificial
<220> FEATURE:
<223> OTHER INFORMATION: synthetic DNA

<400> SEQUENCE: 21

```
gccaccatgg agacagacac actcctgcta tgggtactgc tgctctgggt tccaggttcc      60
actggtgacg cggccctcga ggatgcagaa ttccgacatg actcaggata tgaagttcat     120
catcaaaaat tggtgttcct tgcagaagat gtgggttcaa acaaggtgc aatcattgga     180
ctcatggtgg gcggtgttgt catagcgggt acctcttctg gtggtggtgg tatgggtctc     240
acctcccaac tgcttccccc tctgttcttc ctgctagcat gtgccggcaa cttttgtccac     300
ggacacaagt gcgatatcac cttacaggag atcatcaaaa ctttgaacag cctcacagag     360
```

| | |
|---|---|
| cagaagactc tgtgcaccga gttgaccgta acagacatct tgctgcctc caagaacaca | 420 |
| actgagaagg aaaccttctg cagggctgcg actgtgctcc ggcagttcta cagccaccat | 480 |
| gagaaggaca ctcgctgcct gggtgcgact gcacagcagt tccacaggca aagcagctg | 540 |
| atccgattcc tgaaacggct cgacaggaac ctctggggcc tggcgggctt gaattcctgt | 600 |
| cctgtgaagg aagccaacca gagtacgttg aaaacttct tggaaaggct aaagacgatc | 660 |
| atgagagaga aatattcaaa gtgttcgagc tga | 693 |

<210> SEQ ID NO 22
<211> LENGTH: 654
<212> TYPE: DNA
<213> ORGANISM: Artificial
<220> FEATURE:
<223> OTHER INFORMATION: synthetic DNA

<400> SEQUENCE: 22

| | |
|---|---|
| gccaccatgg agacagacac actcctgcta tgggtactgc tgctctgggt tccaggttcc | 60 |
| actggtgacg cggccctcga ggatgcagaa ttccgacatg actcaggata tgaagttcat | 120 |
| catcaaaaat tggtgttctt tgcagaagat gtgggttcaa acaaaggtgc aatcattgga | 180 |
| ctcatggtgg gcggtgttgt catagcgggt acctcttctg gtggtggtgg tatgggtctc | 240 |
| aaccccagc tagttgtcat cctgctcttc tttctcgaat gtaccaggag ccatatccac | 300 |
| ggatgcgaca aaaatcactt gagagagatc atcggcattt tgaacgaggt cacaggagaa | 360 |
| gggacgccat gcacggagat ggatgtgcca acgtcctca cagcaacgaa gaacaccaca | 420 |
| gagagtgagc tcgtctgtag ggcttccaag gtgcttcgca tattttattt aaaacatggg | 480 |
| aaaactccat gcttgaagaa gaactctagt gttctcatgg agctgcagag actctttcgg | 540 |
| gcttttcgat gcctggattc atcgataagc tgcaccatga atgagtccaa gtccacatca | 600 |
| ctgaaagact tcctggaaag cctaaagagc atcatgcaaa tggattactc gtag | 654 |

<210> SEQ ID NO 23
<211> LENGTH: 2527
<212> TYPE: DNA
<213> ORGANISM: Artificial
<220> FEATURE:
<223> OTHER INFORMATION: synthetic DNA

<400> SEQUENCE: 23

| | |
|---|---|
| gccaccatgg agacagacac actcctgcta tgggtactgc tgctctgggt tccaggttcc | 60 |
| actggtgacg cggccctcga ggatgcagaa ttccgacatg actcaggata tgaagttcat | 120 |
| catcaaaaat tggtgttctt tgcagaagat gtgggttcaa acaaaggtgc aatcattgga | 180 |
| ctcatggtgg gcggtgttgt catagcgtga gtcgacggta ccgcgggccc gggatccgcc | 240 |
| cctctccctc ccccccccct aacgttactg gccgaagccg cttggaataa ggccggtgtg | 300 |
| cgtttgtcta tatgttattt tccaccatat tgccgtcttt tggcaatgtg agggcccgga | 360 |
| aacctggccc tgtcttcttg acgagcattc ctaggggtct ttcccctctc gccaaaggaa | 420 |
| tgcaaggtct gttgaatgtc gtgaaggaag cagttcctct ggaagcttct tgaagacaaa | 480 |
| caacgtctgt agcgaccctt tgcaggcagc ggaaccccc acctggcgac aggtgcctct | 540 |
| gcggccaaaa gccacgtgta agatacac ctgcaaaggc ggcacaaccc cagtgccacg | 600 |
| ttgtgagttg gatagttgtg gaaagagtca aatggctctc ctcaagcgta ttcaacaagg | 660 |
| ggctgaagga tgcccagaag gtaccccatt gtatgggatc tgatctgggg cctcggtgca | 720 |
| catgctttac atgtgtttag tcgaggttaa aaaaacgtct aggccccccg aaccacgggg | 780 |

```
acgtggtttt cctttgaaaa acacgatgat aatatggcca caaccctagt cctgcaggtt    840
taaacgaatt cgcccttgag gatccaccat gaccgcgcgg ggcgccgcgg ggcgctgccc    900
ttcttcgaca tggctgggct cccggctgct gctggtctgt ctcctcatga gcaggagtat    960
tgccaaggag gtgtcagaac actgtagcca catgattggg aatggacacc tgaaggtcct   1020
gcagcagttg atcgacagtc aaatggagac ttcatgccag attgcctttg aatttgtaga   1080
ccaggaacag ctggatgatc ctgtttgcta cctaaagaag gccttttttc tggtacaaga   1140
cataatagat gagaccatgc gctttaaaga caacaccccc aatgctaacg ccaccgagag   1200
gctccaggaa ctctccaata acctgaacag ctgcttcacc aaggactatg aggagcagaa   1260
caaggcctgt gtccgaactt ccatgagac tcctctccag ctgctggaga agatcaagaa   1320
cttctttaat gaaacaaaga atctccttga aaaggactgg aacatttta ccaagaactg   1380 caacaacagc tttgctaagt gctctagccg agatgtggtg accaagcctg attgcaactg   1440
cctgtaccct aaagccaccc ctagcagtga cccggcctct gcctcccctc accagccccc   1500
cgccccctcc atggcccctc tggctggctt ggcttgggat gattctcaga ggacagaggg   1560
cagctccctc ttgcccagtg agcttcccct tcgcatagag gacccaggca gtgccaagca   1620
gcgaccaccc aggagtacct gccagaccct cgagtcaaca gagcaaccaa accatgggga   1680
cagactcact gaggactcac aacctcatcc ttctgcgggg gggcccgtcc ctggggtgga   1740
agacattctt gaatcttcac tgggcactaa ctgggtccta aagaagcttc tggagaggc   1800 tagtgaggga tttttgaccc aggaagcaaa gttttcccc tccacgcctg tagggggcag   1860
catccaggca gagactgaca gacccagggc cctctcagca tctccattcc ctaaatcaac   1920
agaggaccaa aagccagtgg atataacaga caggccgttg acagaggtga accctatgag   1980
acccattggc cagacacaga ataatactcc tgagaagact gatggtacat ccacgctgcg   2040
tgaagaccac caggagccag gctctccccca tattgcgaca ccgaatcccc aacgagtcag   2100
caactcagcc accccgttg ctcagttact gcttcccaaa agccactctt ggggcattgt   2160
gctgcccctt ggggagcttg agggcaagag aagtaccagg gatcgaagga gccccgcaga   2220
gctggaagga ggatcagcaa gtgagggggc agccaggcct gtggcccgtt ttaattccat   2280
tcctttgact gacacaggcc atgtggagca gcatgaggga tcctctgacc cccagatccc   2340
tgagtctgtc ttccacctgc tggtgccggg catcatccta gtcttgctga ctgttggggg   2400
cctcctgttc tacaagtgga agtggaggag ccatcgaaac cctcagacat ggattcttc   2460 tgtgggcga ccagaggaca gctccctgac ccaggatgag gacagacagg tggaactgcc   2520
agtatag                                                             2527
```

<210> SEQ ID NO 24
<211> LENGTH: 18
<212> TYPE: DNA
<213> ORGANISM: Artificial
<220> FEATURE:
<223> OTHER INFORMATION: synthetic DNA

<400> SEQUENCE: 24
tcttctggtg gtggtggt                                                    18

<210> SEQ ID NO 25
<211> LENGTH: 1323
<212> TYPE: DNA
<213> ORGANISM: Artificial
<220> FEATURE:
<223> OTHER INFORMATION: synthetic DNA

<400> SEQUENCE: 25

```
gccaccatgg aaaccgacac cctgctgctg tgggtgctgc tgctctgggt cccaggatct      60
acaggcgacg ccgccctcga ggacgccgag ttcagacacg acagcggcta cgaggtgcac     120
caccagaaac tggtgttctt cgccgaggac gtgggcagca caagggcgc catcatcggc      180
ctgatggtcg gcggagtggt cattgccggt accgagccca gagcagcga caagacccac     240
accagccctc caagccctgc ccctgagctg ctgggcggac ccagcgtgtt cctgttcccc     300
ccaaagccca aggacaccct gatgatcagc cggaccccg aagtgacctg cgtggtggtg     360
gacgtgtccc acgaggaccc tgaagtgaag ttcaattggt acgtggacgg cgtggaggtg     420
cacaacgcca agaccaagcc ccgggaggaa cagtacaaca gcacctaccg ggtggtgtcc     480
gtgctgaccg tgctgcacca ggactggctg aacggcaaag agtacaagtg caaggtctcc     540
aacaaggccc tgcctgcccc catcgagaaa accatcagca aggccaaggg ccagcctcgg     600
gagcctcagg tgtacaccct gcccccagc agggacgagc tgaccaagaa ccaggtgtcc      660
ctgacctgcc tggtcaaggg cttctacccc agcgatatcg ccgtggagtg ggagagcaac     720
ggccagcccg agaacaacta caagaccacc cccctgtgc tggacagcga cggcagcttc      780
ttcctgtact ccaaactgac cgtggacaag agccggtggc agcagggcaa cgtgttcagc     840
tgcagcgtga tgcacgaggc cctgcacaac cactacaccc agaagtccct gagcctgagc     900
cctggcaagg tcgacagcag cggaggcgga ggccacaagt cgacatcac cctgcaggaa      960
atcatcaaga ccctgaacag cctgaccgag cagaaaaccc tgtgcaccga gctgaccgtg    1020
accgacatct cgccgccag caagaacacc accgagaaag agacattctg cagagccgcc    1080
accgtgctgc ggcagttcta cagccaccac gagaaggaca ccagatgtct gggcgccacc    1140
gcccagcagt tccaccggca aagcagctg atccggttcc tgaagcggct ggacagaaat    1200
ctgtggggcc tggccggcct gaacagctgc ccgtgaaag aggccaacca gagcaccctg     1260
gaaaactttc tggaacggct caagaccatc atgcgggaga gtacagcaa gtgcagcagc    1320
tga                                                                  1323
```

<210> SEQ ID NO 26
<211> LENGTH: 1311
<212> TYPE: DNA
<213> ORGANISM: Artificial
<220> FEATURE:
<223> OTHER INFORMATION: synthetic DNA

<400> SEQUENCE: 26

```
gccaccatgg aaaccgacac cctgctgctg tgggtgctgc tgctctgggt cccaggatct      60
acaggcgacg ccgccctcga ggacgccgag ttcagacacg acagcggcta cgaggtgcac     120
caccagaaac tggtgttctt cgccgaggac gtgggcagca caagggcgc catcatcggc      180
ctgatggtcg gcggagtggt cattgccggt accgagcccc gggtgccat cacccagaac     240
cccagccccc cactgaaaga gagcccccccc tctgccgctc ctgatctgct gggcggaccc    300
agcgtgttca tcttcccacc caagatcaag gacgtgctga tgatcagcct gagccccatg     360
gtgaccagcg tggtggtgga cgtgtccgag gacgacccg acgtgcagat cagttggttc     420
gtgaacaacg tggaggtgca caccgcccag accagaccc accgggagga ctacaacagc    480
accctgagag tggtgtccgc cctgcccatc cagcaccagg actggatgag cggcaaagaa     540
ttcaagcagca aagtgaacaa ccgggccctg cccagcccca tcgagaaaac catcagcaag    600
cccagaggcc ctgtgcgggc tcctcaggtg tacgtgctgc cccaccccgc cgaggaaatg    660
```

| | |
|---|---|
| accaagaaag agttcagcct gaccagcatg atcaccggct ttctgcccgc cgagatcgcc | 720 |
| gtggactgga ccagcaacgg ccggaccgag cagaactaca agaacaccgc caccgtgctg | 780 |
| gacagcgacg gcagctactt catgtacagc aagctgcggg tgcagaagtc cacctgggag | 840 |
| agaggcagcc tgttcgccag cagcgtggtg cacgagggcc tgcacaacca cctgaccacc | 900 |
| aagaccatca gccggtccct gggagtcgac agcagcggag gcggaggcca catccacggc | 960 |
| tgcgacaaga accacctgag agagatcatc ggcatcctga cgaagtgac cggcgagggc | 1020 |
| accccctgta ccgagatgga cgtgcccaac gtgctgaccg ccaccaagaa caccaccgag | 1080 |
| agcgagctgg tgtgccgggc cagcaaggtg ctgcggatct tctacctgaa gcacggcaag | 1140 |
| accccctgcc tgaagaaaaa cagcagcgtg ctgatggaac tgcagcggct gttccgggcc | 1200 |
| ttccggtgcc tggacagcag catcagctgc accatgaacg agagcaagag caccagcctg | 1260 |
| aaggactttc tggaaagcct gaagagtatc atgcagatgg actacagctg a | 1311 |

<210> SEQ ID NO 27
<211> LENGTH: 15
<212> TYPE: DNA
<213> ORGANISM: Artificial
<220> FEATURE:
<223> OTHER INFORMATION: synthetic DNA

<400> SEQUENCE: 27

| | |
|---|---|
| ggtggcggtg gctcg | 15 |

<210> SEQ ID NO 28
<211> LENGTH: 1746
<212> TYPE: DNA
<213> ORGANISM: Artificial
<220> FEATURE:
<223> OTHER INFORMATION: synthetic DNA

<400> SEQUENCE: 28

| | |
|---|---|
| gccaccatgg aaaccgacac cctgctgctg tgggtgctgc tgctctgggt cccaggatct | 60 |
| acaggcgacg ccgccctcga ggacgccgag ttcagacacg acagcggcta cgaggtgcac | 120 |
| caccagaaac tggtgttctt cgccgaggac gtgggcagca acaagggcgc catcatcggc | 180 |
| ctgatggtcg gcggagtggt cattgccggc ggaggcggct ccgatgccga gttccggcac | 240 |
| gattccggct atgaagtcca ccatcagaag ctcgtctttt tgccgagga tgtgggtct | 300 |
| aacaaagggg ccattattgg gctcatggtc ggggggcgtcg tgattgctgg cggcggaggc | 360 |
| agcgacgctg agtttcgcca cgactccgga tacgaagtgc atcaccagaa gctggtcttt | 420 |
| ttcgctgaag atgtcggcag taacaagggg gctattattg gtctgatggt cggcggagtc | 480 |
| gtgatcgcag ggggagggg aagcgacgcc gaattcaggc atgactctgg atatgaggtc | 540 |
| caccaccaga aactcgtgtt ttttgctgag gacgtcggct caaacaaagg cgctatcatt | 600 |
| ggactcatgg tcgaggcgt ggtcattgca ggtaccgagc ccaagagcag cgacaagacc | 660 |
| cacaccagcc ctccaagccc tgcccctgag ctgctgggcg acccagcgt gttcctgttc | 720 |
| cccccaaagc ccaaggacac cctgatgatc agccggaccc ccgaagtgac ctgcgtggtg | 780 |
| gtggacgtgt cccacgagga ccctgaagtg aagttcaatt ggtacgtgga cggcgtggag | 840 |
| gtgcacaacg ccaagaccaa gccccgggag gaacagtaca acagcaccta ccgggtggtg | 900 |
| tccgtgctga ccgtgctgca ccaggactgg ctgaacggca agagtacaa gtgcaaggtc | 960 |
| tccaacaagg ccctgcctgc ccccatcgag aaaaccatca gcaaggccaa gggccagcct | 1020 |
| cgggagcctc aggtgtacac cctgccccc agcagggacg agctgaccaa gaaccaggtg | 1080 |

-continued

| | |
|---|---|
| tccctgacct gcctggtcaa gggcttctac cccagcgata tcgccgtgga gtgggagagc | 1140 |
| aacggccagc ccgagaacaa ctacaagacc acccccctg tgctggacag cgacggcagc | 1200 |
| ttcttcctgt actccaaact gaccgtggac aagagccggt ggcagcaggg caacgtgttc | 1260 |
| agctgcagcg tgatgcacga ggccctgcac aaccactaca cccagaagtc cctgagcctg | 1320 |
| agccctggca aggtcgacag cagcggaggc ggaggccaca agtgcgacat caccctgcag | 1380 |
| gaaatcatca agaccctgaa cagcctgacc gagcagaaaa ccctgtgcac cgagctgacc | 1440 |
| gtgaccgaca tcttcgccgc cagcaagaac accaccgaga aagagacatt ctgcagagcc | 1500 |
| gccaccgtgc tgcggcagtt ctacagccac acgagaagg acaccagatg tctgggcgcc | 1560 |
| accgccagc agttccaccg gcacaagcag ctgatccggt tcctgaagcg gctggacaga | 1620 |
| aatctgtggg gcctggccgg cctgaacagc tgccccgtga agaggccaa ccagagcacc | 1680 |
| ctggaaaact ttctggaacg gctcaagacc atcatgcggg agaagtacag caagtgcagc | 1740 |
| agctga | 1746 |

<210> SEQ ID NO 29
<211> LENGTH: 1734
<212> TYPE: DNA
<213> ORGANISM: Artificial
<220> FEATURE:
<223> OTHER INFORMATION: synthetic DNA

<400> SEQUENCE: 29

| | |
|---|---|
| gccaccatgg aaaccgacac cctgctgctg tgggtgctgc tgctctgggt cccaggatct | 60 |
| acaggcgacg ccgccctcga ggacgccgag ttcagacacg acagcggcta cgaggtgcac | 120 |
| caccagaaac tggtgttctt cgccgaggac gtgggcagca caagggcgc catcatcggc | 180 |
| ctgatggtcg gcggagtggt cattgccggc ggaggcggct ccgatgccga gttccggcac | 240 |
| gattccggct atgaagtcca ccatcagaag ctcgtctttt tgccgagga tgtgggtct | 300 |
| aacaaagggg ccattattgg gctcatggtc gggggcgtcg tgattgctgg cggcggaggc | 360 |
| agcgacgctg agtttcgcca cgactccgga tacgaagtgc atcaccagaa gctggtcttt | 420 |
| ttcgctgaag atgtcggcag taacaagggg gctattattg gtctgatggt cggcggagtc | 480 |
| gtgatcgcag ggggagggg aagcgacgcc gaattcaggc atgactctgg atatgaggtc | 540 |
| caccaccaga aactcgtgtt ttttgctgag gacgtcggct caaacaaagg cgctatcatt | 600 |
| ggactcatgg tcgaggcgt ggtcattgca ggtaccgagc ccgggtgcc catcacccag | 660 |
| aaccccagcc ccccactgaa agagagcccc ccctctgccg ctcctgatct gctgggcgga | 720 |
| cccagcgtgt tcatcttccc acccaagatc aaggacgtgc tgatgatcag cctgagcccc | 780 |
| atggtgacca gcgtggtggt ggacgtgtcc gaggacgacc ccgacgtgca gatcagttgg | 840 |
| ttcgtgaaca acgtggaggt gcacaccgcc cagacccaga cccaccggga ggactacaac | 900 |
| agcaccctga gtggtgtc cgccctgccc atccagcacc aggactggat gagcggcaaa | 960 |
| gaattcaaga gcaaagtgaa caaccggggc ctgcccagcc ccatcgagaa aaccatcagc | 1020 |
| aagcccagag ccctgtgcg ggctcctcag gtgtacgtgc tgccccacc cgccgaggaa | 1080 |
| atgaccaaga aagagttcag cctgaccagc atgatcaccg ctttctgcc cgccgagatc | 1140 |
| gccgtggact ggaccagcaa cggccggacc gagcagaact acaagaacac cgccaccgtg | 1200 |
| ctggacagcg acggcagcta cttcatgtac agcaagctgc gggtgcagaa gtccaccctgg | 1260 |
| gagagaggca gcctgttcgc cagcagcgtg gtgcacgagg gcctgcacaa ccacctgacc | 1320 |

| | |
|---|---|
| accaagacca tcagccggtc cctgggagtc gacagcagcg gaggcggagg ccacatccac | 1380 |
| ggctgcgaca agaaccacct gagagagatc atcggcatcc tgaacgaagt gaccggcgag | 1440 |
| ggcacccccct gtaccgagat ggacgtgccc aacgtgctga ccgccaccaa gaacaccacc | 1500 |
| gagagcgagc tggtgtgccg ggccagcaag gtgctgcgga tcttctacct gaagcacggc | 1560 |
| aagacccccct gcctgaagaa aaacagcagc gtgctgatgg aactgcagcg gctgttccgg | 1620 |
| gccttccggt gcctggacag cagcatcagc tgcaccatga acgagagcaa gagcaccagc | 1680 |
| ctgaaggact ttctggaaag cctgaagagt atcatgcaga tggactacag ctga | 1734 |

<210> SEQ ID NO 30
<211> LENGTH: 1335
<212> TYPE: DNA
<213> ORGANISM: Artificial
<220> FEATURE:
<223> OTHER INFORMATION: synthetic DNA

<400> SEQUENCE: 30

| | |
|---|---|
| gccaccatgg aaaccgacac cctgctgctg tgggtgctgc tgctctgggt cccaggatct | 60 |
| acaggcgacg ccgccctcga ggacgccgag ttcagacacg acagcggcta cgaggtgcac | 120 |
| caccagaaac tggtgttctt cgccgaggac gtgggcagca caagggcgc catcatcggc | 180 |
| ctgatggtcg gcggagtggt cattgccggc ggaggcggct ccgatgccga gttccggcac | 240 |
| gattccggct atgaagtcca ccatcagaag ctcgtctttt tgccgagga tgtggggtct | 300 |
| aacaaagggg ccattattgg gctcatggtc ggggcgtcg tgattgctgg cggcggaggc | 360 |
| agcgacgctg agtttcgcca cgactccgga tacgaagtgc atcaccagaa gctggtcttt | 420 |
| ttcgctgaag atgtcggcag taacaagggg gctattattg gtctgatggt cggcggagtc | 480 |
| gtgatcgcag ggggagggg aagcgacgcc gaattcaggc atgactctgg atatgaggtc | 540 |
| caccaccaga aactcgtgtt ttttgctgag gacgtcggct caaacaaagg cgctatcatt | 600 |
| ggactcatgg tcggaggcgt ggtcattgca ggtaccgagc caagagcag cgacaagacc | 660 |
| cacaccagcc ctccaagccc tgcccctgag ctgctgggcg acccagcgt gttcctgttc | 720 |
| cccccaaagc caaggacac cctgatgatc agccggaccc ccgaagtgac ctgcgtggtg | 780 |
| gtggacgtgt cccacgagga ccctgaagtg aagttcaatt ggtacgtgga cggcgtggag | 840 |
| gtgcacaacg ccaagaccaa gccccgggag gaacagtaca acagcaccta ccgggtggtg | 900 |
| tccgtgctga ccgtgctgca ccaggactgg ctgaacggca agagtacaa gtgcaaggtc | 960 |
| tccaacaagg ccctgcctgc ccccatcgag aaaaccatca gcaaggccaa gggccagcct | 1020 |
| cgggagcctc aggtgtacac cctgcccccc agcagggacg agctgaccaa gaaccaggtg | 1080 |
| tccctgacct gcctggtcaa gggcttctac cccagcgata tcgccgtgga gtgggagagc | 1140 |
| aacggccagc ccgagaacaa ctacaagacc accccccctg tgctggacag cgacggcagc | 1200 |
| ttcttcctgt actccaaact gaccgtggac aagagccggt ggcagcaggg caacgtgttc | 1260 |
| agctgcagcg tgatgcacga ggccctgcac aaccactaca cccagaagtc cctgagcctg | 1320 |
| agccctggca agtga | 1335 |

<210> SEQ ID NO 31
<211> LENGTH: 1350
<212> TYPE: DNA
<213> ORGANISM: Artificial
<220> FEATURE:
<223> OTHER INFORMATION: synthetic DNA

<400> SEQUENCE: 31

```
gccaccatgg aaaccgacac cctgctgctg tgggtgctgc tgctctgggt cccaggatct    60
acaggcgacg ccgccctcga ggacgccgag ttcagacacg acagcggcta cgaggtgcac   120
caccagaaac tggtgttctt cgccgaggac gtgggcagca caagggcgc catcatcggc    180
ctgatggtcg gcggagtggt cattgccggc ggaggcggct ccgatgccga gttccggcac   240
gattccggct atgaagtcca ccatcagaag ctcgtctttt tgccgagga tgtgggtct    300
aacaaagggg ccattattgg gctcatggtc ggggcgtcg tgattgctgg cggcggaggc   360
agcgacgctg agtttcgcca cgactccgga tacgaagtgc atcaccagaa gctggtcttt   420
ttcgctgaag atgtcggcag taacaagggg gctattattg gtctgatggt cggcggagtc   480
gtgatcgcag gggagggg aagcgacgcc gaattcaggc atgactctgg atatgaggtc     540
caccaccaga aactcgtgtt ttttgctgag gacgtcggct caaacaaagg cgctatcatt   600
ggactcatgg tcggaggcgt ggtcattgca ggtaccgagc cccgggtgcc catcacccag   660
aaccccagcc cccactgaa agagagcccc ccctctgccg ctcctgatct gctgggcgga    720
cccagcgtgt tcatcttccc acccaagatc aaggacgtgc tgatgatcag cctgagcccc   780
atggtgacca cgtggtggt ggacgtgtcc gaggacgacc ccgacgtgca gatcagttgg    840
ttcgtgaaca acgtggaggt gcacaccgcc cagacccaga cccacgggga ggactacaac   900
agcaccctga gtggtgtc cgccctgccc atccagcacc aggactggat gagcggcaaa     960
gaattcaaga gcaaagtgaa caaccggggcc ctgcccagcc ccatcgagaa accatcagc   1020
aagcccagag ccctgtgcg ggctcctcag gtgtacgtgc tgcccccacc cgccgaggaa   1080
atgaccaaga aagagttcag cctgaccagc atgatcaccg gctttctgcc cgccgagatc   1140
gccgtggact ggaccagcaa cggccggacc gagcagaact acaagaacac cgccaccgtg   1200
ctggacagcg acggcagcta cttcatgtac agcaagctgc gggtgcagaa gtccacctgg   1260
gagagaggca gcctgttcgc cagcagcgtg gtgcacgagg cctgcacaa ccacctgacc    1320
accaagacca tcagccggtc cctgggatga                                     1350
```

<210> SEQ ID NO 32
<211> LENGTH: 696
<212> TYPE: DNA
<213> ORGANISM: Homo sapiens

<400> SEQUENCE: 32

```
gagcccaaga gcagcgacaa gacccacacc agccctccaa gccctgcccc tgagctgctg    60
ggcggaccca gcgtgttcct gttcccccca agcccaagg acaccctgat gatcagccgg   120
acccccgaag tgacctgcgt ggtggtggac gtgtcccacg aggaccctga agtgaagttc   180
aattggtacg tggacggcgt ggaggtgcac aacgccaaga ccaagccccg ggaggaacag   240
tacaacagca cctaccgggt ggtgtccgtg ctgaccgtgc tgcaccagga ctggctgaac   300
ggcaaagagt acaagtgcaa ggtctccaac aaggccctgc ctgcccccat cgagaaaacc   360
atcagcaagg ccaagggcca gcctcgggag cctcaggtgt acaccctgcc cccagcagg   420
gacgagctga ccaagaacca ggtgtccctg acctgcctgg tcaagggctt ctaccccagc   480
gatatcgccg tggagtggga gagcaacggc cagcccgaga caactacaa gaccacccccc   540
cctgtgctgg acagcgacgg cagcttcttc ctgtactcca aactgaccgt ggacaagagc   600
cggtggcagc agggcaacgt gttcagctgc agcgtgatgc acgaggccct gcacaaccac   660
tacacccaga gtccctgag cctgagccct ggcaag                              696
```

```
<210> SEQ ID NO 33
<211> LENGTH: 711
<212> TYPE: DNA
<213> ORGANISM: Mus musculus

<400> SEQUENCE: 33
gagccccggg tgcccatcac ccagaacccc agcccccac tgaaagagag ccccccctct      60
gccgctcctg atctgctggg cggacccagc gtgttcatct tcccacccaa gatcaaggac    120
gtgctgatga tcagcctgag ccccatggtg accagcgtgg tggtggacgt gtccgaggac    180
gaccccgacg tgcagatcag ttggttcgtg aacaacgtgg aggtgcacac cgcccagacc    240
cagacccacc gggaggacta acagcacc ctgagagtgg tgtccgccct gcccatccag      300
caccaggact ggatgagcgg caaagaattc aagagcaaag tgaacaaccg ggccctgccc    360
agccccatcg agaaaaccat cagcaagccc agaggccctg tgcgggctcc tcaggtgtac    420
gtgctgcccc cacccgccga ggaaatgacc aagaaagagt tcagcctgac cagcatgatc    480
accggctttc tgcccgccga gatcgccgtg gactggacca gcaacggccg gaccgagcag    540
aactacaaga acaccgccac cgtgctggac agcgacggca gctacttcat gtacagcaag    600
ctgcgggtgc agaagtccac ctgggagaga ggcagcctgt tcgccagcag cgtggtgcac    660
gagggcctgc acaaccacct gaccaccaag accatcagcc ggtccctggg a              711

<210> SEQ ID NO 34
<211> LENGTH: 20
<212> TYPE: DNA
<213> ORGANISM: Artificial
<220> FEATURE:
<223> OTHER INFORMATION: synthetic DNA

<400> SEQUENCE: 34
catcgagaaa accatcagca                                                  20

<210> SEQ ID NO 35
<211> LENGTH: 20
<212> TYPE: DNA
<213> ORGANISM: Artificial
<220> FEATURE:
<223> OTHER INFORMATION: synthetic DNA

<400> SEQUENCE: 35
ctggttcttg gtcagctcgt                                                  20
```

DNA VACCINE FOR ALZHEIMER'S DISEASE

This application is a continuation-in-part of copending U.S. application Ser. No. 13/257,713 filed on Sep. 20, 2011, which is the U.S. National Phase of PCT/JP2010/055308 filed on Mar. 26, 2010. This application claims the benefit of the filing date of Patent Application No. 2009-075832 filed in Japan on Mar. 26, 2009. These documents are hereby expressly incorporated by reference for all purposes.

TECHNICAL FIELD

The present invention relates to DNA vaccines for Alzheimer's disease.

BACKGROUND ART

Alzheimer's disease (AD) is a disease which frequently occurs in middle-aged or older people and whose major symptom is cognitive impairment (including memory disorder, orientation disturbance, learning disorder, attention disorder, spatial cognitive impairment, problem-solving impairment, etc.). Symptoms of this disease progress over several years, during which there often appear problem behaviors such as persecutory delusion, hallucination, offensive language, violence, wandering, and unclean behavior. This causes unwanted effects not only on patients themselves, but also on those around them including their family members and physicians, nurses, therapists, etc.

Alzheimer's disease has three pathological features, i.e., senile plaques (Aβ deposition), neurofibrillary tangles (tau deposition), and neuronal loss. Many studies have indicated that Aβ deposition occurs prior to tau deposition and neuronal changes, and the "amyloid hypothesis" has become widely known, which states that prevention of Aβ deposition would allow some avoidance of the subsequent events, i.e., tau accumulation in neurons, loss of neurons and so on.

Based on the amyloid hypothesis, Aβ peptide vaccine therapy has been proposed as a radical therapy for Alzheimer's disease (Non-patent Document 1). This vaccine therapy is based on the experiments in mice, in which the mice were externally administered with the Aβ peptide together with an immune activator (adjuvant) to induce in vivo production of anti-Aβ antibody to thereby reduce Aβ accumulation in the brain.

However, clinical trials in humans have been discontinued because of side effect problems, such as meningoencephalitis developed in cases receiving real drugs.

Following these clinical trials, further development has proceeded in an attempt to design vaccine formulations which do not cause encephalitis. The Aβ peptide is known to induce Th1 responses primarily through its C-terminal fragment and Th2 responses through its N-terminal fragment. Thus, clinical trials have been conducted for vaccines comprising an N-terminal fragment of Aβ attached to a carrier protein (Non-patent Document 2).

However, it was still difficult to overcome side effects including encephalitis.

For this reason, DNA vaccine therapy has been developed as a new vaccine therapy for Alzheimer's disease, which is an alternative to these Aβ peptide vaccines. Moreover, the inventors of the present invention have developed DNA vaccines which are effective for elimination of deposited Aβ and are also highly safe (Non-patent Document 3). A known example of the DNA vaccines developed by the inventors is an IgL-Aβ-Fc vaccine (Patent Document 1).

Recent studies have been indicating that there are various subspecies of neurotoxic Aβ. Aβ oligomers, which are most intensively analyzed, can be divided into two major types, i.e., those of low-molecular-weight type assembled from 2, 3 or 4 molecules and those of high-molecular-weight type assembled from 12 or more molecules. Moreover, strong neurotoxicity is also observed in pEAβ3-42, which is N-terminally truncated and pyrrole-derivatized by post-translational modification (Non-patent Documents 4 and 5). Furthermore, some findings are also being obtained, which suggest that other molecules such as ABri (Non-patent Document 6) and ADan, which have high amyloid aggregation propensity although their amino acid sequences are completely different from that of Aβ, are also involved in the onset of Alzheimer's disease.

PRIOR ART DOCUMENTS

Patent Documents

[Patent Document 1] WO 2005/014041 A2

Non-patent Documents

[Non-patent Document 1] Schenk D. et al., Nature 400: 173-177, 1999
[Non-patent Document 2] Masters C L et al., Brain 129: 2823-2839, 2006
[Non-patent Document 3] Y. Okura, et al., PNAS vol. 103: 9619-9624, 2006
[Non-patent Document 4] Saido et al., Neurosci Lett, 215, 173-176, 1996
[Non-patent Document 5] Schlenzig et al., Biochemistry, 48, 7072-7078, 2009
[Non-patent Document 6] Ghiso et al., Brain Pathol, 16, 71-79, 2006

DISCLOSURE OF THE INVENTION

Problems to be Solved by the Invention

In light of these previous studies, there has been a demand for the development of DNA vaccine therapy which is more effective and safer than existing DNA vaccines.

Means for Solving the Problems

As a result of extensive and intensive efforts made to solve the above problems, the inventors of the present invention have constructed a vector which carries DNA encoding Aβ and DNA encoding a Th2 cytokine, as well as a vector which carries DNA encoding Aβ, DNA encoding a Th2 cytokine and DNA encoding an immunoglobulin Fc sequence, and have found that these vectors have a therapeutic effect when administered to model animals of Alzheimer's disease. The inventors have further found that the above vectors also induce antibodies against a wide variety of molecules with neurotoxicity and high amyloid aggregation propensity (e.g., pEAβ3-42, ABri, ADan). These findings led to the completion of the present invention.

Namely, the present invention is as follows.
(1) A recombinant vector, which comprises DNA encoding amyloid 13 and DNA encoding a Th2 cytokine.
(2) The vector according to (1) above, which further comprises DNA encoding an immunoglobulin Fc sequence.
(3) The vector according to (1) or (2) above, wherein the DNA encoding amyloid 13 consists of repeats of itself (4) The vector according to any one of (1) to (3) above, wherein the amyloid β is Aβ1-42.
(5) The vector according to any one of (1) to (4) above, wherein the Th2 cytokine is interleukin-4 or M-CSF.
(6) A DNA vaccine for prevention or treatment of Alzheimer's disease, which comprises the recombinant vector according to any one of (1) to (5) above.
(7) A DNA vaccine for elimination of brain Aβ, which comprises the recombinant vector according to any one of (1) to (5) above.
(8) An inducer of anti-Aβ antibody, which comprises the recombinant vector according to any one of (1) to (5) above.
(9) A method for preventing or treating Alzheimer's disease, comprising administrating to a subject an effective amount of the recombinant vector according to any one of (1) to (5) above.
(10) A method of eliminating brain Aβ, comprising administrating to a subject an effective amount of the recombinant vector according to any one of (1) to (5) above.
(11) A method of inducing anti-Aβ antibody, comprising administrating to a subject an effective amount of the recombinant vector according to any one of (1) to (5) above.

Advantageous Effect of the Invention

The present invention provides DNA vaccines for Alzheimer's disease. The DNA vaccines of the present invention can be regarded as having a high therapeutic effect on Alzheimer's disease, due to their high affinity for senile plaques. Moreover, the present invention allows induction of antibodies against a wide variety of molecules with neurotoxicity and high amyloid aggregation propensity (e.g., pEAβ3-42, ABri, ADan).

BRIEF DESCRIPTION OF THE DRAWINGS

The patent or application file contains at least one color drawing. Copies of this patent or patent application publication with color drawing will be provided by the USPTO upon request and payment of the necessary fee.
FIG. 3A depicts results from the untreated group.
FIG. 3B depicts results from a group receiving existing vaccine.
FIG. 3C depicts results using the vaccine of the present invention.
FIG. 3D compares the Aβ-eliminating effect between existing vaccines and the vaccines of the present invention.
FIG. 25 shows primer design for YM3711 detection and specificity of quantitative PCR (qPCR).
FIG. 25A depicts a schematic of the YM3711 plasmid with all three primer pairs and Primer pair A.
FIG. 25B (left panel) shows that the PCR product was produced in a dose dependent manner.
FIG. 25B (right panel) shows that an empty vector was not amplified with Primer pair A.
FIG. 29 shows binding assays using YM3711P.
FIG. 31A depicts the protocol used.
FIG. 34 shows toxicology study of YM3711 in monkeys (A) and mice (B).

BEST MODES FOR CARRYING OUT THE INVENTION

Figure 1:
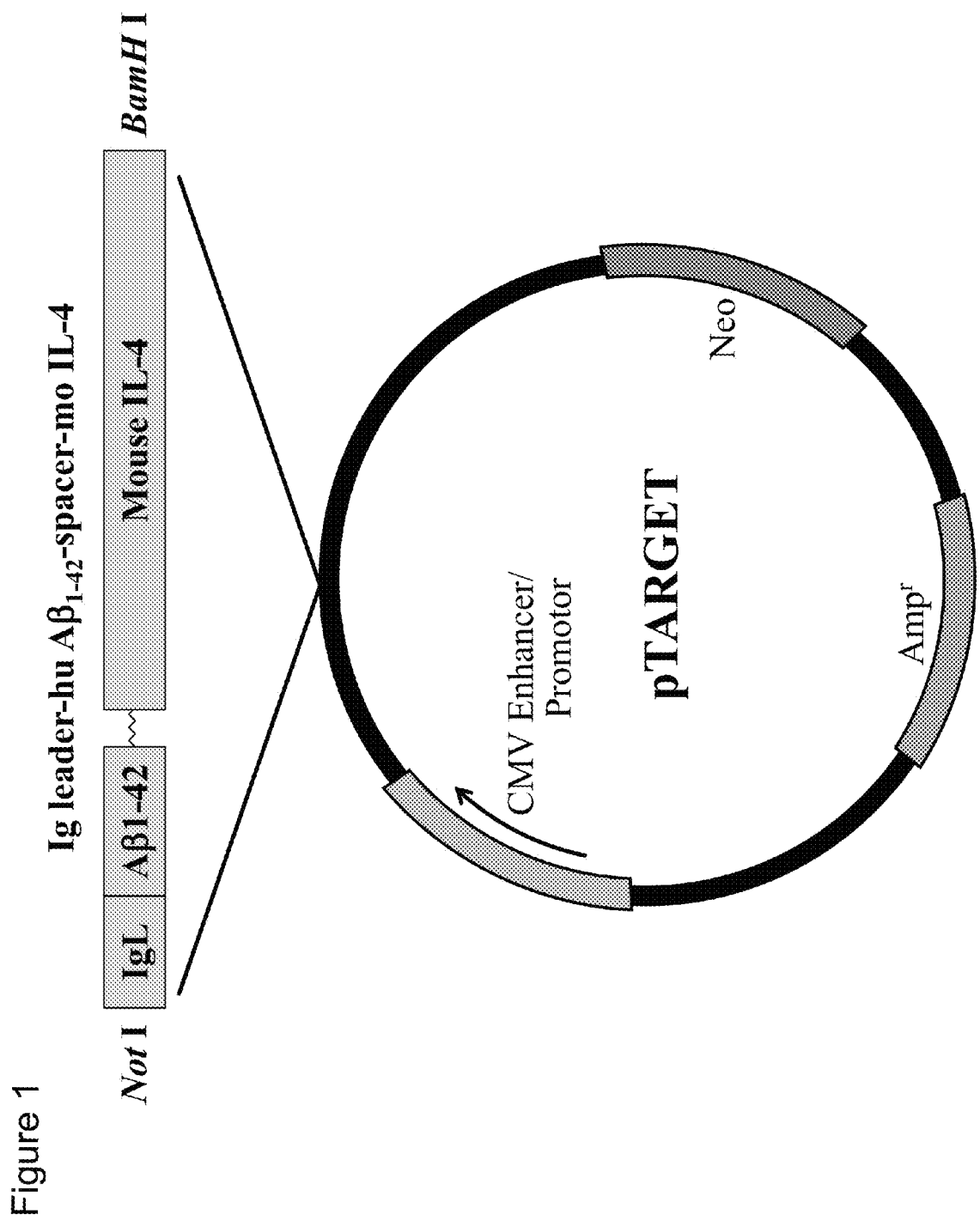
FIG. 1 shows the construction of a vector for use as the DNA vaccine of the present invention.

The present invention will be described in more detail below. The following embodiments are illustrated to describe the present invention, and it is not intended to limit the present invention only to these embodiments. The present invention can be implemented in various modes, without departing from the spirit of the present invention.

The present invention is directed to a DNA vaccine for Alzheimer's disease. The present invention is also directed to a vector constructed by ligating the Aβ gene with the Th2 cytokine gene. The present invention is further directed to a vector constructed by ligating the above vector with an immunoglobulin Fc (IgFc) sequence.

Such a DNA vaccine is intended to cause Aβ protein production in cells into which the vaccine is incorporated, which is accomplished when a gene for Aβ protein production is integrated into a vector (plasmid or virus) for gene transfer and administered to a patient. Aβ thus produced stimulates the immune system and induces anti-Aβ antibody (Y. Okura, et al., BRAN and NERVE 60(8): 931-940, 2008). DNA vaccines remain in the body for a long time after administration and continue to slowly produce the encoded peptides, so that excessive immune responses can be avoided, and DNA vaccines can also be modified due to their simple structure (Tang D C et al., Nature 356: 152-154, 1992; Barry M A et al., Nature 377: 632-635, 1995). Moreover, they are advantageous in that immune responses induced in a host are of Th2 type (Tang D C et al., Nature 356: 152-154, 1992; Ulmer J B et al., Science 259: 1745-1749, 1993; Hoffman S L et al., Ann N Y Acad Sci 772: 88-94, 1995).

In view of these facts, the inventors of the present invention have conceived that a gene encoding a Th2 cytokine is introduced together with the Aβ gene to thereby suppress side effects caused by cellular immunity, and have also constructed actual vaccines for Alzheimer's disease to study their effects. As a result, the vector of the present invention showed a high Aβ-eliminating effect at low doses and at reduced frequency. Moreover, the inventors have succeeded in promoting the extracellular release of expressed Aβ to more strongly stimulate immune responses against Aβ by introduction of a gene encoding an IgFc sequence, in addition to the genes encoding Aβ and a Th2 cytokine. Further, the inventors have succeeded in developing a vaccine with a higher brain Aβ-eliminating effect by construction of a vector comprising repeats of Aβ-encoding DNA. Furthermore, the inventors have found that the above vector also induces antibodies against a wide variety of molecules with neurotoxicity and high amyloid aggregation propensity (e.g., pEAβ3-42, ABri, ADan).

Thus, the vector of the present invention comprises DNA encoding Aβ and DNA encoding a Th2 cytokine as foreign genes. In another embodiment, the vector of the present invention comprises DNA encoding an IgFc sequence, in addition to the DNA encoding Aβ and the DNA encoding a Th2 cytokine. In yet another embodiment, the DNA encoding Aβ contained in the vector of the present invention consists of repeats of itself.

Although such Aβ, Th2 cytokine and IgFc sequence may be derived from animals of the same or different species as the target animal to be administered with the DNA vaccine, those derived from animals of the same species are preferred for use.

DNA encoding Aβ, DNA encoding a Th2 cytokine and DNA encoding an IgFc sequence have already been cloned. Thus, DNAs contained in the vector of the present invention can be obtained by standard genetic engineering procedures. For example, it is possible to use nucleic acid synthesis techniques with a DNA synthesizer, which are commonly used as genetic engineering procedures. Alternatively, it is also possible to use PCR techniques in which DNA sequences serving as templates are isolated or synthesized, and primers specific for each DNA are then designed to amplify each gene sequence with a PCR system, or to use gene amplification techniques in which cloning vectors are used. The techniques listed above would be readily performed by those skilled in the art, according to Molecular cloning 2nd Edt. Cold Spring Harbor Laboratory Press (1989), etc. For purification of the resulting PCR products, any known method may be used.

Amyloid β protein (Aβ) is a polypeptide composed of 40 to 43 amino acids, which is cleaved from its precursor protein (APP: amyloid β protein precursor) by the action of β- and γ-secretases.

To present antigenicity against Aβ, such a polypeptide comprises 15 or more contiguous amino acids, preferably 20 or more contiguous amino acids derived from the native Aβ amino acid sequence. A polypeptide comprising the native full-length Aβ may also be used.

The nucleotide sequences of these DNAs are available from a certain database. For example, GENEBANK® annotated collection of publicly available DNA sequences Accession No. NC_000021.7 may be used for human Aβ, while Accession No. NC_000082.5 may be used for mouse Aβ.

In a preferred embodiment of the present invention, the above DNAs may be used as templates for PCR with primers specific for these genes to prepare each DNA region with each fragment length. In the present invention, it is possible to use a polypeptide of a region covering 43 amino acids cleaved by the action of γ-secretase (referred to as "Aβ1-43"), a region covering N-terminal Aβ amino acids 1 to 20 (referred to as "Aβ1-20"), a region covering N-terminal amino acids 1 to 40 (referred to as "Aβ1-40"), or a region covering N-terminal amino acids 1 to 42 (referred to as "Aβ1-42"). The amino acid sequences of human Aβ1-43, Aβ1-20, Aβ1-40 and Aβ1-42 are shown in SEQ ID NOs: 2, 4, 6 and 8, respectively, while those of mouse Aβ1-43, Aβ-20, Aβ1-40 and Aβ1-42 are shown in SEQ ID NOs: 10, 12, 14 and 16, respectively.

The nucleotide sequences of DNAs encoding human Aβ1-43, Aβ1-20, Aβ1-40 and Aβ1-42 are shown in SEQ ID NOs: 1, 3, 5 and 7, respectively, while the nucleotide sequences of DNAs encoding mouse Aβ1-43, Aβ1-20, Aβ1-40 and Aβ1-42 are shown in SEQ ID NOs: 9, 11, 13 and 15, respectively.

DNAs encoding human or mouse Aβ1-20, Aβ1-40 and Aβ1-42 may be prepared by PCR or other techniques from DNA encoding human or mouse Aβ1-43.

In addition to the above DNAs encoding human or mouse Aβ1-43, Aβ1-20, Aβ1-40 and Aβ1-42, the following DNAs may also be used in the present invention. DNA which is hybridizable under stringent conditions with DNA consisting of a nucleotide sequence complementary to the nucleotide sequence shown in SEQ ID NO: 1 and which encodes a protein having human Aβ activity.

DNA which is hybridizable under stringent conditions with DNA consisting of a nucleotide sequence complementary to the nucleotide sequence shown in SEQ ID NO: 3 and which encodes a protein having human Aβ activity.

DNA which is hybridizable under stringent conditions with DNA consisting of a nucleotide sequence complementary to the nucleotide sequence shown in SEQ ID NO: 5 and which encodes a protein having human Aβ activity.

DNA which is hybridizable under stringent conditions with DNA consisting of a nucleotide sequence complementary to the nucleotide sequence shown in SEQ ID NO: 7 and which encodes a protein having human Aβ activity.

DNA which is hybridizable under stringent conditions with DNA consisting of a nucleotide sequence complementary to the nucleotide sequence shown in SEQ ID NO: 9 and which encodes a protein having mouse Aβ activity.

DNA which is hybridizable under stringent conditions with DNA consisting of a nucleotide sequence complementary to the nucleotide sequence shown in SEQ ID NO: 11 and which encodes a protein having mouse Aβ activity.

DNA which is hybridizable under stringent conditions with DNA consisting of a nucleotide sequence complementary to the nucleotide sequence shown in SEQ ID NO: 13 and which encodes a protein having mouse Aβ activity.

DNA which is hybridizable under stringent conditions with DNA consisting of a nucleotide sequence complementary to the nucleotide sequence shown in SEQ ID NO: 15 and which encodes a protein having mouse Aβ activity.

In the context of the present invention, the term "Aβ activity" is intended to mean the ability to produce, accumulate and/or aggregate Aβ in the brain of a subject (e.g., human, mouse) to thereby form Aβ deposition (senile plaques). Aβ activity can be measured by immunological procedures such as immunohistological staining, ELISA and the like. For example, in the case of immunohistological staining, a protein to be evaluated may be expressed in the brain of a subject animal (e.g., mouse), and sections of the expressed tissue may be immunostained with anti-Aβ antibody to detect Aβ production, accumulation, aggregation and/or deposition for activity assay.

Human Aβ1-43, human Aβ1-20, human Aβ1-40, human Aβ1-42, mouse Aβ1-43, mouse Aβ1-20, mouse Aβ1-40 and mouse Aβ1-42 have their own Aβ activity. Thus, for example, in the case of a protein expressed from DNA which is hybridizable under stringent conditions with DNA consisting of a nucleotide sequence complementary to the nucleotide sequence shown in SEQ ID NO: 1 and which encodes a protein having human Aβ activity, it is sufficient for this protein to have Aβ activity equal to that of human Aβ1-43. The same also applies to proteins expressed from DNAs which are hybridizable under stringent conditions with DNAs consisting of nucleotide sequences complementary to the nucleotide sequences shown in the other SEQ ID NOs and which encode proteins having Aβ activity.

Stringent conditions in the above hybridization include, for example, conditions of 0.1×SSC to 10×SSC, 0.1% to 1.0% SDS and 20° C. to 80° C., more specifically prehybridization at 37° C. to 56° C. for 30 minutes or longer and the subsequent one to three washings in 0.1×SSC, 0.1% SDS at room temperature for 10 to 20 minutes. For detailed procedures of hybridization, reference may be made to "Molecular Cloning, A Laboratory Manual 2nd ed." (Cold Spring Harbor Press (1989)), etc.

It is also possible to use DNA which shares a homology of 50% or more, 60% or more, 70% or more, 80% or more, 90% or more, 95% or more, 98% or more, or 99% or more with the nucleotide sequence shown in SEQ ID NO: 1, 3, 5 or 7 and which encodes a protein functionally equivalent to the structural protein of human Aβ1-43, Aβ1-20, Aβ1-40 or Aβ1-42.

It is further possible to use DNA which shares a homology of 50% or more, 60% or more, 70% or more, 80% or more, 90% or more, 95% or more, 98% or more, or 99% or more with the nucleotide sequence shown in SEQ ID NO: 9, 11, 13 or 15 and which encodes a protein functionally equivalent to the structural protein of mouse Aβ1-43, Aβ1-20, Aβ1-40 or Aβ1-42.

The term "functionally equivalent" is intended to mean having the function of causing Aβ deposition (senile plaques) in tissues, etc.

In the present invention, DNA encoding Aβ may consists of repeats of the DNA encoding Aβ. A vector comprising repeats of Aβ-encoding DNA allows multiple Aβ molecules to be expressed simultaneously. Moreover, Aβ molecules released into the extracellular environment would form an oligomer. This oligomer stimulates the immune system to induce anti-Aβ oligomer antibody. As a result, it can be expected to eliminate Aβ oligomers whose neurotoxicity is stronger than that of Aβ monomers. There is no limitation on the repeated number of Aβ-encoding DNAs as long as the folded structure of Aβ is formed to give higher antigenicity than that of Aβ monomers. The number of repeats preferably ranges from 2 to 4, more preferably from 3 to 4.

In the context of the present invention, the term "Th2" is intended to mean a subgroup of $CD4^+$ T cells (commonly called helper T cells), and refers to cells that are induced to differentiate from T cells not experiencing any contact with antigen proteins (i.e., naive T cells) upon stimulation with cytokines such as IL-4 or IL-13. Th2 is involved in regulation of humoral immunity, and cytokines produced from Th2 promote antibody production. Examples of Th2 cytokines include IL-4 (interleukin-4), IL-5, IL-6, IL-10, IL-13, M-CSF (macrophage-colony-stimulating factor) and so on, with IL-4 being preferred.

GENEBANK® annotated collection of publicly available DNA sequences Accession Nos. NM_000589.2 and NM_021283.1 may be used for human IL-4 and mouse IL-4, respectively. Likewise, GENEBANK® annotated collection of publicly available DNA sequences Accession Nos. NM_000757.4 and NM_007778.3 may be used for human M-CSF and mouse M-CSF, respectively.

SEQ ID NOs of the nucleotide sequences of the above DNAs encoding IL-4 and M-CSF are shown below.

Human IL-4: SEQ ID NO: 17
Mouse IL-4: SEQ ID NO: 18
Human M-CSF: SEQ ID NO: 19
Mouse M-CSF: SEQ ID NO: 20

In addition to the above DNAs encoding Th2 cytokines, the following DNAs may also be used in the present invention.

DNA which is hybridizable under stringent conditions with DNA consisting of a nucleotide sequence complementary to the nucleotide sequence shown in SEQ ID NO: 17 and which encodes a protein having human IL-4 activity.

DNA which is hybridizable under stringent conditions with DNA consisting of a nucleotide sequence complementary to the nucleotide sequence shown in SEQ ID NO: 18 and which encodes a protein having mouse IL-4 activity.

DNA which is hybridizable under stringent conditions with DNA consisting of a nucleotide sequence complementary to the nucleotide sequence shown in SEQ ID NO:

19 and which encodes a protein having human M-CSF activity.

DNA which is hybridizable under stringent conditions with DNA consisting of a nucleotide sequence complementary to the nucleotide sequence shown in SEQ ID NO: 20 and which encodes a protein having mouse M-CSF activity.

The term "IL-4 activity" is intended to mean the ability to promote Th2 cell differentiation, immunoglobulin class switch, and antibody production in B cells. IL-4 activity can be measured, for example, by immunological procedures such as ELISA, EIA and the like.

The term "M-CSF activity" is intended to mean the ability to promote differentiation and proliferation of monocytes, macrophages and other cells. M-CSF activity can be measured, for example, by immunological procedures such as ELISA, EIA and the like.

Moreover, it is also possible to use DNA which shares a homology of 50% or more, 60% or more, 70% or more, 80% or more, 90% or more, 95% or more, 98% or more, or 99% or more with the nucleotide sequence shown in SEQ ID NO: 17 and which encodes a protein functionally equivalent to the structural protein of human IL-4.

Further, it is also possible to use DNA which shares a homology of 50% or more, 60% or more, 70% or more, 80% or more, 90% or more, 95% or more, 98% or more, or 99% or more with the nucleotide sequence shown in SEQ ID NO: 18 and which encodes a protein functionally equivalent to the structural protein of mouse IL-4.

Furthermore, it is also possible to use DNA which shares a homology of 50% or more, 60% or more, 70% or more, 80% or more, 90% or more, 95% or more, 98% or more, or 99% or more with the nucleotide sequence shown in SEQ ID NO: 19 and which encodes a protein functionally equivalent to the structural protein of human M-CSF.

Furthermore, it is also possible to use DNA which shares a homology of 50% or more, 60% or more, 70% or more, 80% or more, 90% or more, 95% or more, 98% or more, or 99% or more with the nucleotide sequence shown in SEQ ID NO: 20 and which encodes a protein functionally equivalent to the structural protein of mouse M-CSF.

The immunoglobulin Fc (IgFc) sequence to be used in the present invention refers to a C-terminal fragment of the H chain, which is among the fragments obtained by papain digestion of immunoglobulin molecules.

In the present invention, a vector comprising DNA encoding an IgFc sequence allows addition of the IgFc sequence to Aβ to thereby promote intracellular transcription and translation of Aβ. Moreover, such a vector also enhances release of the expressed Aβ into the extracellular environment, so that the immune system can be stimulated more strongly (see FIG. 11).

Examples of IgFc sequences to be used in the present invention include human and mouse IgFc sequences. With respect to the nucleotide sequences of DNAs encoding human and mouse IgFc sequences, GENEBANK® annotated collection of publicly available DNA sequences Accession Nos. BC014258 and XM_484178.3 may be used for human and mouse IgFc sequences, respectively.

SEQ ID NOs of the nucleotide sequences of DNAs encoding human and mouse IgFc sequences to be used in the present invention are shown below.

Human IgFc sequence: SEQ ID NO: 32
Mouse IgFc sequence: SEQ ID NO: 33

The nucleotide sequences shown in SEQ ID NOs: 32 and 33 each have a mutation to replace cysteine residues contained in the original IgFc sequence with serine residues. This is intended to avoid the formation of disulfide linkages.

Moreover, the following DNAs may also be used as DNAs encoding human and mouse IgFc sequences to be used in the present invention.

DNA which is hybridizable under stringent conditions with DNA consisting of a nucleotide sequence complementary to the nucleotide sequence shown in SEQ ID NO: 32 and which encodes a protein having human IgFc activity.

DNA which is hybridizable under stringent conditions with DNA consisting of a nucleotide sequence complementary to the nucleotide sequence shown in SEQ ID NO: 33 and which encodes a protein having mouse IgFc activity.

In the context of the present invention, the term "IgFc activity" is intended to mean the ability to promote intracellular production and extracellular release of Aβ protein. For example, the IgFc activity of a certain protein may be measured as follows: a fusion protein between this protein and Aβ protein is expressed in cultured cells, and an increase in the amount of Aβ protein present in the cultured cells or in the culture supernatant is determined. Quantification of Aβ protein may be accomplished by using immunological procedures such as ELISA, EIA and the like.

Moreover, in the present invention, it is also possible to use DNA which shares a homology of 50% or more, 60% or more, 70% or more, 80% or more, 90% or more, 95% or more, 98% or more, or 99% or more with the nucleotide sequence shown in SEQ ID NO: 32 and which encodes a protein having human IgFc activity.

Further, it is also possible to use DNA which shares a homology of 50% or more, 60% or more, 70% or more, 80% or more, 90% or more, 95% or more, 98% or more, or 99% or more with the nucleotide sequence shown in SEQ ID NO: 33 and which encodes a protein having mouse IgFc activity.

IgFc activity is as defined above.

The above DNAs may be obtained by chemical synthesis or may be obtained from cDNA and genomic libraries by known hybridization techniques (e.g., colony hybridization, plaque hybridization, Southern blotting) using DNA consisting of the nucleotide sequence shown in SEQ ID NO: 1, 3, 5, 7, 9, 11, 13, 15, 17, 18, 19, 20, 32 or 33 or a fragment thereof as a probe.

To construct recombinant vectors, standard genetic engineering procedures may be used.

For example, samples of DNA encoding Aβ of interest, DNA encoding a Th2 cytokine and DNA encoding an IgFc sequence are prepared by PCR or other techniques. PCR may be accomplished in a standard manner by using Taq polymerase or other DNA polymerases. The amplified fragments of interest are digested with restriction enzymes and then inserted into restriction enzyme sites or a multicloning site in a plasmid vector such as PBLUESCRIPT™ (Stratagene). The resulting PCR products are confirmed for their nucleotide sequences with a sequencer to select a plasmid containing the proper sequence. It is preferred that such a DNA sample can be confirmed as an electrophoretically single plasmid.

As a promoter contained in the recombinant vector of the present invention, actin promoter, EF1 promoter, CMV promoter, CAG promoter or the like may be used. These promoters may each be ligated to an appropriate plasmid.

"Stringent conditions" are as defined above. The phrase "having promoter activity" is intended to mean having the ability to transcribe a gene encoding a structural protein or a non-structural protein.

In the vector of the present invention, the above Aβ and Th2 cytokine, and optionally the IgFc sequence are contained in operable form to ensure their expression. Namely, the transgenes (DNAs) are inserted into the vector in a mode which allows expression of the transgenes under the control of appropriate regulatory elements. The DNAs encoding Aβ, Th2 cytokine and IgFc sequence may be separately inserted into different sites in the same vector or may be inserted in tandem. In this context, regulatory elements refer to, for example, promoters, enhancers, transcription terminators and so on.

The vector of the present invention may carry an additional foreign gene at a position different from the region(s) into which the DNAs encoding Aβ, Th2 cytokine and IgFc sequence are inserted. Such a foreign gene may be, for example, but is not limited to, a marker gene for vector monitoring or a regulatory gene for the immune system, such as cytokines and hormones.

Figure 2:
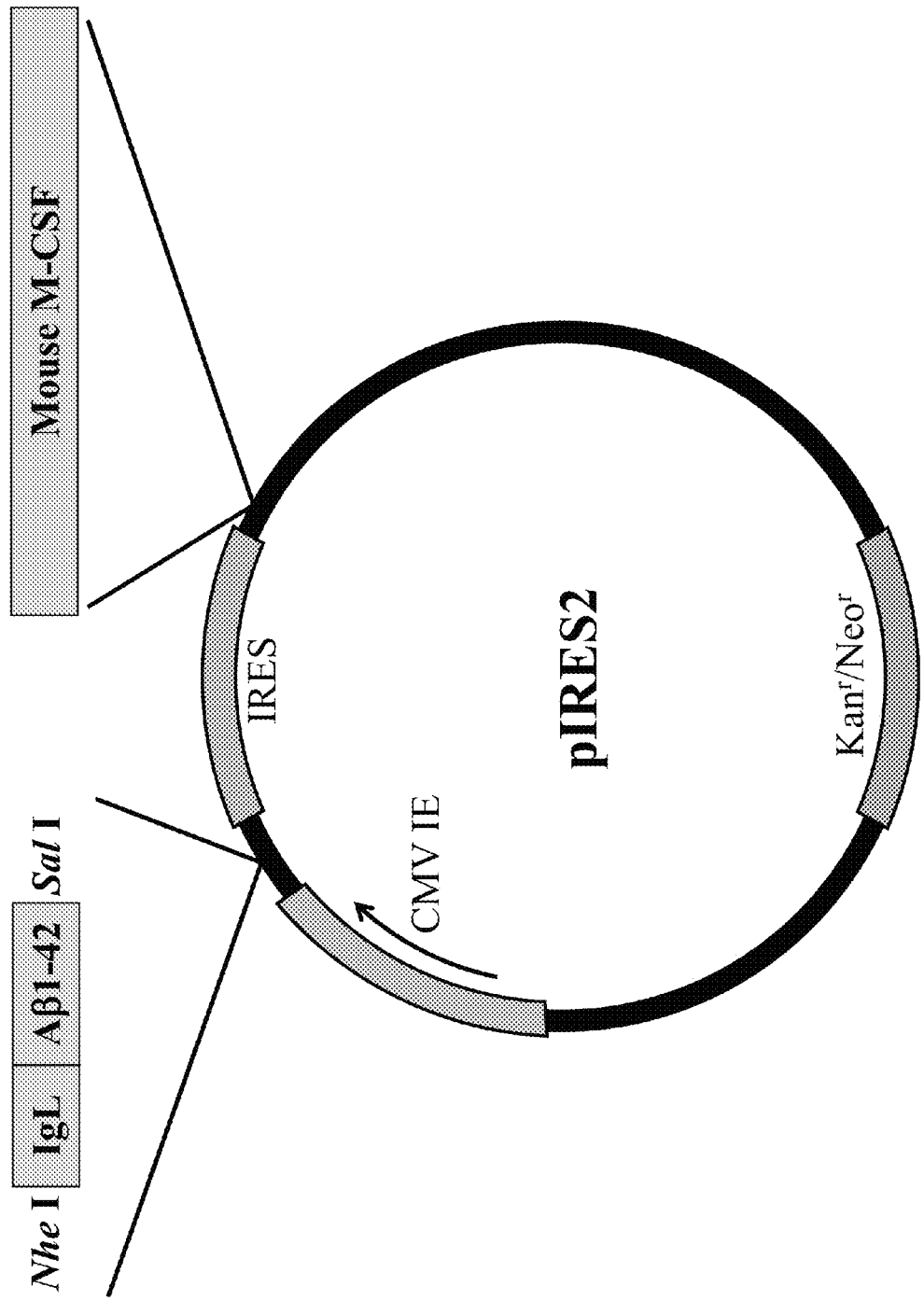
FIG. 2 shows the construction of a vector for use as the DNA vaccine of the present invention.

The vector of the present invention may be exemplified by PTARGET™ Mammalian Expression Vector System in which the Aβ1-42 gene and the IL-4 gene are inserted downstream of the CMV promoter (FIG. 1), as well as pIRES2 in which the Aβ1-42 gene and the M-CSF gene are inserted downstream of the CMV promoter (FIG. 2).

Figure 8:
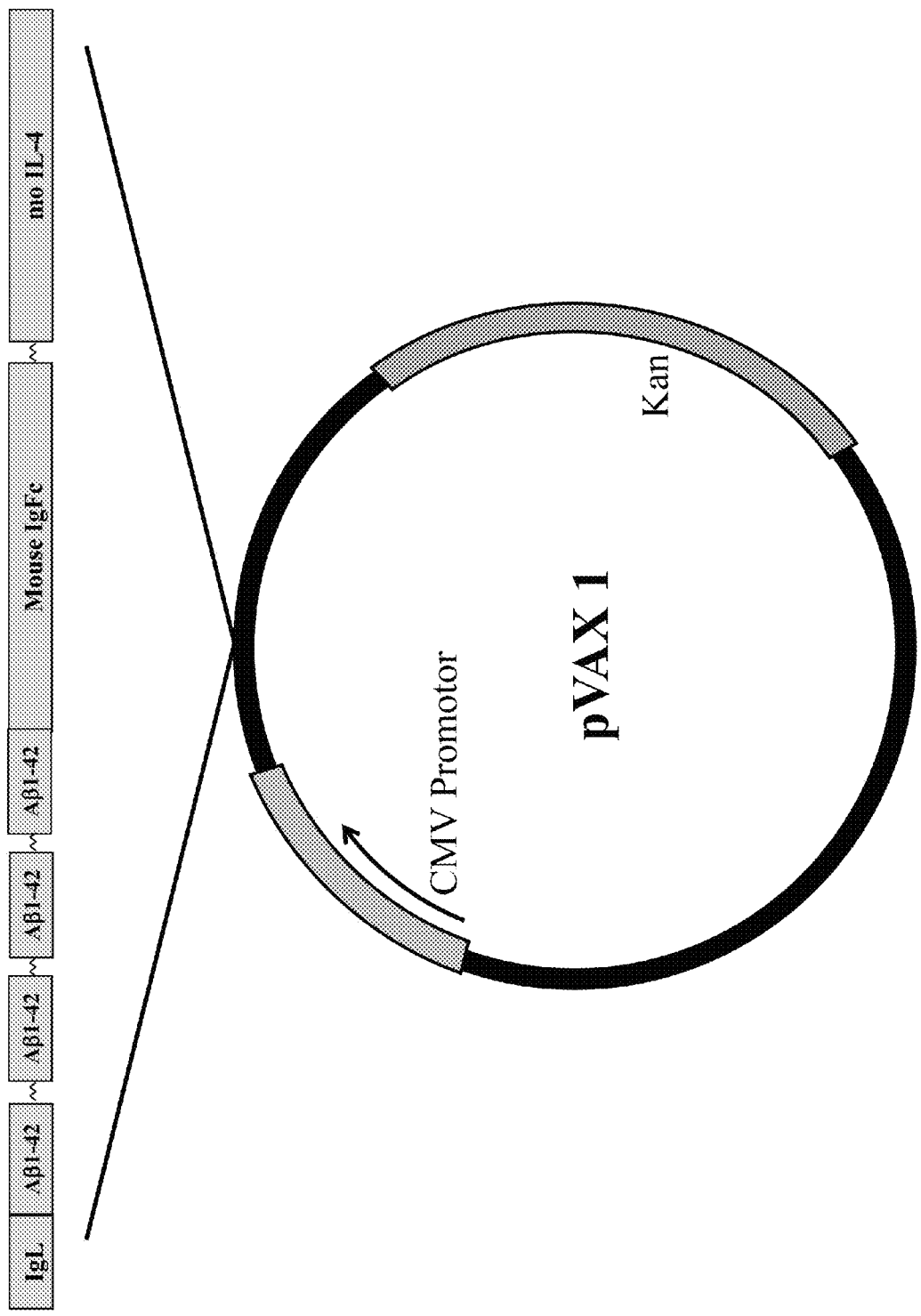
FIG. 8 shows the construction of a vector for use as the DNA vaccine of the present invention.
Figure 9:
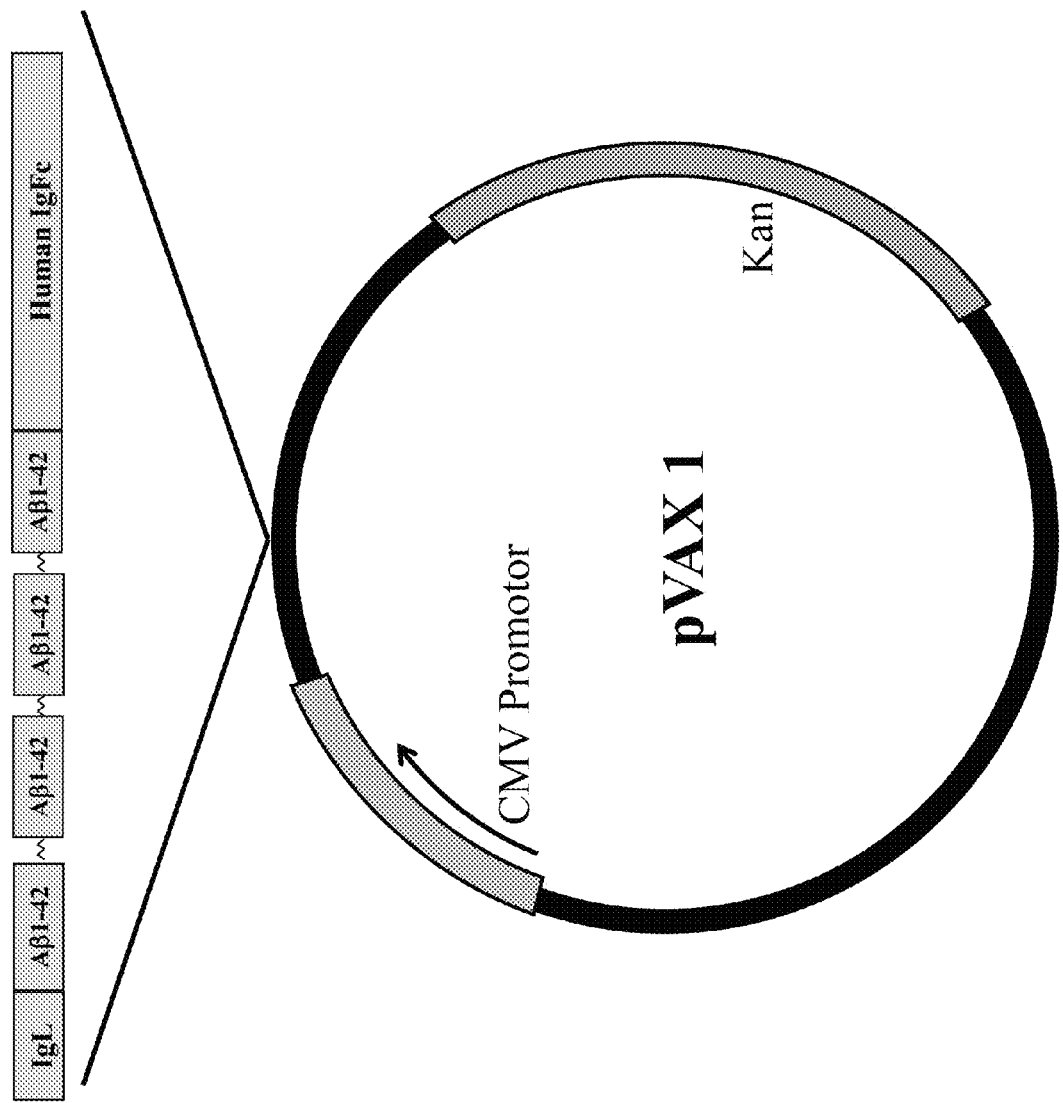
FIG. 9 shows the construction of a vector for use as the DNA vaccine of the present invention.
Figure 10:
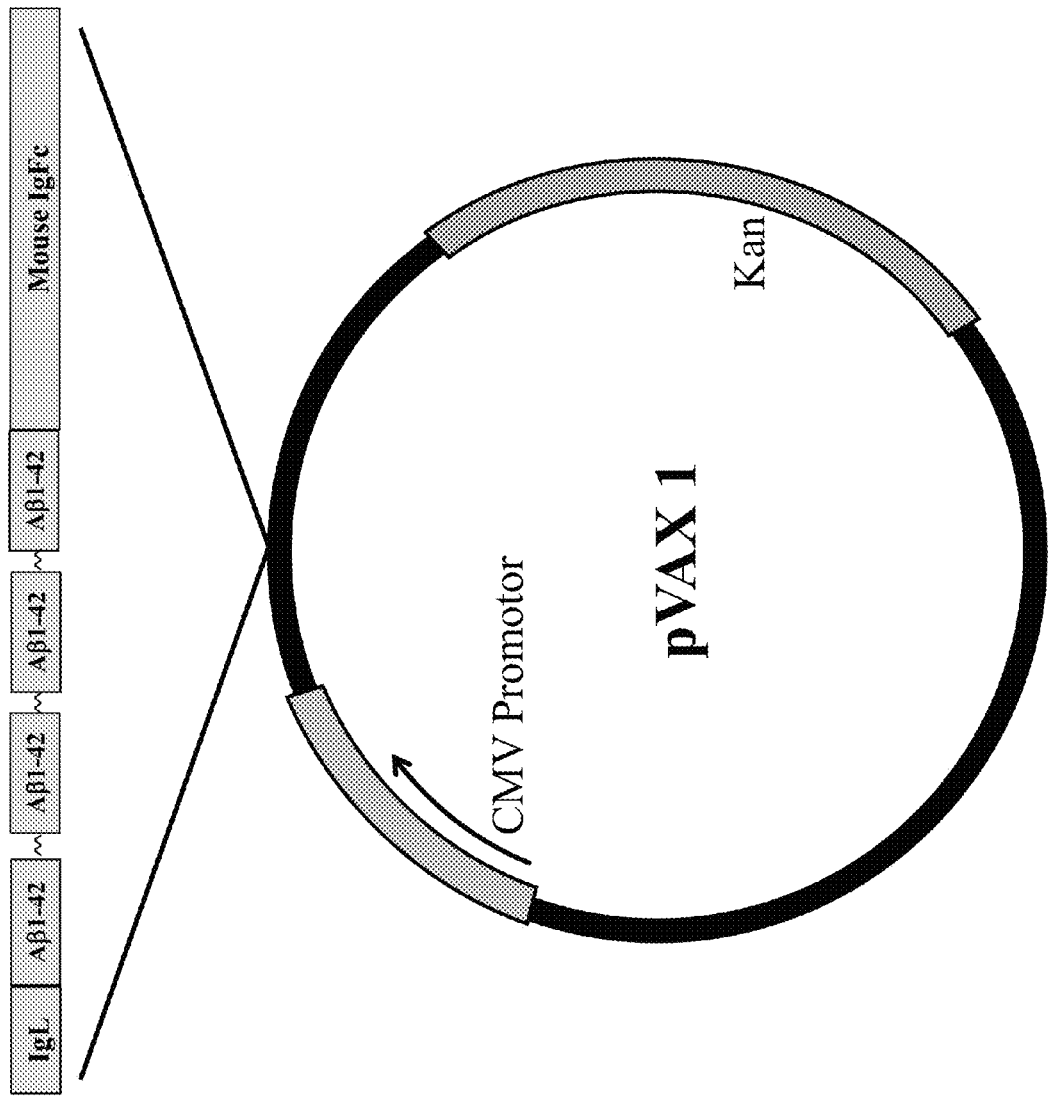
FIG. 10 shows the construction of a vector for use as the DNA vaccine of the present invention.

Moreover, the vector of the present invention may also be exemplified by pVAX1 in which the Aβ1-42 gene, the IgFc gene and the IL-4 gene are inserted downstream of the CMV promoter (FIGS. 5 and 6), pVAX1 in which repeats of the Aβ1-42 gene (DNA), the IgFc gene and the IL-4 gene are inserted downstream of the CMV promoter (FIGS. 7 and 8), as well as pVAX1 in which repeats of the Aβ1-42 gene and the IgFc gene are inserted downstream of the CMV promoter (FIGS. 9 and 10).

PTARGET™ Mammalian Expression Vector System, in which the Aβ1-42 gene and the IL-4 gene are inserted downstream of the CMV promoter, preferably comprises an Ig leader (IgL) sequence upstream of the Aβ1-42 gene and a spacer sequence between the Aβ1-42 gene and the IL-4 gene. More preferably, this PTARGET™ Mammalian Expression Vector System comprises the CMV promoter, the Ig leader sequence, the Aβ1-42 gene, the spacer sequence and the IL-4 gene in this order (FIG. 1).

Figure 5:
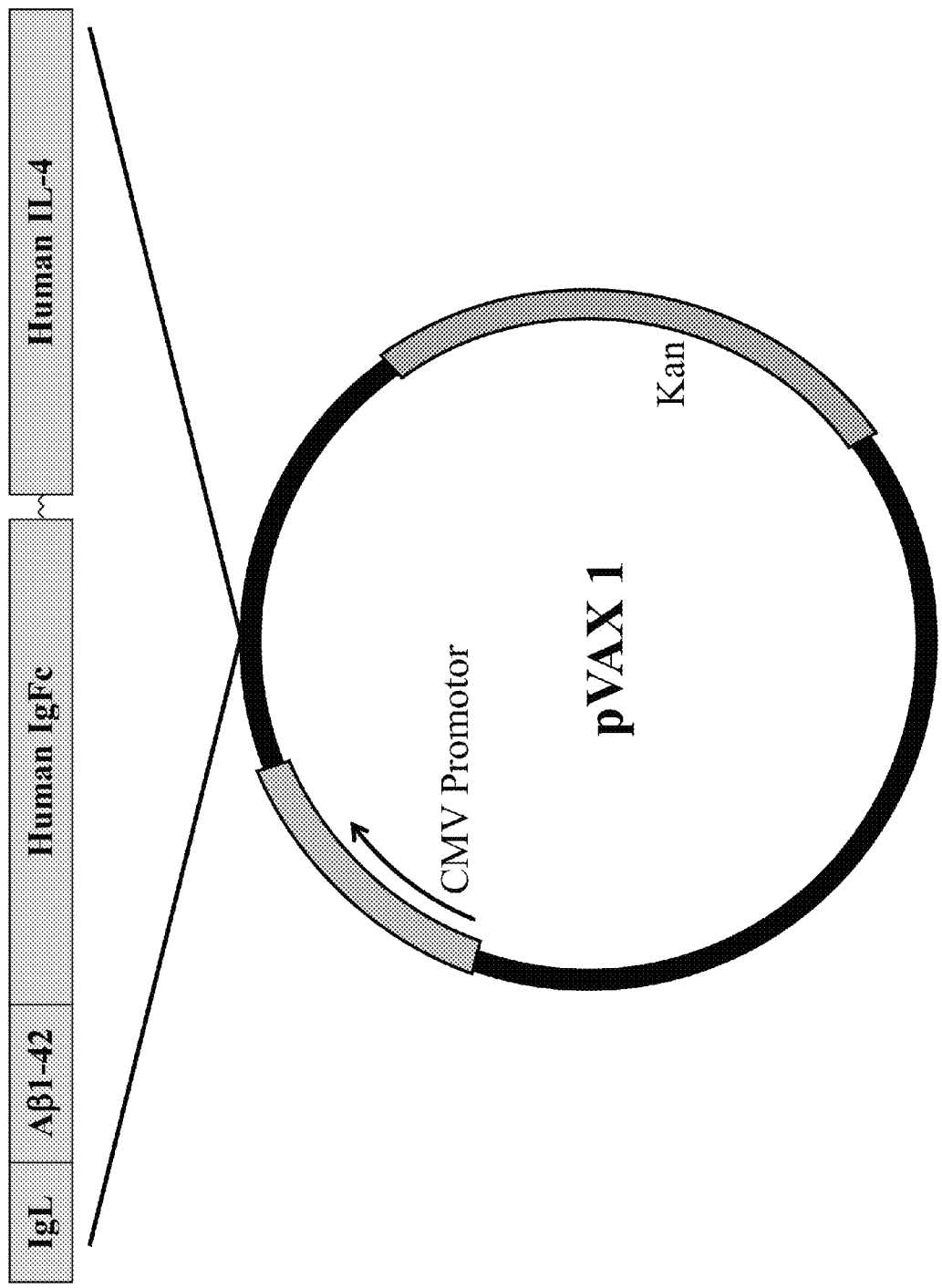
FIG. 5 shows the construction of a vector for use as the DNA vaccine of the present invention.
Figure 6:
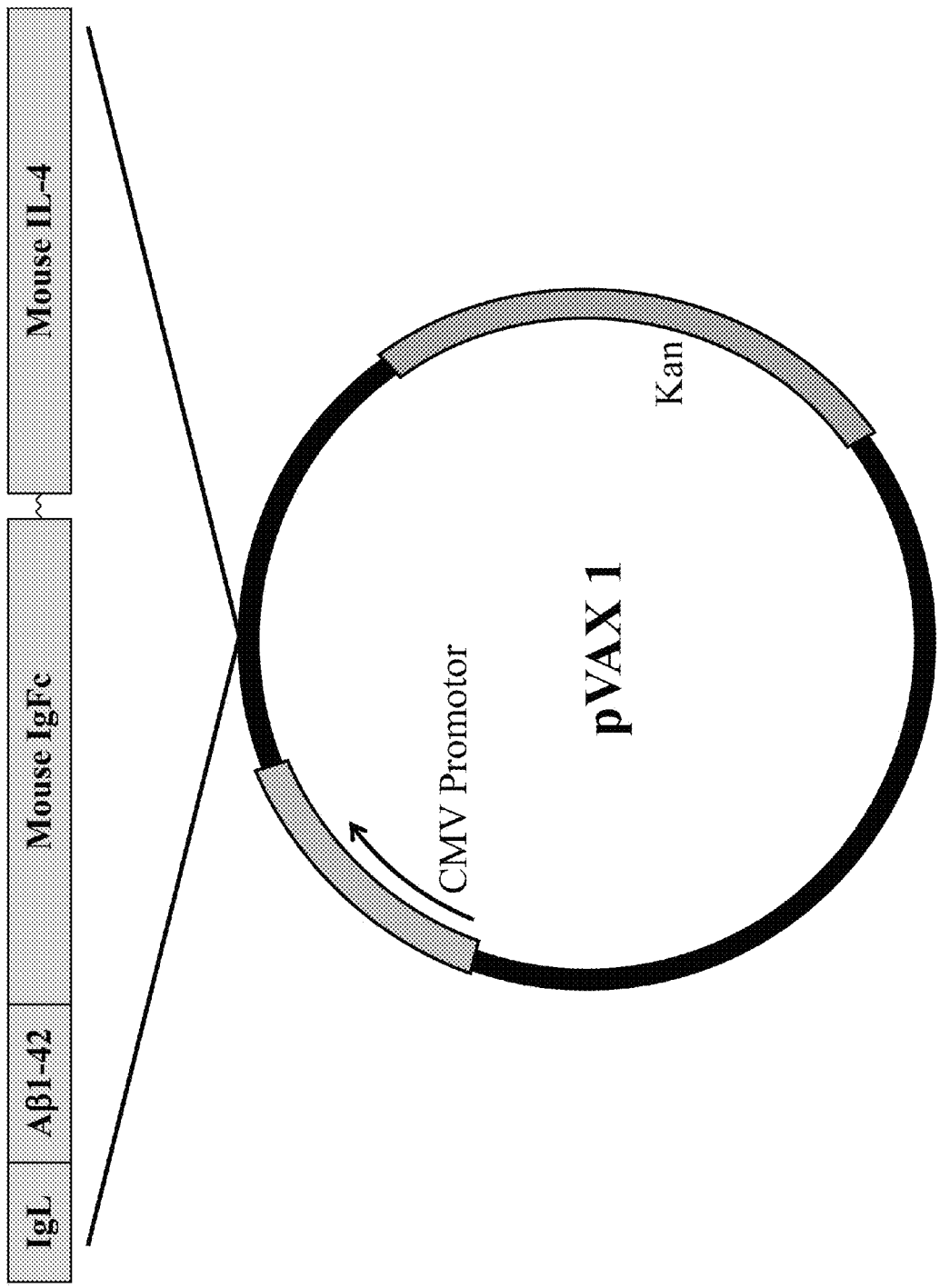
FIG. 6 shows the construction of a vector for use as the DNA vaccine of the present invention.
Figure 7:
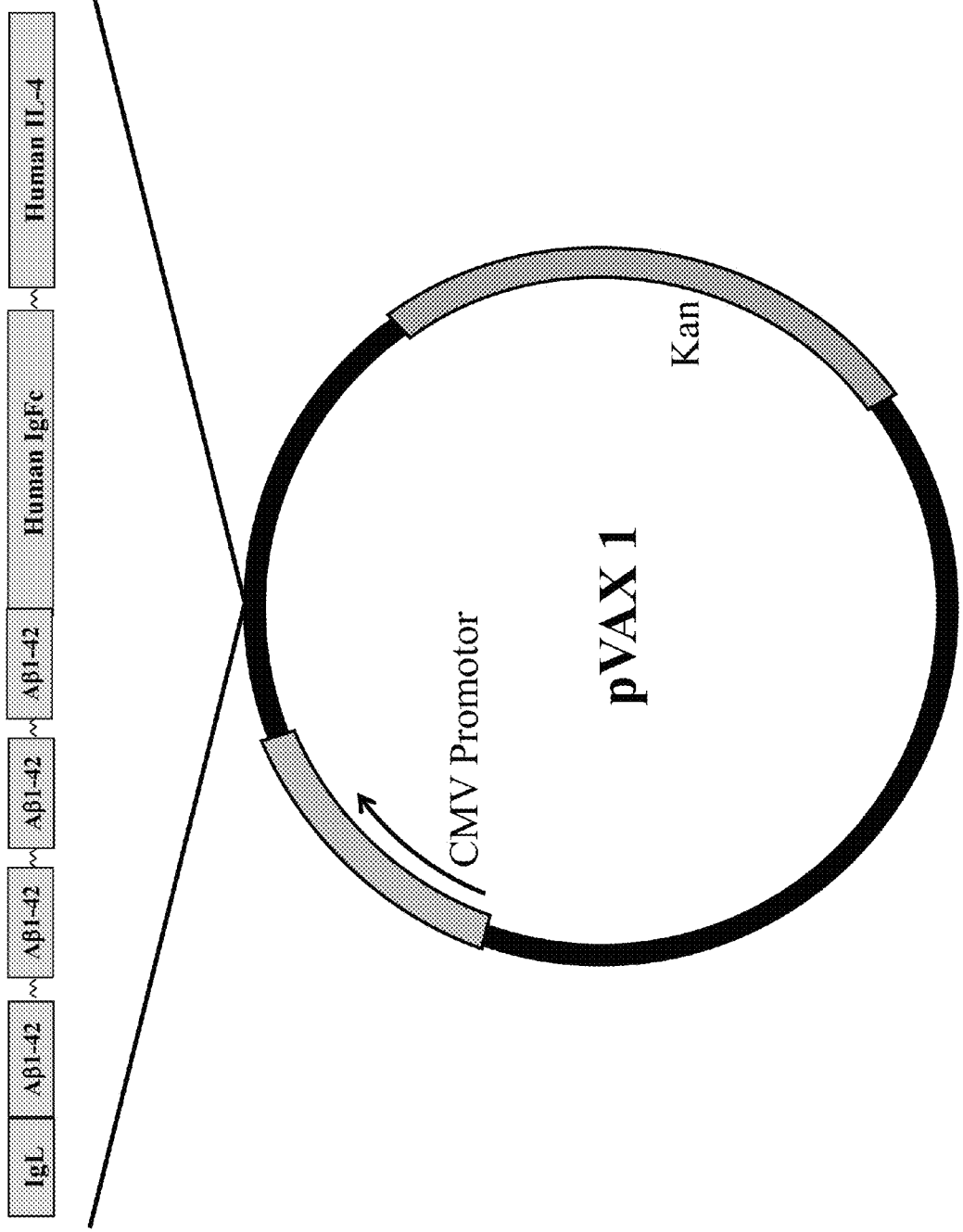
FIG. 7 shows the construction of a vector for use as the DNA vaccine of the present invention.

Likewise, pIRES2, in which the Aβ1-42 gene and the M-CSF gene are inserted downstream of the CMV promoter, preferably comprises an Ig leader sequence upstream of the Aβ1-42 gene and an IRES sequence between the Aβ1-42 gene and the M-CSF gene. More preferably, this pIRES2 comprises the CMV promoter, the Ig leader sequence, the Aβ1-42 gene, the IRES sequence and the M-CSF gene in this order (FIG. 2).

pVAX1, in which the Aβ1-42 gene, the IgFc gene and the IL-4 gene are inserted downstream of the CMV promoter, preferably comprises an Ig leader sequence between the CMV promoter and the Aβ1-42 gene and a spacer sequence between the IgFc gene and the IL-4 gene. More preferably, this pVAX1 comprises the CMV promoter, the Ig leader sequence, the Aβ1-42 gene, the IgFc gene, the spacer sequence and the IL-4 gene in this order (FIGS. 5 and 6).

pVAX1, in which repeats of the Aβ1-42 gene, the IgFc gene and the IL-4 gene are inserted downstream of the CMV promoter, preferably comprises an Ig leader sequence between the CMV promoter and repeats of the Aβ1-42 gene, as well as spacer sequences between the individual Aβ1-42 genes and between the IgFc gene and the IL-4 gene. More preferably, this pVAX1 comprises the CMV promoter, the Ig leader sequence, repeats of the Aβ1-42 gene (containing spacer sequences between the individual Aβ1-42 genes), the IgFc gene, the spacer sequence and the IL-4 gene in this order (FIGS. 7 and 8).

pVAX1, in which repeats of the Aβ1-42 gene and the IgFc gene are inserted downstream of the CMV promoter, preferably comprises an Ig leader sequence between the CMV promoter and repeats of the Aβ1-42 gene, as well as spacer sequences between the individual Aβ1-42 genes. More preferably, this pVAX1 comprises the CMV promoter, the Ig leader sequence, repeats of the Aβ1-42 gene (containing spacer sequences between the individual Aβ1-42 genes) and the IgFc gene in this order (FIGS. 9 and 10).

The above vectors each have genes of mouse or human origin. The vectors having genes of mouse origin can be used in preclinical trials or reagents, while the vectors having genes of human origin can be used in pharmaceutical compositions or reagents.

Namely, the present invention provides a pharmaceutical composition (DNA vaccine) for prevention or treatment of Alzheimer's disease, which comprises the above vector. In another embodiment, the present invention provides a pharmaceutical composition (DNA vaccine) for elimination of brain Aβ, which comprises the above vector. In the context of the present invention, the term "elimination" or "eliminating" is intended to mean reducing the amount of Aβ present in the brain, which encompasses reducing the amount of brain Aβ accumulated, aggregated or deposited in the brain. Moreover, the pharmaceutical composition of the present invention, which comprises the above vector, may also be used as a DNA vaccine for suppressing an increase in brain Aβ levels.

In yet another embodiment, the present invention provides an inducer of anti-Aβ antibody, which comprises the above vector. In still yet another embodiment, the present invention provides an inducer of anti-pEAβ3-42 antibody, anti-ABri antibody or anti-ADan antibody, which comprises the above vector.

pEAβ3-42 is a molecule obtained from Aβ1-42 by N-terminal truncation with gulutaminyl cyclase (QC) and post-translational modification (pyrrole modification). pEAβ3-42 is highly neurotoxic and this molecule itself has a high tendency to aggregate. It also has the ability to enhance the aggregation propensity of unmodified Aβ, and is one of the major factors responsible for lesion development in Alzheimer's disease.

ABri is a causative molecule for familial British dementia, while ADan is a causative molecule for familial Danish dementia. ABri and ADan are molecules which are cleaved as long molecules from their precursor proteins due to a gene mutation in the stop codon region of each precursor protein. ABri and ADan have high amyloid aggregation propensity (amyloid is a generic name for events in which small molecules are aggregated and deposited) and are key molecules in disease progression. Thus, they appear to also play some role in the development of Alzheimer lesions.

In a case where the vector of the present invention is used as a DNA vaccine or as an inducer of anti-Aβ antibody, anti-pEAβ3-42 antibody, anti-ABri antibody or anti-ADan antibody (hereinafter also referred to as "inducers of anti-Aβ antibody and others"), gene transfer may be accomplished either by direct administration in which the vector is directly injected into a target site in the body or by indirect administration in which the vector is infected into patient's own cells or other cells for gene transfer, and the infected cells are then injected into a target site. For direct injection of the vector, intramuscular injection or the like may be used.

Alternatively, the vector of the present invention may also be administered by being introduced into phospholipid vesicles such as liposomes. The vesicles holding the vector of the present invention are introduced by lipofection into certain specific cells. Then, the resulting cells are administered systemically, for example, by the intravenous or intraarterial route. They may be administered locally to the brain, etc.

Examples of lipids used to form liposome structures include phospholipids, cholesterols and nitrogen-containing lipids. Commonly preferred are phospholipids, including natural phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, and lyso-lecithin, as well as hydrogenated products thereof obtained in a standard manner. It is also possible to use synthetic phospholipids such as dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine and so on.

The preparation of liposomes is not limited in any way as long as the resulting liposomes hold DNAs. Liposomes may be prepared in a conventional manner, for example, by reversed-phase evaporation, ether injection, surfactant-based techniques, etc.

Lipids including these phospholipids may be used either alone or in combination. In this case, it is also possible to increase the binding rate of electrically negative DNA when using a lipid whose molecule contains an atomic group having a cationic group (e.g., ethanolamine or choline). In addition to these major phospholipids used for liposome formation, it is also possible to use other additives such as cholesterols, stearyl amine, α-tocopherol and the like, which are generally known as liposome-forming additives. The liposomes thus obtained may further comprise a membrane fusion promoter (e.g., polyethylene glycol) in order to enhance their uptake into cells in the affected area or target tissue.

The vaccine of the present invention or the inducers of anti-Aβ antibody and others according to the present invention may be formulated in a routine manner and may comprise pharmaceutically acceptable carriers. Such carriers may be additives and include water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerine, glycerine, propylene glycol, petrolatum, paraffin, stearyl alcohol, stearic acid, human serum albumin, mannitol, sorbitol, lactose, and surfactants acceptable as pharmaceutical additives, etc.

The above additives may be selected alone or in combination from among those listed above, depending on the dosage form of each therapeutic agent of the present invention. For example, for use as injectable formulations, the purified vector may be dissolved in a solvent (e.g., physiological saline, buffer, glucose solution) and then supplemented with Tween 80, Tween 20, gelatin, human serum albumin or the like. Alternatively, the ingredients may be lyophilized for use as dosage forms that are reconstituted before use. Examples of excipients for lyophilization include sugars such as mannitol, glucose, lactose, sucrose, mannitol and sorbitol; starches such as those derived from corn, wheat, rice, potato and other plants; celluloses such as methylcellulose, hydroxypropylmethylcellulose and carboxymethylcellulose sodium; gums such as gum arabic and gum tragacanth; as well as gelatin, collagen and so on.

In another embodiment, the present invention provides a method for preventing or treating Alzheimer's disease, comprising administrating to a subject an effective amount of the recombinant vector or the DNA vaccine of the present invention.

In another embodiment, the present invention provides a method of eliminating brain Aβ, comprising administrating to a subject an effective amount of the recombinant vector or the DNA vaccine of the present invention.

In another embodiment, the present invention provides a method of inducing anti-Aβ antibody, comprising administrating to a subject an effective amount of the recombinant vector or the DNA vaccine of the present invention.

Subjects to be administered with the DNA vaccine (recombinant vector) of the present invention or with the inducers of anti-Aβ antibody and others according to the present invention include, for example, humans and all other mammals such as non-human primates (e.g., monkeys), rodents (e.g., mice and rats), rabbits, goats, sheep, pigs, cattle and dogs, with humans being more preferred. Animals serving as subjects to be administered may be, for example, those suffering from Alzheimer's disease, those suspected to have Alzheimer's disease, those showing enhanced Aβ deposition, those showing enhanced tau deposition, or those showing neuronal loss.

The dosage (amount) of the DNA vaccine of the present invention or the inducers of anti-Aβ antibody and others according to the present invention will vary depending on the age, sex and symptoms of a patient, the route of administration, the frequency of administration, and the intended dosage form. The mode of administration is selected as appropriate for the age and symptoms of a patient. The effective dosage (amount) of the DNA vaccine is an amount of the vaccine required to reduce the signs or condition of the disease. The therapeutic effect and toxicity of such a DNA vaccine may be determined by standard pharmaceutical procedures in cell culture or in laboratory animals, for example, by ED50 (therapeutically effective dose in 50% of the population) or LD50 (lethal dose for 50% of the population) assay. Likewise, the effective dosage of the inducer of anti-Aβ antibody is an amount of the inducer required to induce detectable levels of anti-Aβ antibody in a biological sample (including blood, cell, tissue, etc.) collected from a patient. Detection of anti-Aβ antibody may be accomplished by immunological procedures such as ELISA, immunostaining and the like. Those skilled in the art would be able to determine an appropriate dosage for the DNA vaccine or the inducer of anti-Aβ antibody.

The route of administration may be selected as appropriate and examples include, but are not limited to, percutaneous, intranasal, transbronchial, intramuscular, intraperitoneal, intravenous and subcutaneous routes. Particularly preferred are intramuscular administration, subcutaneous administration and so on. Inoculation may be made at a single site or at multiple sites.

The dose ratio between therapeutic and toxic effects is a therapeutic index and can be expressed as ED50/LD50. In humans, the single dosage of the vaccine of the present invention or the inducer of anti-Aβ antibody according to the present invention is about 1 μg to 1000 μg, preferably about 10 to 500 μg, more preferably about 50 to 250 μg. The frequency of administration may be once or more as long as side effects are within a clinically acceptable range.

In the previous development of vaccines for Alzheimer's disease, studies have been conducted focusing on anti-Aβ antibody and Th2 activity. Thus, it is desirable to measure, in advance, the antibody titer or cellular immune activity as a vaccine.

For example, the cellular immune activity may be evaluated by isolating and culturing lymphocytes from the body and measuring their $^3$H-thymidine uptake.

Likewise, the Th2 activity may be evaluated by isolating plasma from peripheral blood and measuring its antibody titer by ELISA.

Once the DNA vaccine of the present invention is administered to a subject animal, immune responses against Aβ are induced. Namely, since the above amino acid sequence of Aβ1-43, Aβ1-20, Aβ1-40 or Aβ1-42 contains an epitope, antibody production is induced when the vaccine of the present invention is administered.

Immune responses against Aβ may be detected by measuring the level of anti-Aβ antibody produced. The level of the antibody produced may be measured by standard immunological procedures such as ELISA (enzyme-linked immunosorbent assay). Likewise, the therapeutic effect of the vaccine may be confirmed, for example, as a reduction in the amount of Aβ in brain tissues or as a reduction in Aβ deposition (senile plaques). The amount of Aβ in brain tissues or the state of Aβ deposition may be observed by immunohistochemical or other techniques.

The present invention will be further described in more detail by way of the following illustrative examples, which are not intended to limit the scope of the invention.

Example 1

1. Construction of Plasmid Vector PTARGET™ Mammalian Expression Vector System/Ig-Leader-Aβ1-42-IgFc (1) Amplification and Cloning of IgL, Aβ and Fc Genes To clone the sequences of immunoglobulin K leader (hereinafter referred to as IgL) and immunoglobulin Fc (hereinafter referred to as Fc or IgFc), human peripheral blood mRNA was used as a material to synthesize cDNAs with ReverTra Ace-α-(TOYOBO, Tokyo, Japan). Primers containing the 5'- or 3'-terminal end of each sequence and having an appropriate restriction enzyme site (IgL: BamH I or Xho I; Fc: Kpn I or Not I) were designed and used to amplify human IgL and Fc sequences with KOD-plus-(Toyobo, Tokyo, Japan). Although the original sequence of human Fc contains three codons each encoding a cysteine residue near the 5'-terminal end, these codons were each modified to encode a serine residue (TGT→TCT or TGC→TCC) during primer design so as to avoid S-S linking, and the primers thus designed were used to obtain amplification products.

The sequence of amyloid β1-42 (hereinafter referred to as Aβ) was prepared by oligonucleotide synthesis, provided that two oligonucleotides were first synthesized, which contained the 5'- or 3'-terminal end of the Aβ sequence and were partially complementary to each other (24 by in the middle of the Aβ sequence), because a sequence covering the full length (126 bp) was difficult to synthesize. An appropriate restriction enzyme site (Xho I, Kpn I) was added to each end. After these oligonucleotides were annealed, the entire duplex was prepared by polymerase reaction.

Each product obtained above was inserted into a cloning vector (IgL and Fc: Zero Blunt TOPO PCR Kit for Sequencing, Invitrogen, Tokyo, Japan; Aβ: AdvanTAge PCR Cloning Kit, TAKARA, Tokyo, Japan), followed by sequencing to select a clone having the desired sequence.

(2) Insertion of IgL, Aβ and Fc Sequences into Expression Vector

DNAs of the IgL, Aβ and Fc sequences were excised from the cloning vectors by cleavage at the restriction enzyme sites previously added to each sequence, and then purified from an agarose gel (MINELUTE® Gel Extraction Kit, Qiagen, Tokyo, Japan). Without using the TA cloning site, the PTARGET™ Mammalian Expression Vector System vector was cleaved at two restriction enzyme sites Xho I and Kpn I located upstream and downstream of the TA cloning site to give the same overhangs as those of the Aβ sequence, and then purified from an agarose gel (MINELUTE® Gel Extraction Kit).

First, the PTARGET™ Mammalian Expression Vector System vector and the Aβ sequence were ligated together using a Ligation high kit (Toyobo, Tokyo, Japan) to construct PTARGET™ Mammalian Expression Vector System/Aβ. Subsequently, the region immediately upstream of the Aβ sequence was treated with restriction enzymes BamH I and Xho I for integration of the IgL sequence to thereby construct PTARGET™ Mammalian Expression Vector System/IgL-Aβ. Further, the Kpn I and Not I sites immediately downstream of the Aβ sequence were cleaved for ligation of the Fc sequence to complete PTARGET™ Mammalian Expression Vector System/IgL-Aβ-Fc.

2. Preparation of PTARGET™ Mammalian Expression Vector System/Ig Leader-Amyloid β 1-42-IL-4 (IgL-Aβ-IL-4) Vaccine (1) Amplification of IL-4 Sequence Ig leader-Amyloid β 1-42-IL-4 (IgL-Aβ-IL-4) (FIG. 1) was prepared using PTARGET™ Mammalian Expression Vector System/Ig leader-Amyloid β 1-42-IgFc (IgL-Aβ-Fc) described above. First, human peripheral blood mRNA and mouse spleen mRNA were used to synthesize cDNAs with ReverTra Ace-α-(TOYOBO, Tokyo, Japan). Primers containing the 5'- or 3'-terminal end of human or mouse IL-4 mRNA (coding region) and having an appropriate restriction enzyme site (Kpn I or Not I) were designed and used to amplify the full-length human and mouse IL-4 sequences with KOD-plus-(Toyobo, Tokyo, Japan). PCR products were each purified from an agarose gel (MINELUTE® Gel Extraction Kit, Qiagen, Tokyo, Japan) and inserted into a cloning vector (ZERO BLUNT® TOPO® PCR Kit for Sequencing, Invitrogen, Tokyo, Japan), followed by sequencing to select a clone having the desired sequence. For human IL-4, the sequences of both isotypes 1 (hIL-4) and 2 (hIL-4δ2), which were splice variants, were amplified. However, the latter is a receptor antagonist of IL-4 (Alms W J et al, Mol Immunol 1996, 33:361-370; Fletcher H A et al, Immunology 2004, 112:669-673; Plante S. et al, J Allergy Clin Immunol 2006, 117:1321-1327), and hence isotype 1 was selected.

(2) Recombination to Replace Fc Sequence with IL-4 Sequence

The IL-4 sequence was excised from the cloning vector by cleavage at the previously added restriction enzyme sites (Kpn I, Not I), while the Fc sequence was excised from PTARGET™ Mammalian Expression Vector System/IgL-Aβ-Fc with the same restriction enzyme pair. The hIL-4 or mIL-4 sequence and PTARGET™ Mammalian Expression Vector System/IgL-Aβ were each purified from an agarose gel (MINELUTE® Gel Extraction Kit) and then ligated together overnight at 16° C. using a Ligation high kit (Toyobo, Tokyo, Japan), followed by transformation into TOP10F' (Invitrogen, Tokyo, Japan) and blue-white selection to select a clone carrying the desired sequence (i.e., an insert of the correct size) by restriction enzyme cleavage. The nucleotide sequence of the insert in PTARGET™ Mammalian Expression Vector System/IgL-Aβ1-42-hIL-4 thus obtained is shown in SEQ ID NO: 21, while the nucleotide sequence of the insert in PTARGET™ Mammalian Expression Vector System/IgL-Aβ1-42-mIL-4 thus obtained is shown in SEQ ID NO: 22.

3. Preparation of pIRES2/Ig Leader-Amyloid β 1-42-M-CSF (IgL-Aβ-M-CSF) Vaccine Since M-CSF is a protein that exerts its functions upon homodimer formation, Aβ1-42 and M-CSF were expressed as separate proteins with an IRES system.

(1) Amplification of M-CSF Sequence and Ig Leader (IgL) Sequence

Mouse spleen mRNA was used to synthesize cDNA with ReverTra Ace-α-(TOYOBO, Tokyo, Japan). Primers containing the 5'- or 3'-terminal end of mouse M-CSF (moM-CSF) mRNA (coding region) and having any appropriate restriction enzyme site (BamH I or Not I) were designed and used to amplify the full-length mouse M-CSF sequence with KOD-plus-(Toyobo, Tokyo, Japan). The Ig leader (IgL) sequence was amplified with primers having necessary restriction enzyme sites (Nhe I, Xho I) by using PTARGET™ Mammalian Expression Vector System/Ig leader-Amyloid β 1-42-IgFc (PTARGET™ Mammalian Expression Vector System/IgL-Aβ-Fc) as a template.

The PCR products were each purified from an agarose gel (MINELUTE® Gel Extraction Kit, Qiagen, Tokyo, Japan) and inserted into a cloning vector (ZERO BLUNT® TOPO® PCR Kit for Sequencing, Invitrogen, Tokyo, Japan), followed by sequencing to select a clone having the desired sequence.

(2) Recombination to Replace APL Sequence with IgL Sequence

Based on the previously prepared vector pIRES2-EGFP/Alkaline phosphatase leader-Amyloid β 1-42 (pIRES2-EGFP/APL-Aβ) (pIRES2-EGFP vector: Takara-Chlontech, Tokyo, Japan), pIRES2-EGFP/Ig leader-Amyloid β 1-42 (pIRES2-EGFP/IgL-Aβ) was first prepared. The APL sequence was excised by cleavage at the restriction enzyme sites (Nhe I, Xho I) added to the both ends of this sequence, while the IgL sequence was excised from the cloning vector with the same restriction enzyme pair. pIRES2-EGFP/Aβ and the IgL sequence were each purified from an agarose gel (MINELUTE® Gel Extraction Kit) and then ligated together overnight at 16° C. using a Ligation high kit (Toyobo, Tokyo, Japan), followed by transformation into TOP10 (Invitrogen, Tokyo, Japan) to select a clone carrying the desired sequence (i.e., an insert of the correct size) by restriction enzyme cleavage.

(3) Recombination to Replace EGFP Sequence with M-CSF Sequence

Next, the EGFP sequence was excised from pIRES2-EGFP/IgL-Aβ by cleavage at the restriction enzyme sites (BstX I, Not I), while the M-CSF sequence was excised from the cloning vector by restriction enzyme cleavage (BamH I, Not I). After pIRES2/IgL-Aβ and M-CSF were each purified from an agarose gel, the overhangs of both constructs were blunt-ended with KOD DNA polymerase (Toyobo, Tokyo, Japan). pIRES2/IgL-Aβ was treated with alkaline phosphatase (E. coli alkaline phosphatase, Toyobo, Tokyo, Japan) and then cleaned up (QIAQUICK® PCR Purification Kit, Qiagen, Tokyo, Japan). These two constructs were ligated together using a Ligation high kit (Toyobo, Tokyo, Japan) to complete pIRES2/IgL-Aβ-moM-CSF.

The nucleotide sequence of the insert in pIRES2/IgL-Aβ-moM-CSF thus obtained is shown in SEQ ID NO: 23.

4. Preparation of pVAX1/IgL-Aβ1-42-huIgFc-huIL-4 and pVAX1/IgL-Aβ1-42-mIgFc-mIL-4 Vaccines

(1) Preparation of huIgFc-huIL-4 and mIgFc-mIL-4 Constructs

To amplify huIgFc, PTARGET™ Mammalian Expression Vector System/IgL-Aβ1-42-huIgFc was used as a template for PCR with primers which were designed to have appropriate restriction enzyme sites (Kpn I and Sal I) and to remove the stop codon.

To amplify mIgFc, cDNA derived from mRNA extracted from mouse spleens was used as a template for PCR with primers which were designed to have restriction enzyme sites (Kpn I and Sal I) and to remove the stop codon.

It should be noted that although the original IgFc sequence contains codons each encoding a cysteine residue (Cys), the primers were designed such that seven Cys residues were each replaced with Ser so as to avoid S-S linking.

To amplify huIL-4 and mIL-4, PTARGET™ Mammalian Expression Vector System/IgL-Aβ1-42-huIL-4 and PTARGET™ Mammalian Expression Vector System/IgL-Aβ1-42-mIL-4 were used as templates, respectively, for PCR with primers which were designed to remove their respective leader sequences (signal peptides) and to have a linker sequence (TCTTCTGGTGGTGGTGGT; SEQ ID NO: 24) on the 5'-side. In this case, each construct was amplified such that restriction enzyme sites (Sal I and Not I) were newly added and the stop codon found in the template was maintained.

The amplified gene fragments of huIL-4 and mIL-4 were cleaved at the previously added restriction enzyme sites. Pairs between huIgFc and huIL-4 and between mIgFc and mIL-4 were each ligated using a Ligation high kit (Toyobo, Tokyo, Japan) and cloned (pCR4-Blunt TOPO; Invitrogen, Tokyo, Japan), followed by sequencing to select a clone having the correct sequence of huIgFc-huIL-4 or mIgFc-mIL-4.

(2) Construction of pVAX1/IgL-Aβ1-42-huIgFc-huIL-4 and pVAX1/IgL-Aβ1-42-mIgFc-mIL-4

The huIgFc-huIL-4 or mIgFc-mIL-4 construct was excised by cleavage at the terminal restriction enzyme sites (Kpn I and Not I) and used for recombination with the huIL-4 moiety of PTARGET™ Mammalian Expression Vector System/IgL-Aβ1-42-huIL-4, which had been excised by cleavage at the same sites. As a result, PTARGET™ Mammalian Expression Vector System/IgL-Aβ1-42-huIgFc-huIL-4 and PTARGET™ Mammalian Expression Vector System/IgL-Aβ1-42-mIgFc-mIL-4 were obtained. Further, IgL-Aβ1-42-huIgFc-huIL-4 and IgL-Aβ1-42-mIgFc-mIL-4 were each excised from the PTARGET™ Mammalian Expression Vector System vector by cleavage at the terminal restriction enzyme sites (BamH I and Not I) and then ligated using a Ligation high kit (Toyobo, Tokyo, Japan) to a pVAX1 vector (Invitrogen, Tokyo, Japan) which had been treated with the same restriction enzyme pair, thereby completing pVAX1/IgL-Aβ1-42-huIgFc-huIL-4 and pVAX1/IgL-Aβ1-42-mIgFc-mIL-4 The nucleotide sequences of the inserts in pVAX1/IgL-Aβ1-42-huIgFc-huIL-4 and pVAX1/IgL-Aβ1-42-mIgFc-mIL-4 thus obtained are shown in SEQ ID NOs: 25 and 26, respectively.

5. Preparation of pVAX1/IgL-(Aβ1-42)x4-huIgFc-huIL-4 and pVAX1/IgL-(Aβ1-42)x4-moIgFc-mIL-4 Vaccines A construct carrying 4 repeats of the Aβ1-42 gene ((Aβ1-42)x4) was prepared by linking 4 units of Aβ1-42 via 3 linker sequences (GGTGGCGGTGGCTCG: SEQ ID NO: 27). First, two constructs, i.e., Aβ1-42+linker sequence+Aβ1-6 and Aβ37-42+linker sequence+Aβ1-42 were prepared by PCR amplification. Next, both constructs were mixed together and used as a template for PCR amplification with a sense primer designed to have a restriction enzyme site Xho I on the 5'-side of Aβ1-42 and an antisense primer designed to have a restriction enzyme site Kpn I on the 3'-side of Aβ1-42. The amplification products were electrophoresed on an agarose gel. Among bands in a ladder pattern, a band of about 560 bp corresponding to the molecular weight of (Aβ1-42)x4 was excised and purified.

The (Aβ1-42)x4 construct thus prepared was cloned and sequenced, and then excised by cleavage at the previously added restriction enzyme sites (Xho I and Kpn I) and used for recombination with the Aβ1-42 moiety of PTARGET™ Mammalian Expression Vector System/IgL-Aβ1-42-huIgFc-huIL-4 or PTARGET™ Mammalian Expression Vector System/IgL-Aβ1-42-mIgFc-mIL-4, which had been excised by cleavage at the same sites. As a result, PTARGET™ Mammalian Expression Vector System/IgL-(Aβ1-42)x4-huIgFc-huIL-4 and PTARGET™ Mammalian Expression Vector System/IgL-(Aβ1-42)x4-mIgFc-mIL-4 were obtained. Further, IgL-(Aβ1-42)x4-huIgFc-huIL-4 and IgL-(Aβ1-42)x4-mIgFc-mIL-4 were each excised from the PTARGET™ Mammalian Expression Vector System vector by cleavage at the terminal restriction enzyme sites (BamH I and Not I) and then ligated using a Ligation high kit (Toyobo, Tokyo, Japan) to a pVAX1 vector (Invitrogen, Tokyo, Japan) which had been treated with the same restriction enzyme pair, thereby completing pVAX1/IgL-(Aβ1-42)x4-huIgFc-huIL-4 and pVAX1/IgL-(Aβ1-42)x4-mIgFc-mIL-4 The nucleotide sequences of the inserts in pVAX1/IgL-(Aβ1-42)x4-huIgFc-huIL-4 and pVAX1/IgL-(Aβ1-42)x4-mIgFc-mIL-4 thus obtained are shown in SEQ ID NOs: 28 and 29, respectively.

6. Preparation of pVAX1/IgL-(Aβ1-42)x4-huIgFc and pVAX1/IgL-(Aβ1-42)x4-mIgFc Vaccines To amplify huIgFc and mIgFc each carrying a stop codon, PTARGET™ Mammalian Expression Vector System/IgL-Aβ1-42-huIgFc-huIL-4 and PTARGET™ Mammalian Expression Vector System/IgL-Aβ1-42-mIgFc-mIL-4 were used as templates, respectively, for PCR with primers which were designed to have appropriate restriction enzyme sites (Kpn I and Not I) and a stop codon. The amplification products were each cloned and sequenced, and then excised by cleavage at the restriction enzyme sites (Kpn I and Not I) and used for recombination with the huIgFc-huIL-4 moiety of PTARGET™ Mammalian Expression Vector System/IgL-(Aβ1-42)x4-huIgFc-huIL-4 or with the mIgFc-mIL-4 moiety of PTARGET™ Mammalian Expression Vector System/IgL-(Aβ1-42)x4-mIgFc-mIL-4, which had been excised by cleavage at the same sites. As a result, PTARGET™ Mammalian Expression Vector System/IgL-(Aβ1-42)x4-huIgFc and PTARGET™ Mammalian Expression Vector System/IgL-(Aβ1-42)x4-mIgFc were obtained. Further, IgL-(Aβ1-42)x4-huIgFc and IgL-(Aβ1-42)x4-mIgFc were each excised from the PTARGET™ Mammalian Expression Vector System vector by cleavage at the terminal restriction enzyme sites (BamH I and Not I) and then ligated using a Ligation high kit (Toyobo, Tokyo, Japan) to a pVAX1 vector (Invitrogen, Tokyo, Japan) which had been treated with the same restriction enzyme pair, thereby completing pVAX1/IgL-(Aβ1-42)x4-huIgFc and pVAX1/IgL-(Aβ1-42)x4-mIgFc. The nucleotide sequences of the inserts in pVAX1/IgL-(Aβ1-42)x4-huIgFc and pVAX1/IgL-(Aβ1-42)x4-mIgFc thus obtained are shown in SEQ ID NOs: 30 and 31, respectively.

Example 2

Vaccination Test

1. Vaccination Test with PTARGET™ Mammalian Expression Vector System/IgL-Aβ1-42-mIL-4 and pIRES2/IgL-Aβ1-42-moM-CSF (1) Materials and Methods In the vaccination test, model mice of Alzheimer's disease were used. These model mice were obtained from the Jackson Laboratory, USA. The vaccines used were PTARGET™ Mammalian Expression Vector System/IgL-Aβ1-42-mIL-4 (also referred to as "Aβ-IL4 vaccine"), which was prepared by integrating mouse IL-4 into the plasmid, and pIRES2/IgL-Aβ1-42-moM-CSF (also referred to as "M-CSF vaccine"), which was prepared by integrating mouse M-CSF into the plasmid.

Figure 3:
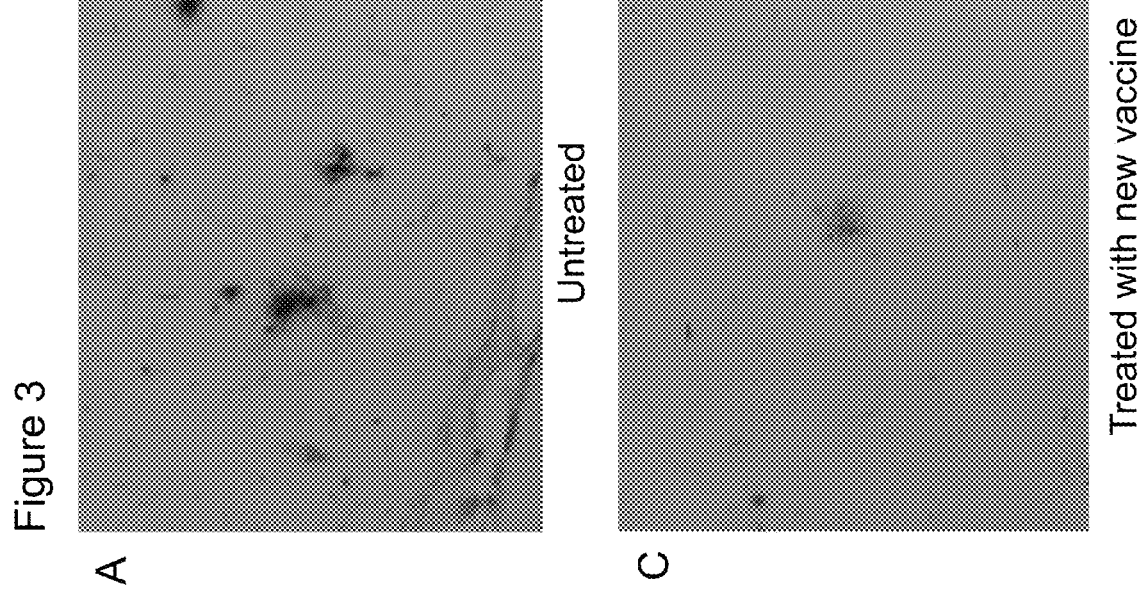
FIG. 3 shows the Aβ-eliminating effect produced by the DNA vaccine of the present invention upon administration to Alzheimer's disease model mice.

The model mice at 4 months of age were vaccinated (100 µg) once per two weeks by intramuscular injection, and the effect of eliminating deposited Aβ was observed at 10 months of age (FIG. 3). First, the mice were sacrificed under deep anesthesia, and their cerebrums were excised and fixed with 4% paraformaldehyde. The fixed brains were dehydrated, embedded in paraffin, and then sliced into thin sections. The sections were deparaffinized and then immunostained with anti-Aβ antibody (FIGS. 3A to 3C). Ten microscopic fields of the brain cortex and hippocampus were randomly photographed from each stained section, and quantified as the total area of Aβ deposition by using NIH image software (FIG. 3D).

The total amount and properties of antibody in the vaccinated animals were analyzed by ELISA and Aβ affinity assay, respectively. ELISA was performed in a standard manner, while the Aβ affinity assay was performed as follows. A test plasma was serially diluted and the resulting respective samples were contacted with cerebral sections of each model mouse to determine the presence or absence of sample binding in an immunohistological manner. The maximum dilution factor giving a positive result was defined as Aβ affinity activity of the sample.

(2) Results

Figure 4:
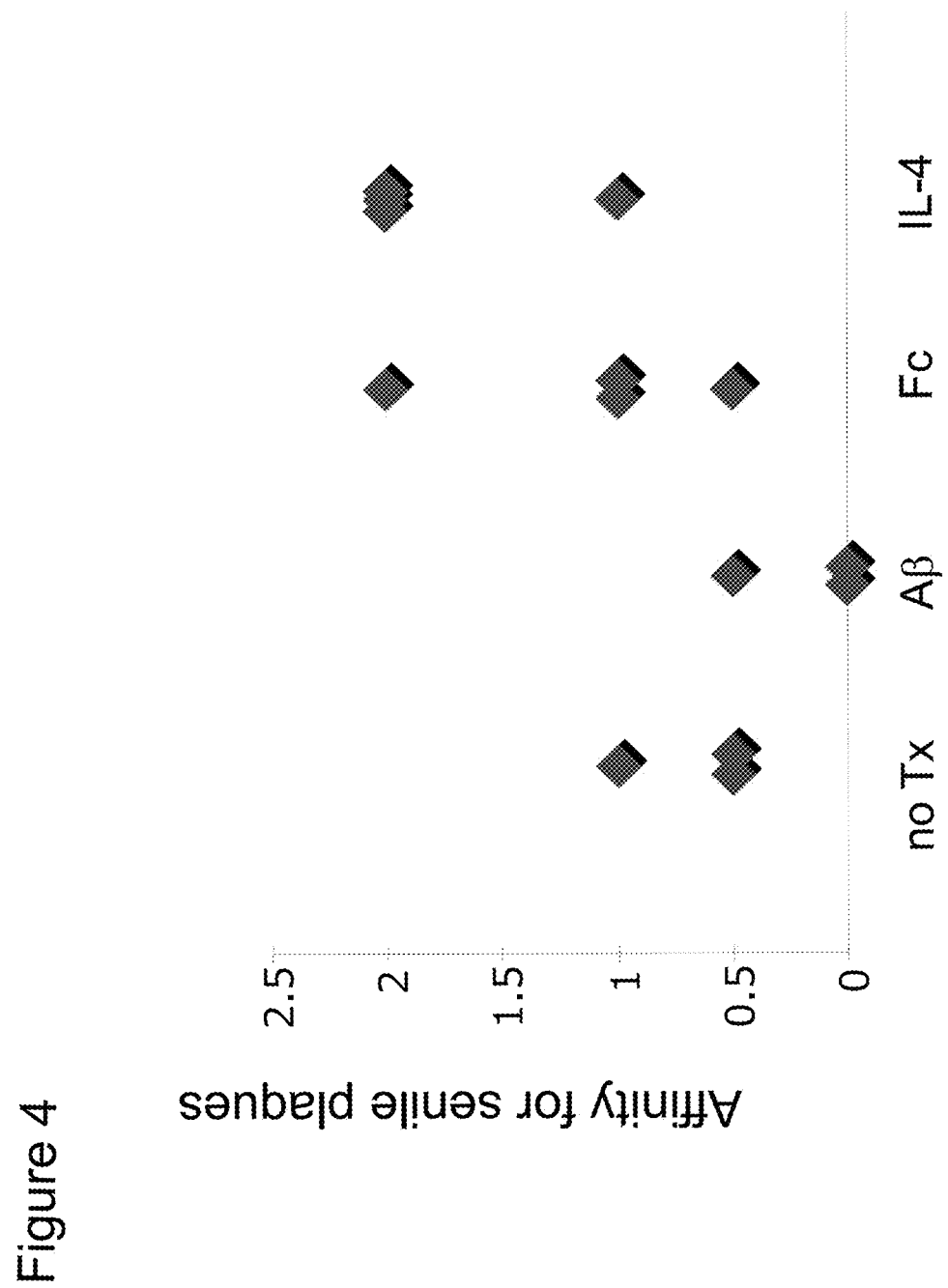
FIG. 4 shows increased levels of antibody with high affinity for Aβ deposition.

The results obtained are shown in FIGS. 3 and 4. In FIGS. 3D and 4, "noTx" represents the untreated group, "Aβ" represents the group receiving Aβ vaccination, and "Fc" represents the group receiving Aβ-Fc vaccination. Likewise, "IL-4" represents the group receiving Aβ-IL4 vaccination, and "MCSF" represents the group receiving M-CSF vaccination.

In FIG. 3, when compared to the untreated group (FIG. 3A), the group receiving existing vaccination (Aβ vaccine, FIG. 3B) shows an Aβ-eliminating effect, which is not so remarkable. In contrast, the new vaccine (Aβ-IL4 vaccine) was clearly found to have a stronger Aβ-eliminating effect (FIG. 3C). These results were quantified and analyzed, indicating that the Aβ-IL4 vaccine had a significantly strong Aβ-eliminating effect, when compared to the existing vaccines (Aβ vaccine, Aβ-Fc vaccine (IgL-Aβ-Fc)) (FIG. 3D). Moreover, the M-CSF vaccine was also found to have a remarkable Aβ-eliminating effect (FIG. 3D).

FIG. 4 indicated that the mice receiving Aβ-IL4 vaccination showed increased levels of antibody with high affinity for Aβ deposition (senile plaques), although there was no significant difference over the control group in their anti-Aβ-IgG levels (FIG. 4). The nature of this induced antibody would support the high Aβ-eliminating effect produced by the new Aβ-IL4 vaccine.

2. Vaccination Test with
pVAX1/IgL-(Aβ1-42)x4-huIgFc-huIL-4 (YM3711)
and Others (1) Materials and Methods pVAX1/IgL-Aβ1-42-huIgFc-huIL-4 (FIG. 5), pVAX1/IgL-Aβ1-42-mIgFc-mIL-4 (FIG. 6), pVAX1/IgL-(Aβ1-42)x4-huIgFc-huIL-4 (FIG. 7), pVAX1/IgL-(Aβ1-42)x4-mIgFc-mIL-4 (FIG. 8), pVAX1/IgL-(Aβ1-42)x4-huIgFc (FIG. 9) and pVAX1/IgL-(Aβ1-42)x4-mIgFc (FIG. 10) were newly constructed and used in the vaccination test.

In the vaccination test, model mice of Alzheimer's disease were used. These model mice were obtained from the Jackson Laboratory, USA.

The vaccines used for mice were pVAX1/IgL-Aβ1-42-mIgFc-mIL-4, pVAX1/IgL-(Aβ1-42)x4-mIgFc-mIL-4 and pVAX1/IgL-(Aβ1-42)x4-mIgFc. The vaccines used for rabbits were pVAX1/IgL-Aβ1-42-huIgFc-huIL-4, pVAX1/IgL-(Aβ1-42)x4-huIgFc-huIL-4 and pVAX1/IgL-(Aβ1-42)x4-huIgFc.

First, the above vaccines were each introduced into cultured cells. The cells were incubated for 3 days and then analyzed by sandwich ELISA to determine the amounts of Aβ present within the cells and in the culture supernatant. The cultured cells used were HEK392 cells.

Next, the model mice at 10 months of age were vaccinated (100 µg) once a week by intramuscular injection, and blood was sampled over time from their orbita. Plasma was separated and analyzed by ELISA to determine the titer of anti-Aβ antibody. In the same manner, rabbits were also vaccinated and measured for antibody titer in their plasma.

The model mice were sacrificed at 12 months of age to study the effect of vaccination on elimination of Aβ deposited in the brain. First, cervical dislocation was performed under deep anesthesia, and cerebrums were excised and fixed with 4% paraformaldehyde. The fixed brains were dehydrated, embedded in paraffin, and then sliced into thin sections. The sections were deparaffinized and then immunostained with anti-Aβ antibody. Ten microscopic fields of the brain cortex were randomly photographed from each stained section, and quantified as the total area of Aβ deposition by using NIH image software.

(2) Results

Figure 11:
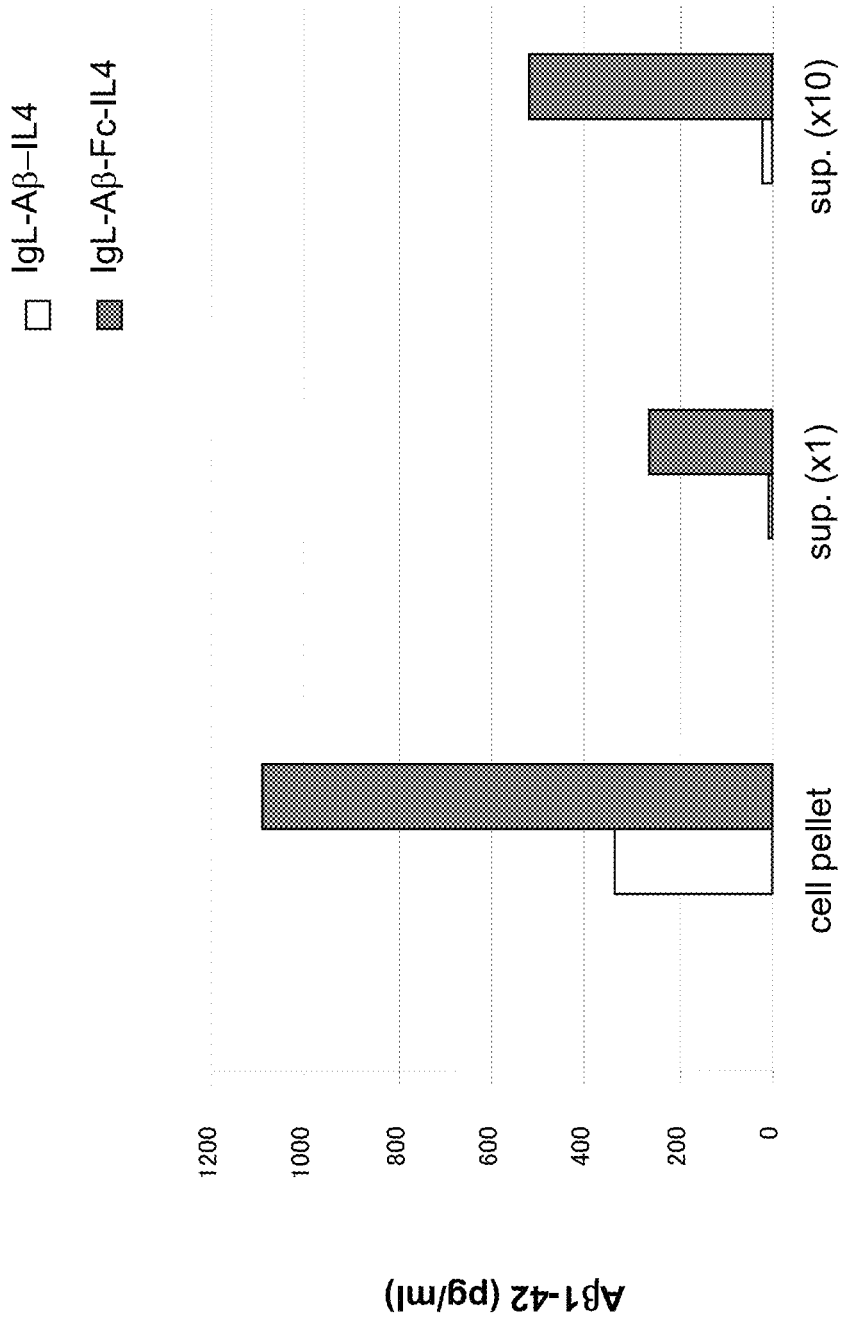
FIG. 11 shows the results obtained for the amount of Aβ produced in cultured cells transfected with the vaccine of the present invention and the amount of Aβ released into the extracellular environment.
Figure 12:
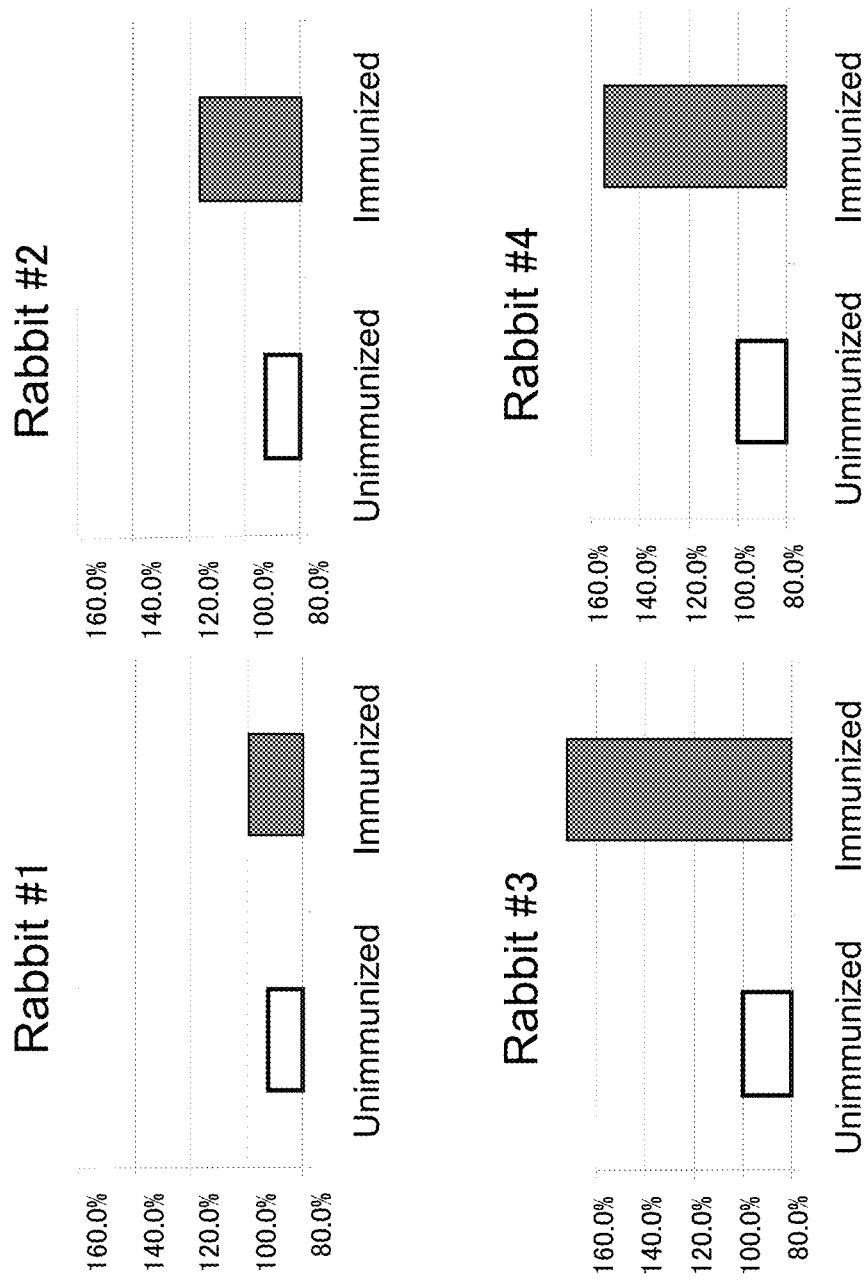
FIG. 12 shows the anti-Aβ antibody-inducing effect in plasma produced by the vaccine of the present invention.
Figure 13:
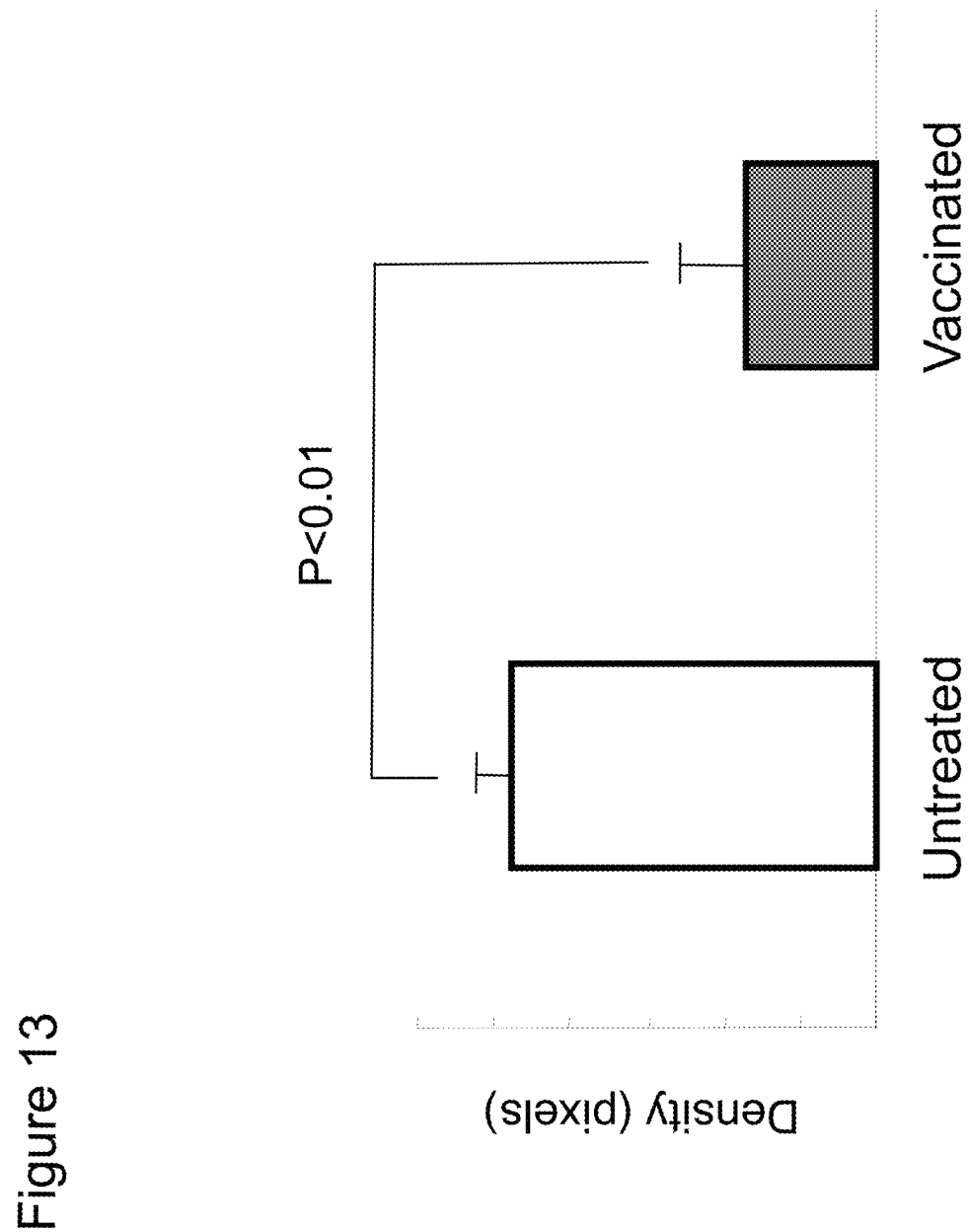
FIG. 13 shows the brain Aβ-eliminating effect produced by the vaccine of the present invention.

The representative results are shown in FIGS. 11 to 13.

In FIG. 11, "IgL-Aβ-IL4" represents pVAX1/IgL-Aβ1-42-mIL-4, and "IgL-Aβ-Fc-IL4" represents pVAX1/IgL-Aβ1-42-mIgFc-mIL-4. Likewise, "cell pellet" represents the cell pellet fraction, and "sup." represents the culture supernatant fraction.

Upon introduction into cultured cells, the vaccine carrying immunoglobulin Fc sequence ("IgL-Aβ-Fc-IL4") showed a several-fold or more increase in Aβ production within the cultured cells ("cell pellet"), when compared to the Fc sequence-free vaccine ("IgL-Aβ-IL4"). Moreover, the Fc sequence-free vaccine caused little Aβ secretion into the culture supernatant, whereas the Fc sequence-carrying vaccine was found to cause remarkable secretion ("sup.").

When rabbits were administered with pVAX1/IgL-Aβ1-42-huIgFc-huIL-4 (hereinafter also referred to as "Aβ(1-42)x1 vaccine") and pVAX1/IgL-(Aβ1-42)x4-huIgFc-huIL-4 (hereinafter also referred to as "YM3711"), not only the Aβ(1-42)x1 vaccine carrying no repeat of Aβ1-42, but also YM3711 carrying repeats of Aβ1-42 caused significant induction of anti-Aβ antibody (FIG. 12). Moreover, the rabbits administered with YM3711 carrying repeats of Aβ1-42 ("Rabbits #3 and #4" in FIG. 12) showed higher antibody titers than the rabbits administered with the Aβ(1-42)x1 vaccine carrying no repeat of Aβ1-42 ("Rabbits #1 and #2" in FIG. 12) (FIG. 12). This result indicates that the vector of the present invention is useful as an inducer of anti-Aβ antibody.

In the quantification of brain Aβ deposition, the mice administered with pVAX1/IgL-(Aβ1-42)x4-mIgFc-mIL-4 clearly showed a remarkable Aβ-eliminating effect, in comparison with the untreated group (FIG. 13).

Until now, some attempts have been made to treat Alzheimer model mice with a vaccine prepared by introducing a gene for Aβ1-42, IL-4 or tissue plasminogen activator into a plasmid vector. However, such a DNA vaccine alone was not sufficient to induce a decrease in brain Aβ levels. This would be because the structure of these vaccines has a defect in the mechanism for elevating anti-Aβ antibody levels. As shown above, the vaccines prepared by the inventors of the present invention were found to be effective by themselves and to produce a higher Aβ-eliminating effect than other existing vaccines. In particular, the human and mouse types of pVAX1/IgL-(Aβ1-42)x4-IgFc-IL-4 vaccines were shown to have an extremely high Aβ-eliminating effect.

Figure 14:
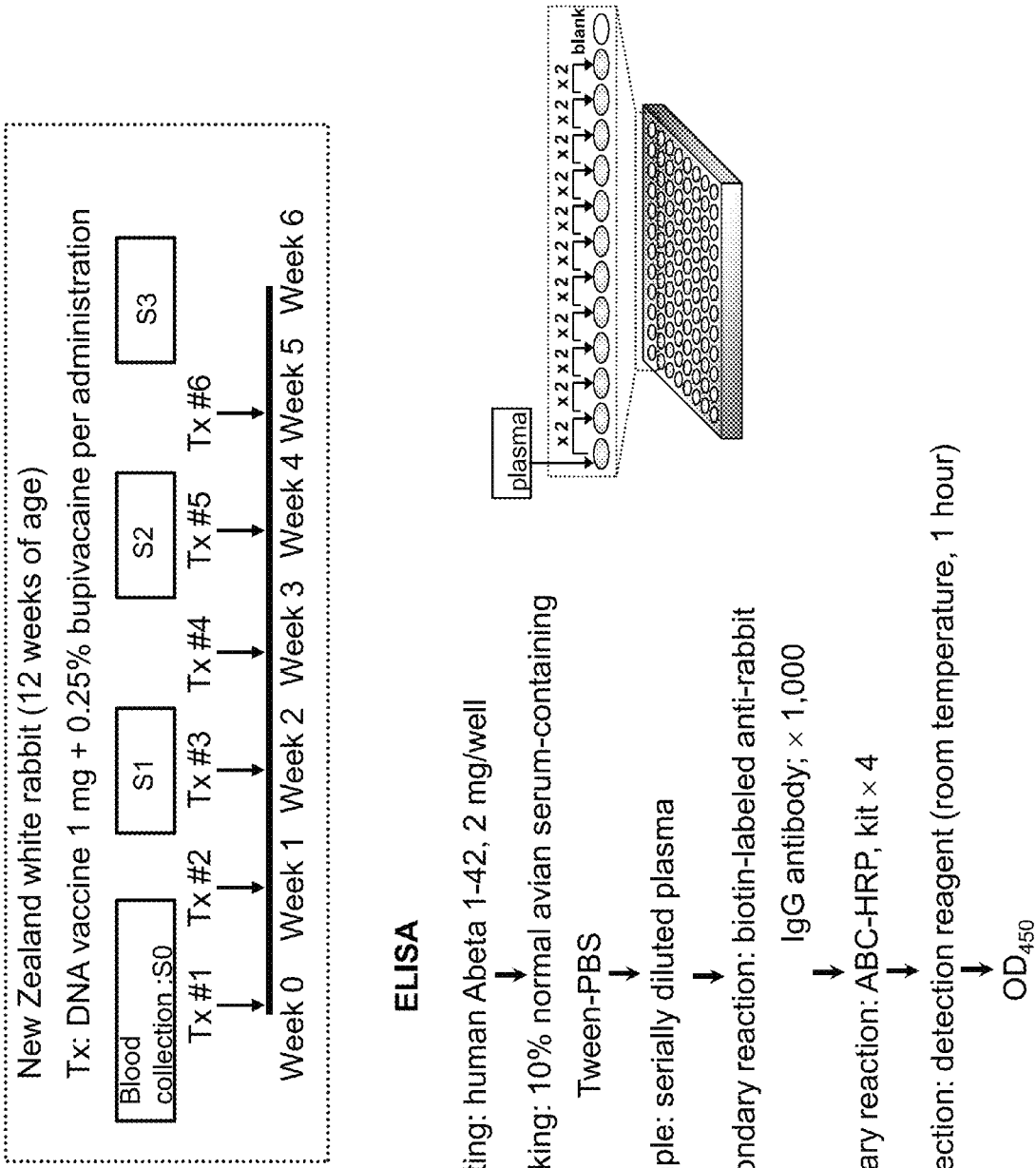
FIG. 14 shows the schedule of DNA vaccination and procedures for antibody titer assay.

3. Study on pVAX1/IgL-(Aβ1-42)x4-huIgFc-huIL-4
(YM3711) for its Ability to Induce Various
Antibodies The inventors of the present invention studied pVAX1/IgL-(Aβ1-42)x4-huIgFc-huIL-4 (YM3711) for its ability to induce various antibodies in the same manner as used in the vaccination test in 2 above. More specifically, rabbits were injected six times (once a week for 6 weeks) with 1 mg of YM3711 by the intramuscular route, and blood was sampled over time. Plasma was separated and analyzed by ELISA to determine the titer of anti-Aβ antibody in the plasma, which was then compared with the unimmunized plasma. The same test was also repeated using an existing vaccine (pVAX1/IgL-Aβ1-42-huIgFc), and the degree of antibody titer in this case was compared with that of YM3711. FIG. 14 shows the schedule of DNA vaccination and procedures for antibody titer assay in rabbits.

Figure 15:
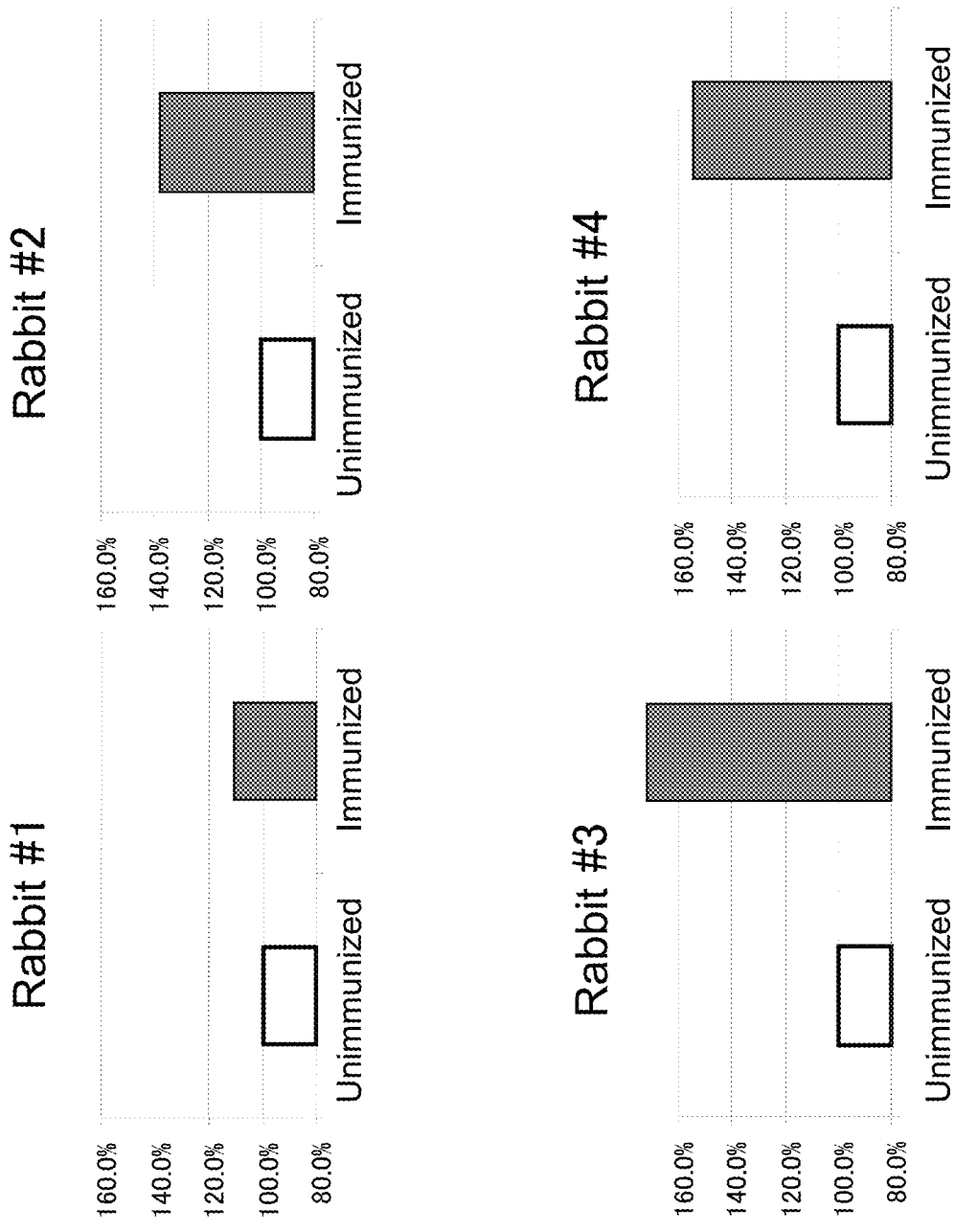
FIG. 15 shows the anti-Aβ1-42 antibody-inducing effect produced by YM3711 in rabbits.

As a result, the rabbits administered with YM3711 ("Rabbits #3 and #4" in FIG. 15) were found to show a higher increase in the antibody titer of anti-Aβ1-42 antibody than the rabbits administered with the existing vaccine ("Rabbits #1 and #2" in FIG. 15) (FIG. 15). Table 1 below shows the % increase in antibody titer after immunization with YM3711.

[Table 1]

TABLE 1

Increase (%) in antibody titer after immunization
Anti-Aβ1-42 antibody (%)

|  | Rabbit #1 | Rabbit #2 |
| --- | --- | --- |
| Existing vaccine | 12 | 39 |
|  | Rabbit #3 | Rabbit #4 |
| YM3711 | 68 | 58 |

As shown in Table 1, the rabbits administered with the existing vaccine ("Rabbits #1 and #2" in Table 1) showed an increase of 12% to 39% when compared to before immunization. In contrast, the rabbits administered with YM3711 ("Rabbits #3 and #4" in Table 1) showed an increase as high as 58% to 68%. This indicates that YM3711 causes remarkable induction of anti-Aβ1-42 antibody in rabbits, in comparison with the existing vaccine.

Figure 16:
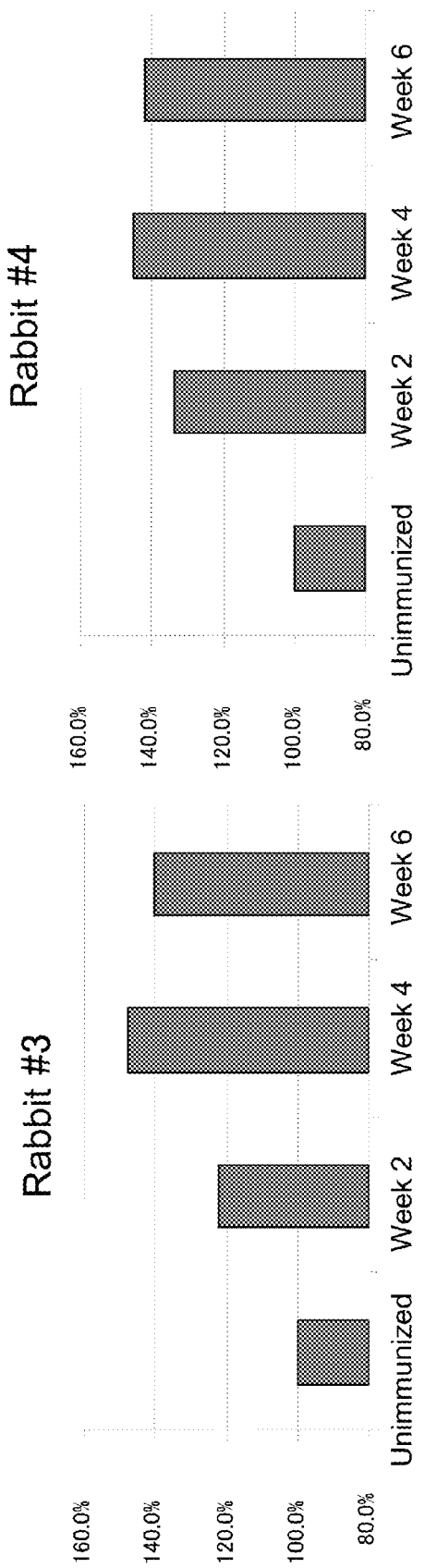
FIG. 16 shows the time course of anti-Aβ1-42 antibody induction mediated by YM3711 in rabbits.
Figure 17:
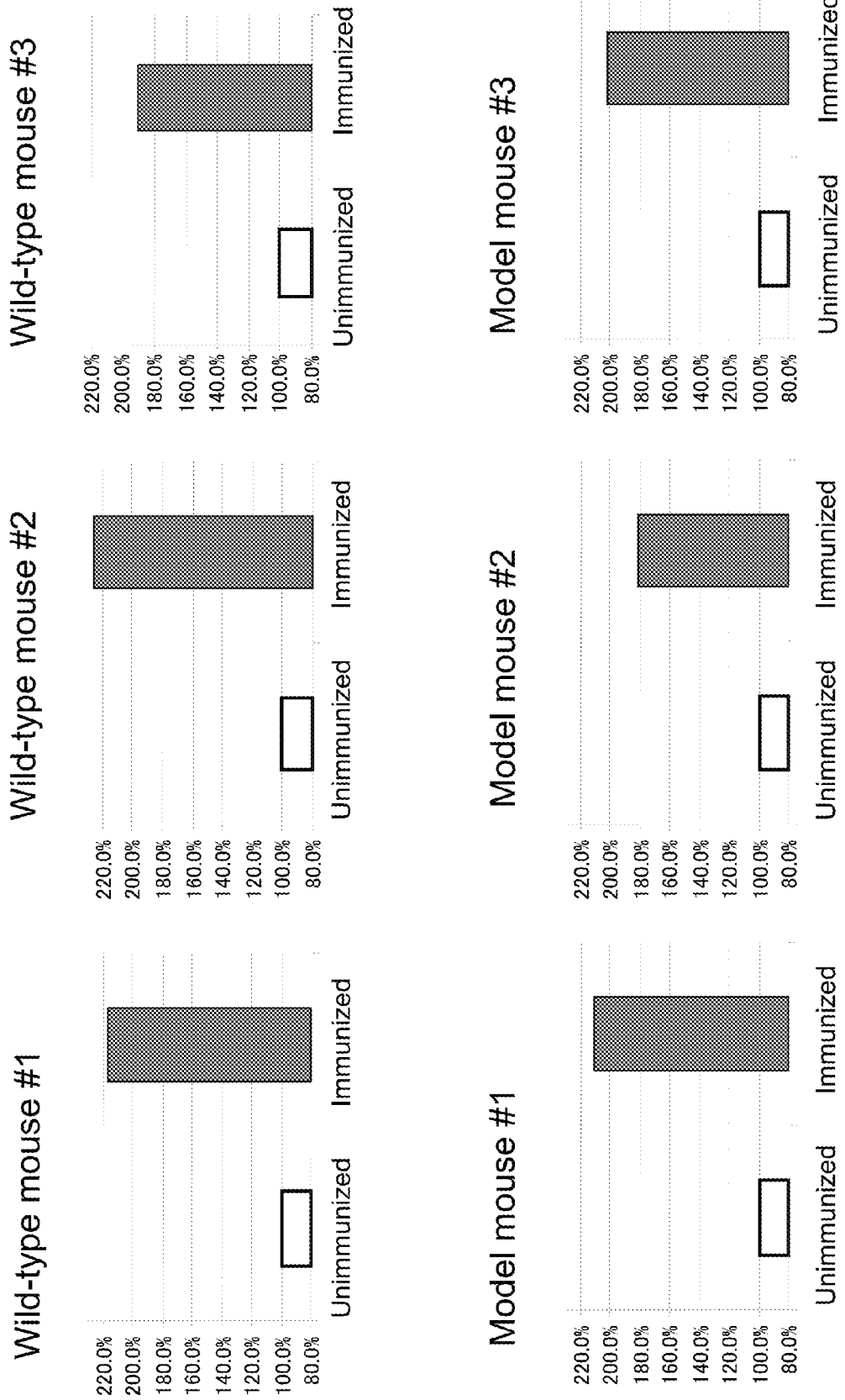
FIG. 17 shows the anti-Aβ1-42 antibody-inducing effect produced by YM3711 in wild-type mice and in disease model mice.

The antibody titer of anti-Aβ1-42 antibody started to increase at 2 weeks after immunization and was then maintained at a high level (FIG. 16). Moreover, not only the rabbits, but also wild-type or model mice showed an increase in antibody titer upon DNA vaccination (FIG. 17). Table 2 below shows the % increase in antibody titer after wild-type and model mice were each immunized with YM3711.

[Table 2]

TABLE 2

Anti-Aβ antibody-inducing effect of YM3711 in mice

| | #1 | #2 | #3 (%) |
|---|---|---|---|
| Wild-type mouse | 119 | 124 | 91 |
| Model mouse | 111 | 81 | 100 |

As shown in Table 2, YM3711 was found to cause an increase of 91% to 124% in the wild-type mice and 81% to 111% in the model mice. This indicates that YM3711 also causes remarkable induction of anti-Aβ1-42 antibody in both wild-type and model mice.

The inventors of the present invention further conducted the same test in monkeys, which are most important in drug development. More specifically, male cynomolgus monkeys at 3.5 to 4.5 years of age (3.0 to 4.0 kg) were injected with 0.5 mg/kg of YM3711 once a week by the intramuscular route, and blood was collected before immunization and after 2 and 4 weeks. Plasma fractions of these blood samples were used in ELISA using the Aβ1-42 peptide as an antigen to determine their anti-Aβ antibody titer. In this test, the antibody titer before immunization was set to 100%, and % elevation (% increase) of antibody titer was calculated for each animal.

Figure 18:
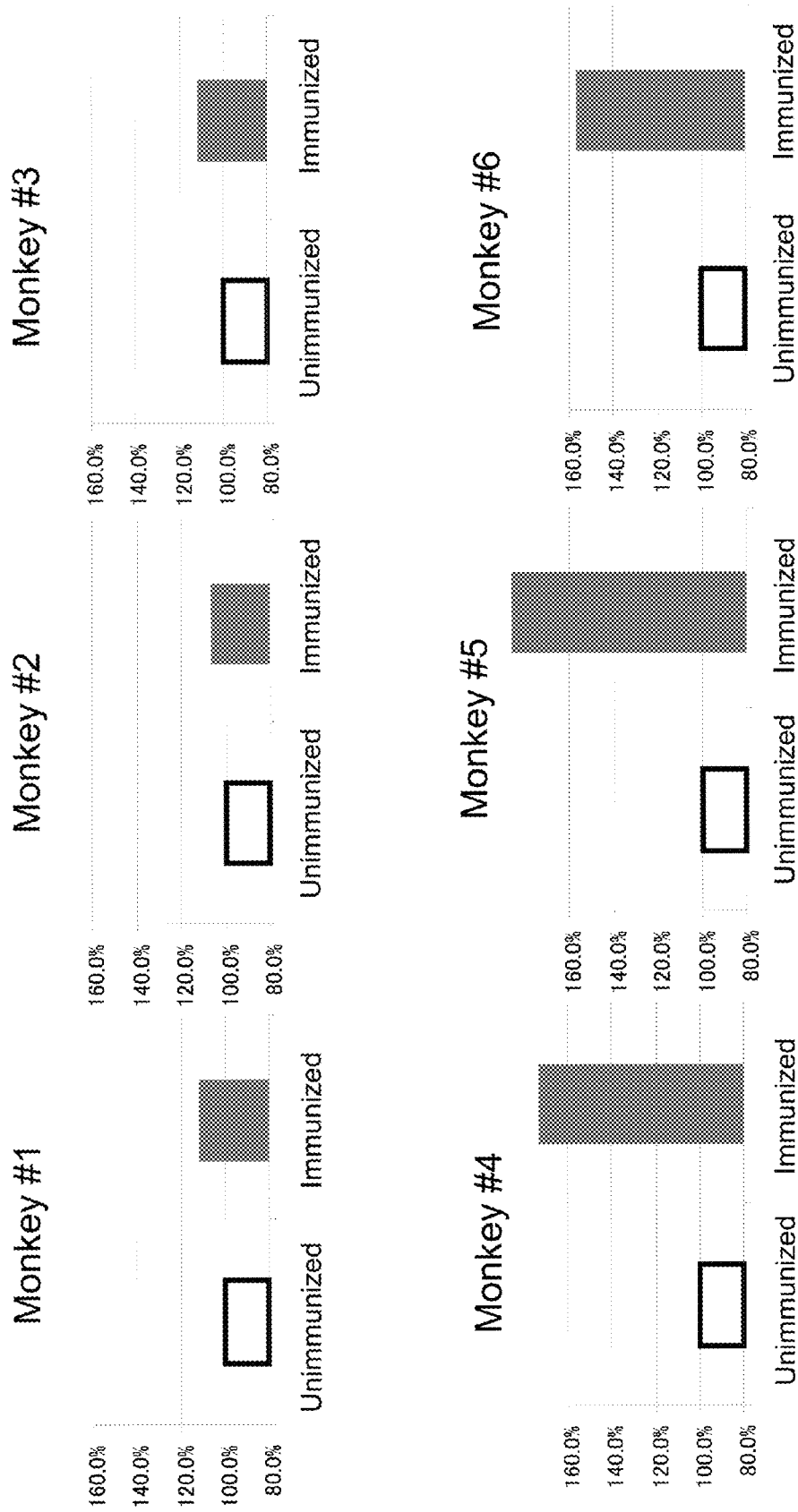
FIG. 18 shows the anti-Aβ1-42 antibody-inducing effect produced by YM3711 in monkeys.

As a result, the monkeys administered with YM3711 ("Monkeys #4 to #6" in FIG. 18) were found to show a remarkably higher increase in the antibody titer of anti-Aβ1-42 antibody than the monkeys administered with the existing vaccine (pVAX1/IgL-Aβ1-42-huIgFc) ("Monkeys #1 to #3" in FIG. 18) (FIG. 18). Table 3 below shows the % increase in antibody titer after immunization with YM3711.

[Table 3]

TABLE 3

Increase (%) in antibody titer after immunization
Anti-Aβ1-42 antibody (%)

| | Monkey #1 | Monkey #2 | Monkey #3 |
|---|---|---|---|
| Existing vaccine | 12 | 8 | 12 |
| | Monkey #4 | Monkey #5 | Monkey #6 |
| YM3711 | 75 | 81 | 58 |

As shown in Table 3, the monkeys administered with the existing vaccine ("Monkeys #1 to #3" in Table 3) showed an increase of 8% to 12% when compared to before immunization. In contrast, the monkeys administered with YM3711 ("Monkeys #4 to #6" in Table 3) showed an increase as high as 58% to 81%. This indicates that YM3711 causes remarkable induction of anti-Aβ1-42 antibody in monkeys, in comparison with the existing vaccine.

Moreover, in comparison with the test in rabbits (FIG. 15 and Table 1), the monkeys showed a remarkable difference between the increase in antibody titer after immunization with the existing vaccine and the increase in antibody titer after immunization with YM3711. This indicates that YM3711 is a vaccine or an inducer of anti-Aβ1-42 antibody, which is more compatible than the existing vaccine with animals closer to humans.

Figure 19:
FIG. 19 shows the time course of anti-Aβ1-42 antibody induction in monkeys after immunization with YM3711.

In the monkeys, the antibody titer of anti-Aβ1-42 antibody started to increase at 2 weeks after immunization and was then maintained at a high level, which indicated a sufficient increase in anti-Aβ antibody levels until 4 weeks after immunization (FIG. 19).

Moreover, to study the ability of YM3711 to induce various antibodies, the same procedure as used above in antibody titer assay for anti-Aβ1-42 antibody was repeated to determine the antibody titers of other antibodies, i.e., antibody against pEAβ3-42 having strong neurotoxicity, as well as antibodies against ABri and ADan having high amyloid aggregation propensity although their amino acid sequences are completely different from that of Aβ. Antibody titer assay was performed with rabbits and monkeys.

Figure 20:
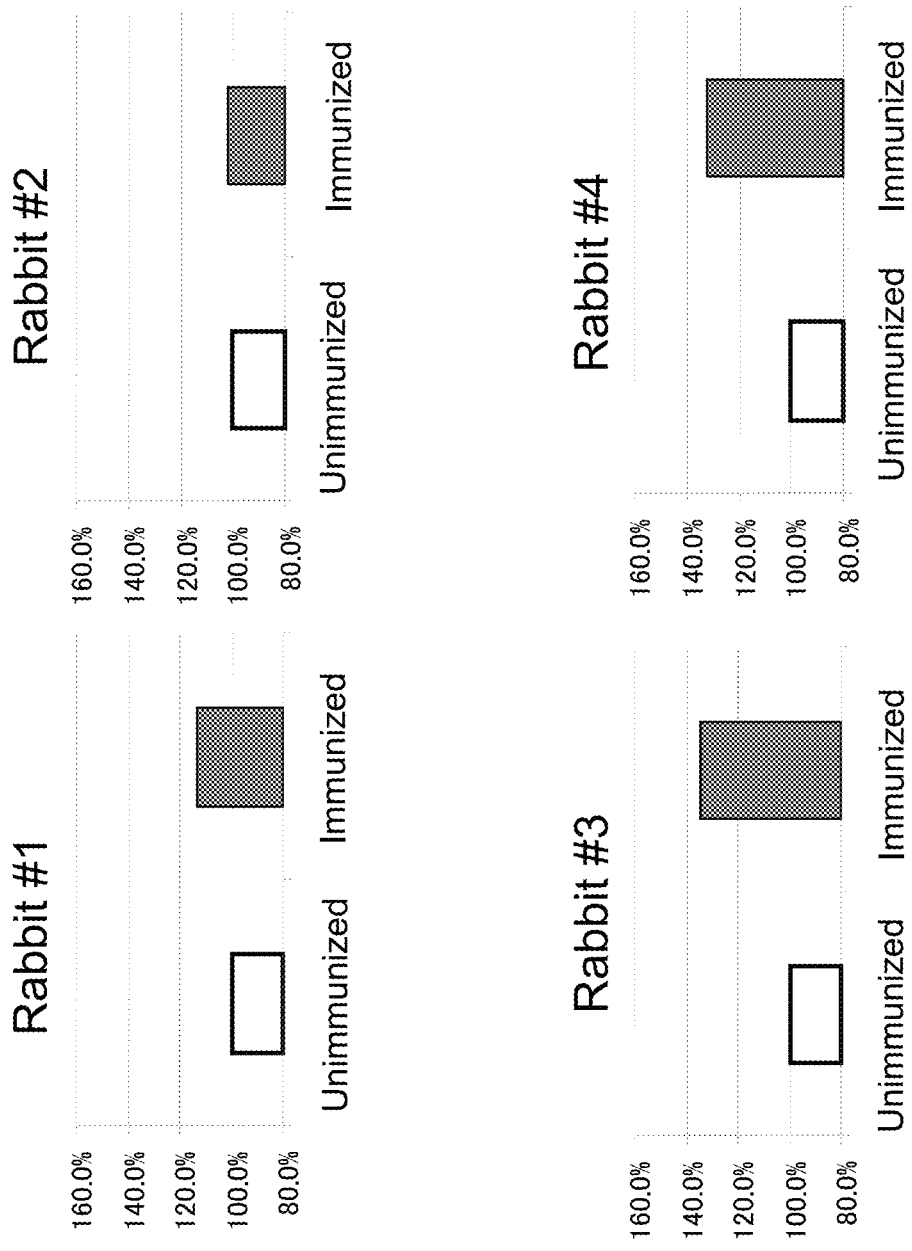
FIG. 20 shows the anti-pEAb3-42 antibody-inducing effect produced by YM3711 in rabbits.
Figure 21:
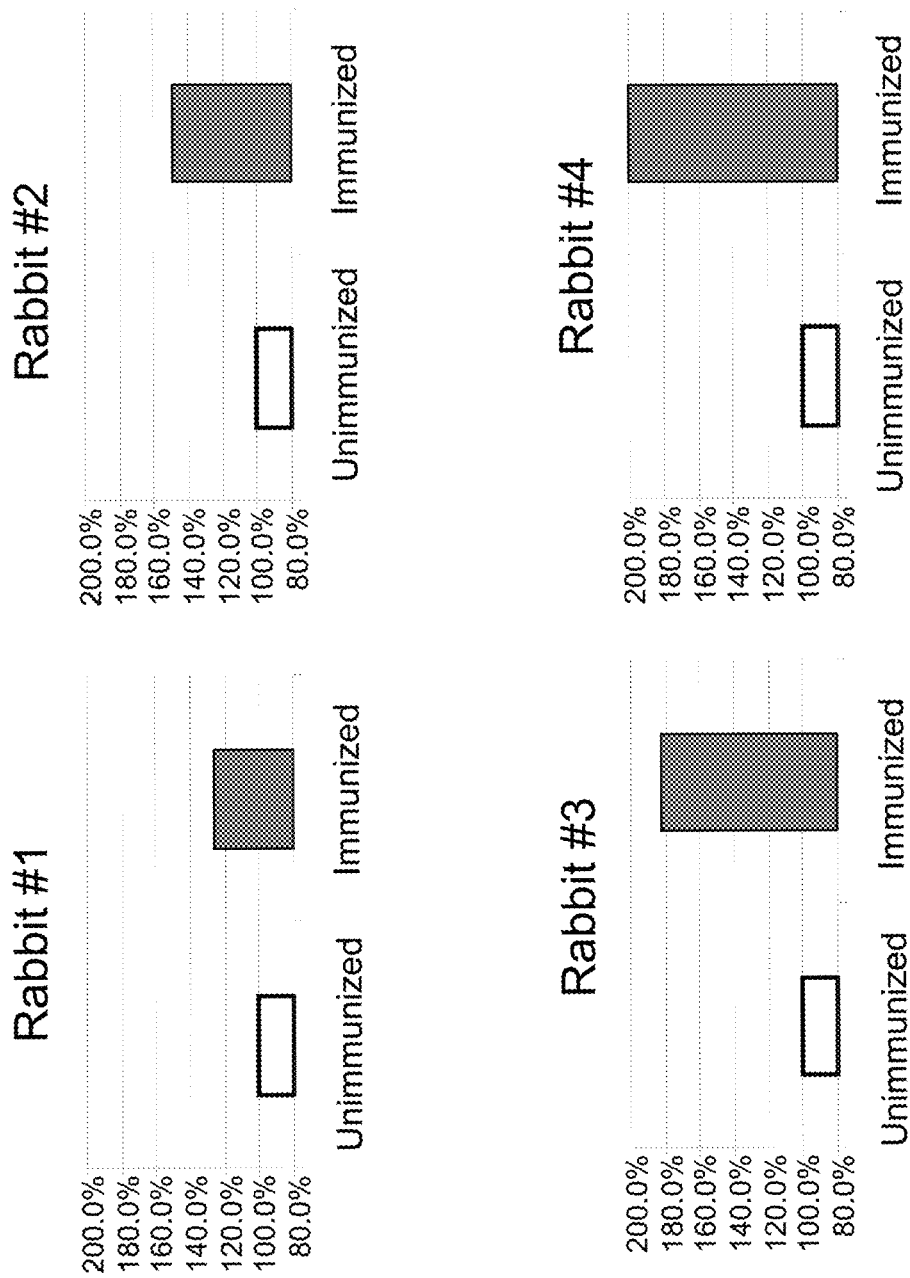
FIG. 21 shows the anti-ABri antibody-inducing effect produced by YM3711 in rabbits.
Figure 22:
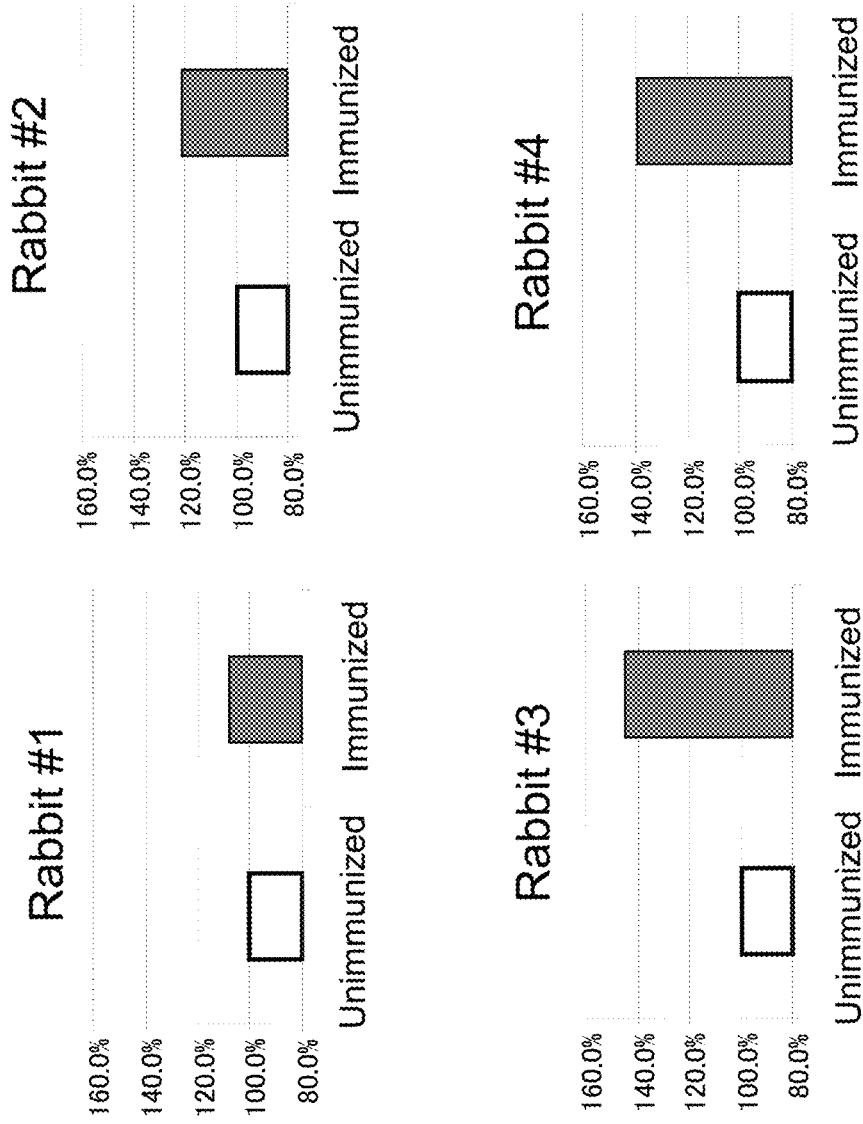
FIG. 22 shows the anti-ADan antibody-inducing effect produced by YM3711 in rabbits.

The results obtained with rabbits are shown in FIGS. 20 to 22. FIG. 20 shows the anti-pEAβ3-42 antibody-inducing effect produced by YM3711, FIG. 21 shows the anti-ABri antibody-inducing effect produced by YM3711, and FIG. 22 shows the anti-ADan antibody-inducing effect produced by YM3711. In FIGS. 20 to 22, "Rabbits #1 and #2" show the results in rabbits administered with the existing vaccine (pVAX1/IgL-Aβ1-42-huIgFc), while "Rabbits #3 and #4" show the results in rabbits administered with YM3711.

These results indicated that YM3711 induced anti-pEAβ3-42 antibody, anti-ABri antibody and anti-ADan antibody in the rabbits administered therewith. Table 4 below shows the % increase in antibody titer after immunization with YM3711.

[Table 4]

TABLE 4

Increase (%) in antibody titer after immunization (%)

Anti-pEAβ3-42 antibody

| | Rabbit #1 | Rabbit #2 |
|---|---|---|
| Existing vaccine | 18 | 1 |
| | Rabbit #3 | Rabbit #4 |
| YM3711 | 38 | 37 |

Anti-ABri antibody

| | Rabbit #1 | Rabbit #2 |
|---|---|---|
| Existing vaccine | 26 | 50 |
| | Rabbit #3 | Rabbit #4 |
| YM3711 | 81 | 100 |

Anti-ADan antibody

| | Rabbit #1 | Rabbit #2 |
|---|---|---|
| Existing vaccine | 8 | 20 |
| | Rabbit #3 | Rabbit #4 |
| YM3711 | 43 | 39 |

As shown in Table 4, the rabbits administered with the existing vaccine ("Rabbits #1 and #2" in Table 4) showed an increase of 1% to 18% for anti-pEAβ3-42 antibody, 26% to 50% for anti-ABri antibody, and 8% to 20% for anti-ADan antibody, when compared to before immunization. In contrast, the rabbits administered with YM3711 ("Rabbits #3 and #4" in Table 4) showed an increase of 37% to 38% for anti-pEAβ3-42 antibody, 81% to 100% for anti-ABri antibody, and 39% to 43% for anti-ADan antibody. This indicates that YM3711 causes remarkable induction of anti-pEAβ3-42 antibody, anti-ABri antibody and anti-ADan antibody in rabbits, in comparison with the existing vaccine.

Figure 23:
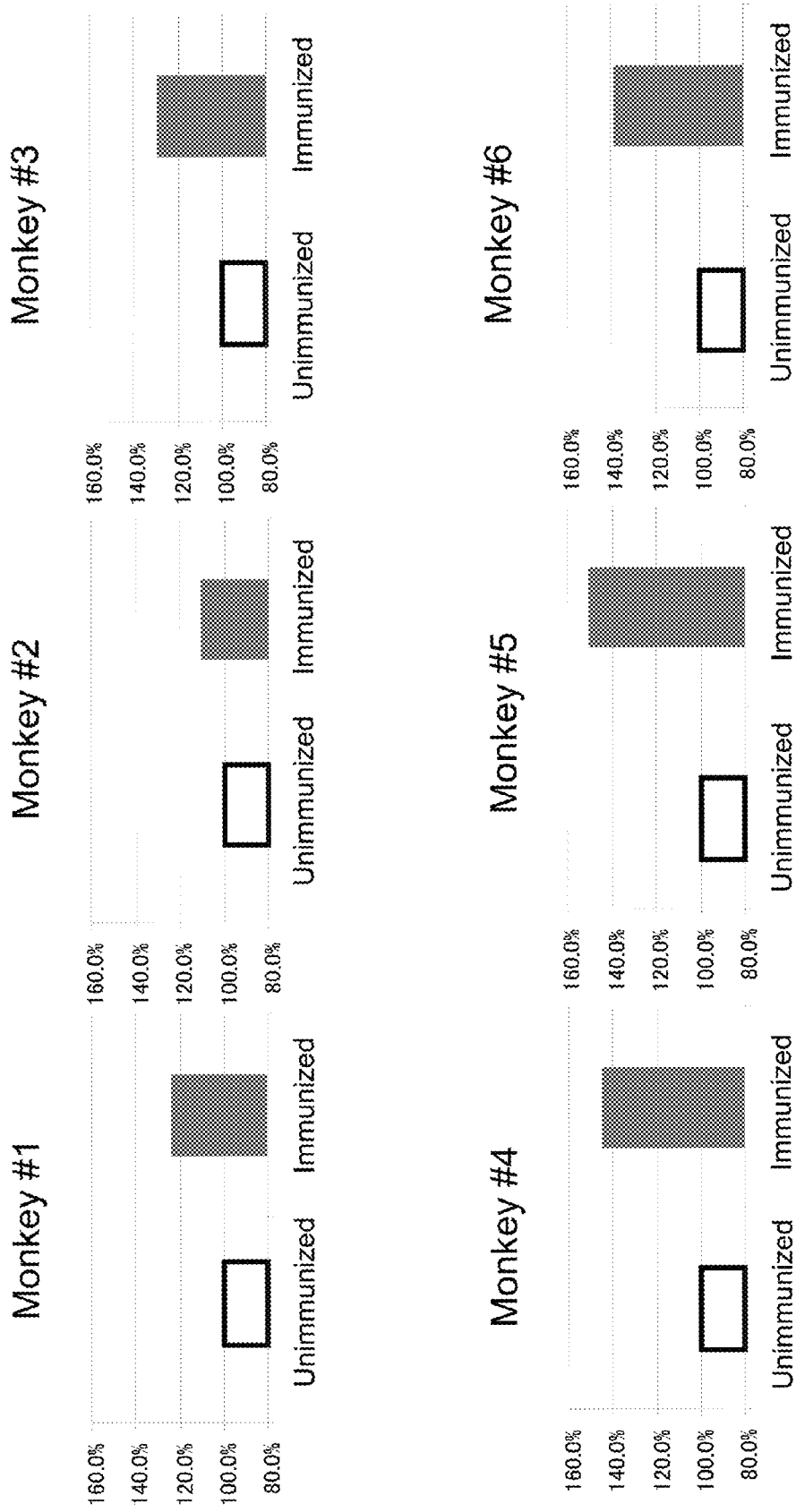
FIG. 23 shows the anti-pEAb3-42 antibody-inducing effect produced by YM3711 in monkeys.
Figure 24:
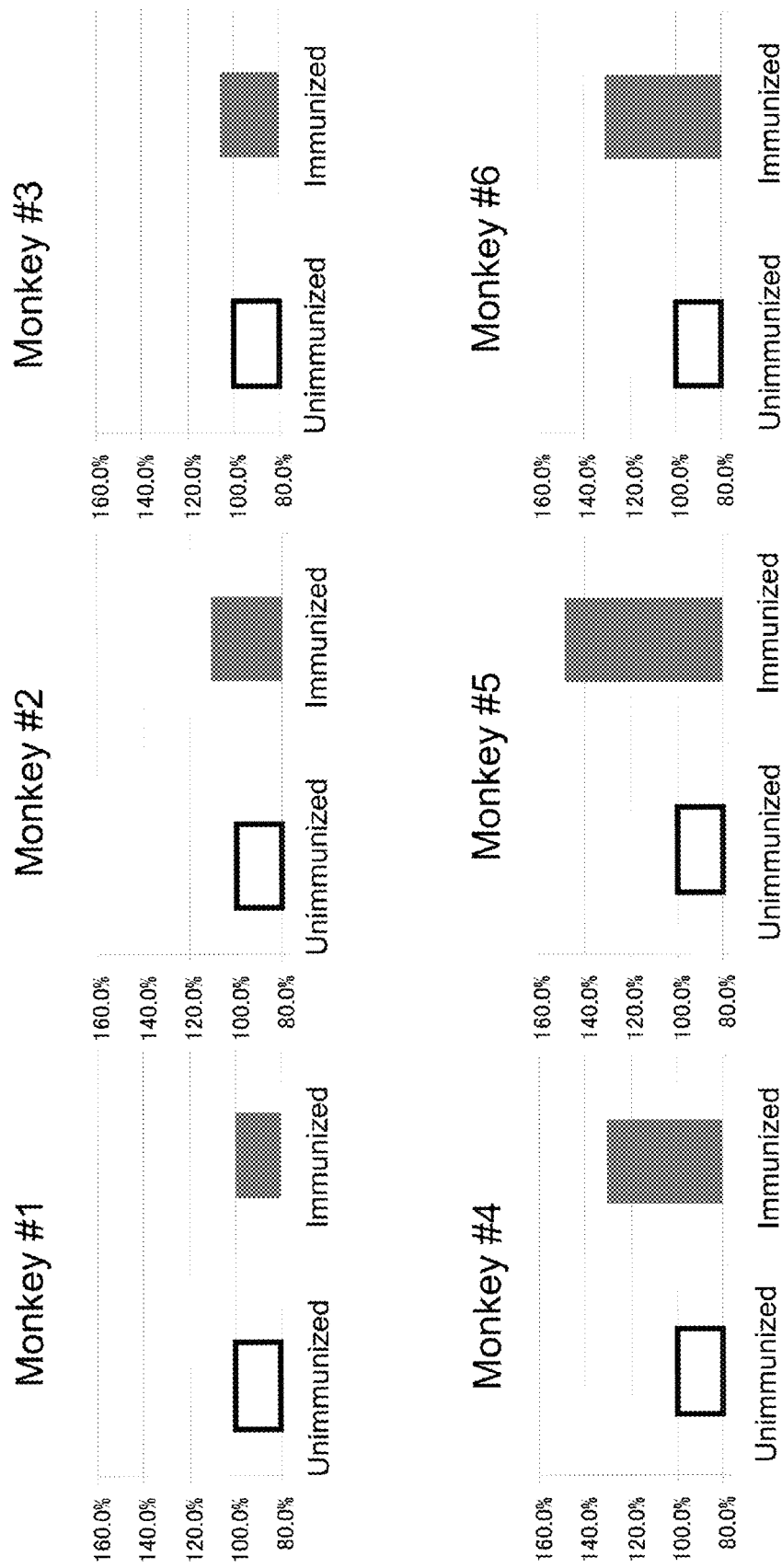
FIG. 24 shows the anti-ADan antibody-inducing effect produced by YM3711 in monkeys.

The results obtained with monkeys are shown in FIGS. 23 and 24. FIG. 23 shows the anti-pEAβ3-42 antibody-inducing effect produced by YM3711, and FIG. 24 shows the anti-ADan antibody-inducing effect produced by YM3711. In FIGS. 23 and 24, "Monkeys #1 to #3" show the results in monkeys administered with the existing vaccine (pVAX1/IgL-Aβ1-42-huIgFc), while "Monkeys #4 to #6" show the results in monkeys administered with YM3711.

These results indicated that YM3711 induced anti-pEAβ3-42 antibody and anti-ADan antibody in the monkeys administered therewith. Table 5 below shows the % increase in antibody titer after immunization with YM3711.

[Table 5]

TABLE 5

Increase (%) in antibody titer after immunization (%)

Anti-pEAβ3-42 antibody

|  | Monkey #1 | Monkey #2 | Monkey #3 |
|---|---|---|---|
| Existing vaccine | 24 | 10 | 30 |
|  | Monkey #4 | Monkey #5 | Monkey #6 |
| YM3711 | 43 | 50 | 39 |

Anti-ADan antibody

|  | Monkey #1 | Monkey #2 | Monkey #3 |
|---|---|---|---|
| Existing vaccine | 0 | 9 | 4 |
|  | Monkey #4 | Monkey #5 | Monkey #6 |
| YM3711 | 31 | 49 | 30 |

As shown in Table 5, the monkeys administered with the existing vaccine ("Monkeys #1 to #3" in Table 5) showed an increase of 10% to 30% for anti-pEAβ3-42 antibody and 0% to 9% for anti-ADan antibody, when compared to before immunization. In contrast, the monkeys administered with YM3711 ("Monkeys #4 to #6" in Table 5) showed an increase of 39% to 50% for anti-pEAβ3-42 antibody and 30% to 49% for anti-ADan antibody. This indicates that YM3711 causes remarkable induction of anti-pEAβ3-42 antibody and anti-ADan antibody in monkeys, in comparison with the existing vaccine.

Example 3

Further Vaccination Test with pVAX1/IgL-(Aβ1-42)x4-huIgFc-huIL-4 (YM3711)

1. Materials and Methods (1) In Vitro Characterization

For in vitro characterization, HEK293 cells were cultured in a 6-well plate and transfection with YM3711 or other DNA vaccines was performed under 90% confluency. Briefly, 4 µg of the indicated DNA vaccine was mixed with 10 µl of LIPOFECTAMINE® 2000 Transfection Reagent (Invitrogen) in OPTI-MEM I and kept at room temperature for 20 min. Then, the mixture was added to each well and the plates were cultured for 4 h. After washing with DMEM (Invitrogen), the cells were further cultured for 3 days. The supernatant, and occasionally cell pellet, of transfected cells were harvested and subjected to Aβ quantitation using the Human 13 Amyloid (1-42) ELISA Kit Wako, High-Sensitive (Wako, Osaka) according to the manufacturer's instruction. $OD_{450}$ was read with ARVO X3 (PerkinElmer Japan, Kanagawa).

IL-4 activities were determined by bioassay using an IL-4-dependent cell line, TF-1. Culture supernatant of YM-3711-transfected cells or recombinant human IL-4 at various concentrations was added to cultured TF-1 cells. Culture supernatant of non-transfected cells served as negative controls. Using the BrdU uptake assay, the level of bioactive IL-4 was determined IL-4 activities of the supernatant were determined based on values obtained from serially diluted IL-4.

(2) Animals and DNA Vaccination

B6C3-Tg (APPswe, PSEN1dE9) 85Dbo/J mice (hereafter referred to as model mice in the present application) were purchased from the Jackson Laboratory (Bar Harbor, Me.) and bred in our animal facilities. New Zealand white rabbits were obtained from Japan SLC Inc. All procedures including vaccination and blood sampling of *Macaca fascicularis* were performed at Bozo Research Center (Shizuoka, Japan). All animal experiments were conducted in accordance with the Guidelines for the Care and Use of Animals (Tokyo Metropolitan Institute of Medical Science, 2011). Experimental protocols were approved by the Animal Use and Care Committee of the Tokyo Metropolitan Institute of Medical Science.

For in vivo vaccination, YM3711 at doses of 100 µg for mice, 1 mg for rabbits and 2 mg for monkeys was administered intramuscularly once a week for 6 weeks. Blood was drawn biweekly and titers of antibodies against the indicated Aβ-related peptides were determined by standard ELISA. At the end of experiments, treated and control animals were killed under deep anesthesia and the brains were removed for examination.

(3) Biodistribution Analysis (3-1) Construction of Primer Pairs for Biodistribution and their Specificity The present inventors prepared three primer pairs for quantitative polymerase chain reaction (qPCR) analysis (FIG. 25A). Preliminary studies using purified YM3711 plasmid DNA revealed that YM3711 plasmid DNA were amplified by PCR with all three primer pairs and Primer pair A (FIG. 25A) produced the PCR product in a dose dependent manner (FIG. 25B, left panel). In contrast, an empty vector was not amplified with Primer pair A (FIG. 25B, right panel). Thus, this primer pair was used in further studies. Sequences of Primer Pair A are Forward 5'-CAT CGA GAA AAC CAT CAG CA (SEQ ID NO: 34) and Reverse 5'-CTG GTT CTT GGT CAG CTC GT (SEQ ID NO: 35). Real-Time PCR was performed using IQ™ SYBR™ Green Supermix (BIO-RAD, CA). Each PCR was performed in duplicate using following thermocycler conditions: stage 1, 95° C. for 10 min for one cycle and stage 2, 95° C. for 15 s and 58° C. for 1 min for 35 cycles.

(3-2) Sensitivity of Quantitative PCR

Serial 10-fold dilutions of purified YM3711 plasmid DNA, ranging from 19.39 to $1.9 \times 10^6$ copies in the presence or absence of genomic DNA were amplified and quantitated by real-time PCR to construct the standard curve. The standard curve made with YM3711 plasmid DNA alone showed good linearity (data not shown). Then, the standard curve was constructed in the presence of 100 ng genomic DNA to evaluate the influence of irrelevant DNA. Previous studies demonstrated that addition of more than 100 ng DNA interfered the efficacy of PCR amplification (Fu J, et al, Anal Sci 2009; 25: 675-680). Addition of 100 ng DNA in the present application did not influence the sensitivity of qPCR. Amplification efficacies of YM3711 alone and YM3711 plus 100 ng DNA were 94.5% and 99.5%, respectively. Based on these data, it was estimated that this detection system is able to detect 40 copies/100 ng DNA.

(3-3) Protocol for Biodistribution Analysis

YM3711 at a dose of 100 μg DNA/mouse (100 μl/shot) was injected once in the anterior tibialis muscle of C57BL/6 mice. Mice (n=3 for each group) were sacrificed on days 0 (preimmune status), 1, 7, 14 and 30 following vaccination. Muscle tissue at the injection site, the inguinal lymph node, bone marrow, spleen, liver, kidney, lung and brain were sampled and processed for DNA isolation. Using a primer pair specific for the YM3711 sequence (Primer pair A in FIG. 25A), the amounts of YM3711 in various organs were determined by real-time PCR.

(4) Measurement of Aβ and Anti-Aβ Antibodies in Plasma and the Brain

For measurement of antibodies against Aβ species (e.g., Aβ1-42, pEAβ3-42, Aβ oligomer, Aβ fibril) and amyloidogenic peptides (e.g., ADan, ABri), microtiter plates were coated with the indicated peptides (2 μg/ml) in 0.1 M sodium carbonate buffer (pH 9.5) for 4 hours at room temperature. After washing, plates were incubated over night at 4° C. with serially diluted plasma samples in PBS. The plates were washed and incubated with horse radish peroxidase-conjugated secondary antibodies. Bound antibodies were detected using SIGMA FAST (Sigma-Aldrich) and the absorbance at 450 nm was read on an automated plate reader (Model 550; Bio-Rad laboratories). To avoid inter-assay variations, all the samples to be compared were assayed at once.

The amount of Aβ and related molecules was quantitated by a sandwich ELISA, Human Amyloid 13 (1-42, pE3-42 or Oligomers) Immunoassay Kit (IBL, Takasaki, Japan), according to the manufacturer's instructions. The brain tissue was homogenized in a guanidine-HCl buffer and the supernatant was collected after centrifugation. An appropriate amount of the brain extract was subjected to the assay.

(5) Western Blot Analysis of Aβ Fibrils

The frontal cortex was subjected to analysis. Cortical tissue was homogenized in cold TBS buffer (50 mM Tris-HCl, 0.2 M NaCl, pH7.5) containing a protease inhibitor cocktail (SIGMA). After centrifugation at 100,000×g for 1 h, the pellet was homogenized in TBS buffer containing 1% Triton X-100. Then, the pellet was again homogenized in Guanidine buffer (5 M GuHCl, 50 mM Tris-HCl, pH8.0) and incubated overnight at room temperature. The supernatant obtained after centrifugation was used for Western blotting with anti-Aβ fibril mAb, OC.

After adding NUPAGE® LDS sample buffer (Invitrogen), the samples were incubated at 70° C. for 10 min and were run on NUPAGE® 12% Bis-Tris gel (Invitrogen, Tokyo). Then, they were transferred to PVDF membrane (IMMOBILON®-P; Millipore). After blocking with 10% nonfat milk, the blots were incubated with anti-AP fibrils OC (Merk Millipore) (1:1000) at 4° C. overnight followed by incubation with True-blot HRP-conjugated anti-mouse IgG (eBioscience, San Diego, Calif.) (1:1000) for 1 hr. The blots were developed by enhanced chemiluminescence reagents (ECL Plus Western Blotting Detection System, GE Healthcare) according to the manufacturer's instructions. The image was obtained with an image analyzed (LAS-3000 mini, Fuji Film) and the densities of 56 kDa bands was quantitated using the Image J Software.

Figure 28:
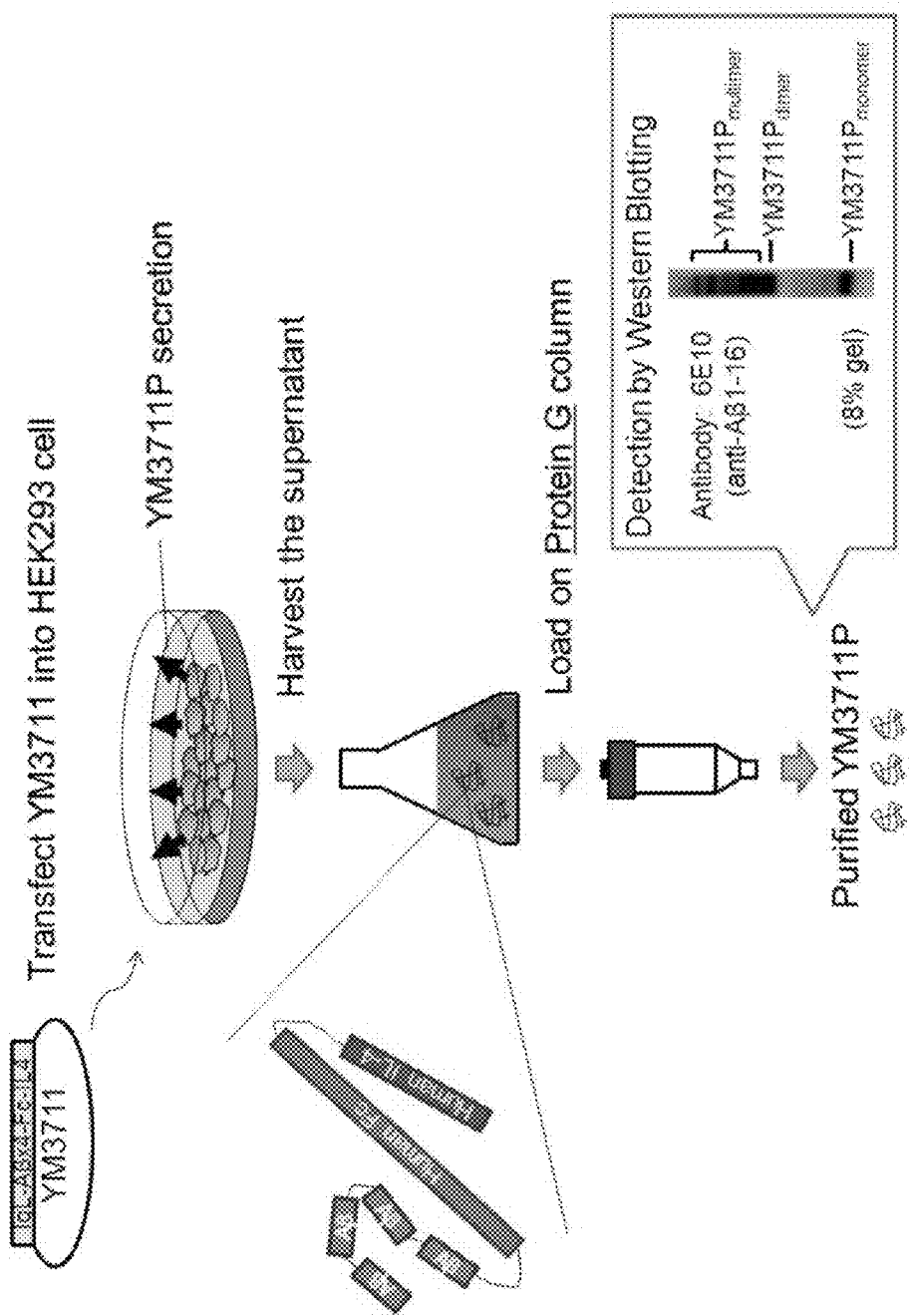
FIG. 28 shows purification of translated YM3711 products (YM3711P).

(6) Purification of Translated YM3711 Product (YM3711P) and Anti-YM3711P Antibodies HEK293 were cultured in a 175 $cm^2$ flask (total volume, 300 ml) and transfected with YM3711, as shown above. After 4 days, culture supernatant was harvested and filtered. Since YM3711P contains the Fc portion of immunoglobulin, the product was further purified on a HITRAP™ Protein G column (GE Healthcare Japan). The eluate at O.D. 280 nm was harvested and strong Aβ immunoreactivities were confirmed using anti-Aβ mAb, 6E10 (FIG. 28).

Anti-YM3711P antibodies were purified on a HITRAP™ Protein G column using 0.5 ml post-immune rabbit plasma. They were then biotinylated with Sulfo-NHS-LC Biotin (Pierce).

(7) Binding and Competition Assays Using YM3711P

YM3711P at concentrations of 2 μg/ml, 10 μg/ml and 20 μg/ml or Aβ1-42 (2 μg/ml) were coated onto microtiter wells. After blocking, biotinylated IgG purified from plasma of rabbits that had been vaccinated with YM3711 were applied and followed by HRP-labeled VECTSTAIN Elite ABC Kit. Bound antibodies were detected using SIGMA FAST (Sigma-Aldrich) and the absorbance at 450 nm was read. Samples showing O.D. more than 2.5 were further diluted and reexamined. Calculated O.D. values are shown in the figure (FIG. 29).

Figure 30:
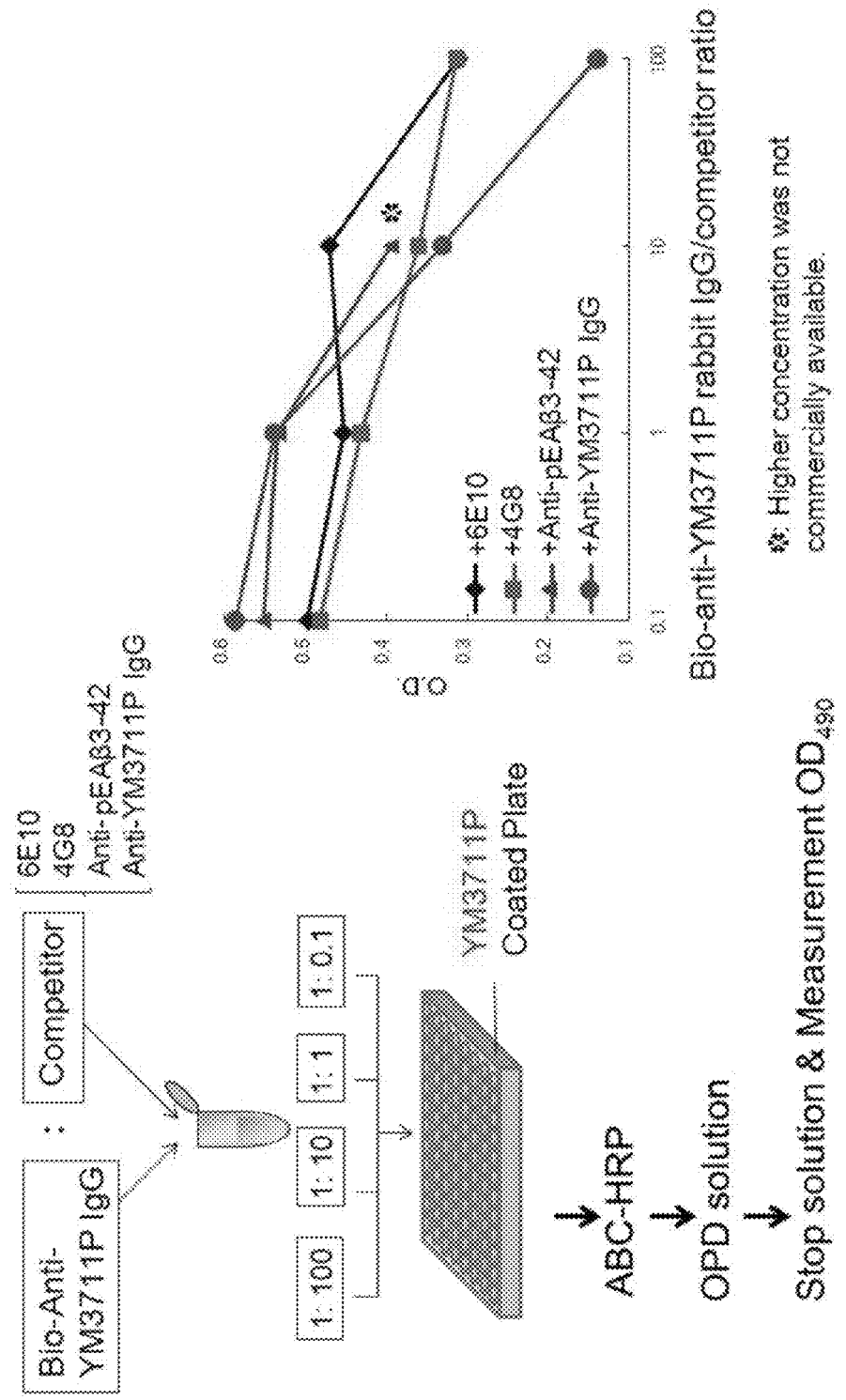
FIG. 30 shows competition assays using YM3711P.

For competition assay, YM3711P at a concentration of 2 μg/ml was applied onto microtiter wells. Then, wells were incubated with a mixture of biotinylated anti-YM3711P IgG and unlabeled various competitors at 0.1 to 100 ratios. Competitors included 6E10 (Covance Japan), 4G8 (Covance Japan), anti-pEAβ3-42 antibodies (Immuno-Biological Laboratories), anti-Aβ oligomer antibodies (Life Technologies Japan) and unlabeled anti-YM3711P IgG Then, the absorbance was read in the same way as the binding assay (FIG. 30).

(8) Detection of Antibodies Recognizing Conformational Epitope(s) in Plasma of YM3711-Vaccinated Rabbits The IgG fraction was purified from plasma taken from rabbits that had been vaccinated with YM3711 using a HITRAP™ Protein G HP column (GE Healthcare Japan). Then, IgG was segregated to antibodies recognizing the linear and conformational epitopes by applying a HITRAP™ Protein G column NHS-activated HP (GE Healthcare Japan) coupled with the mixture of short Aβ peptides i.e., Aβ1-11, 7-17, 13-23, 19-29, 25-35 and 31-42 (PH Japan, Hiroshima). By this procedure, anti-conformational epitope antibodies were obtained in the flow-through fraction and anti-linear epitope antibodies were obtained in the eluate. The titers of both types of antibodies were determined by ELISA using the short peptide mixture, Aβ1-42 (Peptide Institute Inc, Osaka) or purified YM3711 products as an antigen.

(9) Statistical Analysis

The Student's t test or Mann-Whitney's U-test was used for the statistical analysis. P-values less than 0.05 were considered significant.

2. Results (1) Biodistribution of YM3711

Figure 26:
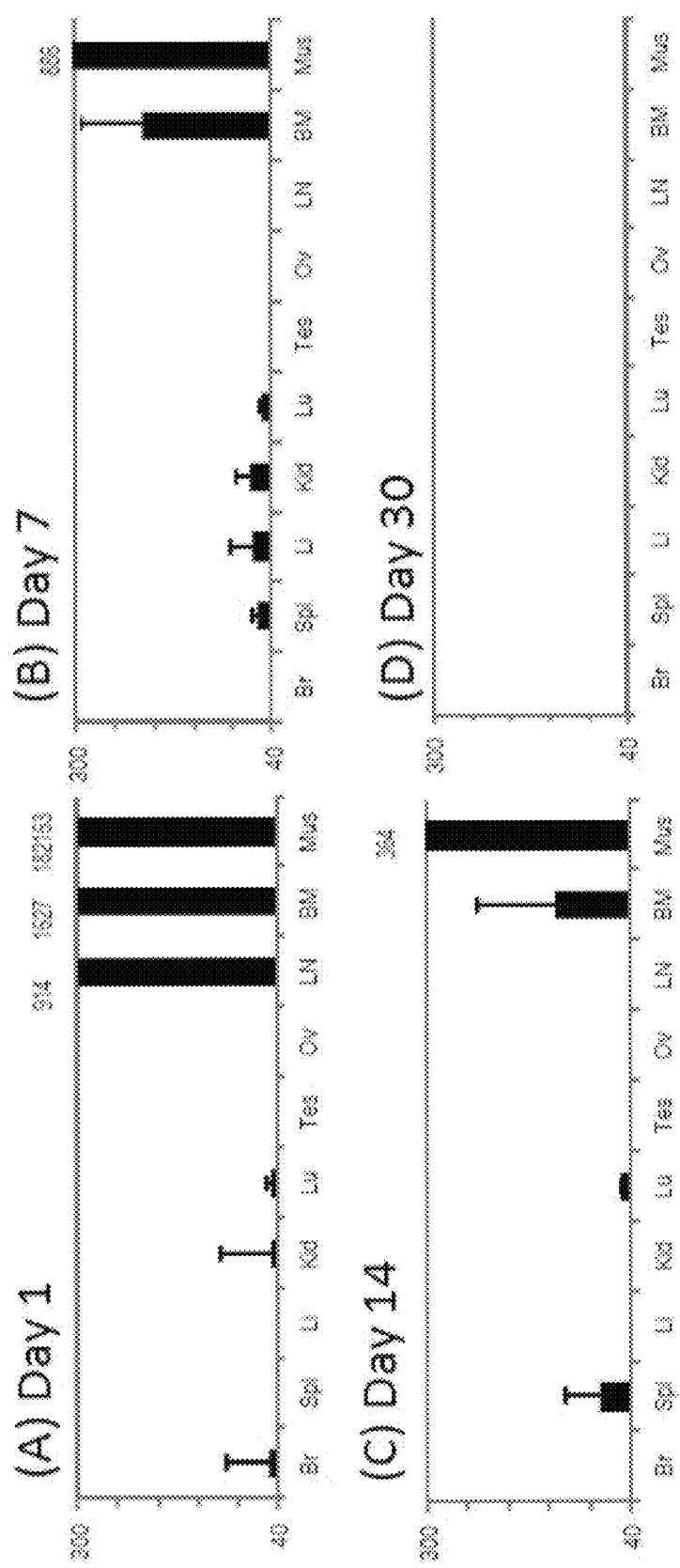
FIG. 26 shows distribution of YM3711 at various time points after intramuscular injection. Mus, muscle of injection site; LN, inguinal lymph node; BM, bone marrow; Spl, spleen; Liv, liver; Kid, kidney; Lu, lung; Br, brain; Tes, testis; Ov, ovary. The Y axis indicates copy number of YM3711 in 100 ng tissue DNA. The mean values±SD of three animals are shown. YM3711 levels are depicted post vaccination on Day 1, Day 7, Day 14, and at one month in FIGS. 26A, 26B, 26C, and 26D, respectively.

Under normal conditions before YM3711 vaccination, YM3711 was not detectable in all organs examined (data not shown). On day 1 post-vaccination, YM3711 was found at high levels in the muscle (injected site), bone marrow and the regional lymph node (LN) (FIG. 26A). On day 7, YM3711 was highly detected in the muscle and bone marrow but was absent in LN (FIG. 26B). A small amount of the vaccine was also detectable in the spleen, kidney and liver (FIG. 26B). The distribution of YM3711 on day 14 was almost the same as that on day 7 (FIG. 26C). One month after the vaccination, YM3711 was not detected in all organs examined (FIG. 26D). Importantly, levels of YM3711 in the testis and ovary were below the detection level throughout the examination.

(2) Detection of Antibodies Against Parts of YM3711 Products (Aβx4, Fc and IL4)

Figure 27:
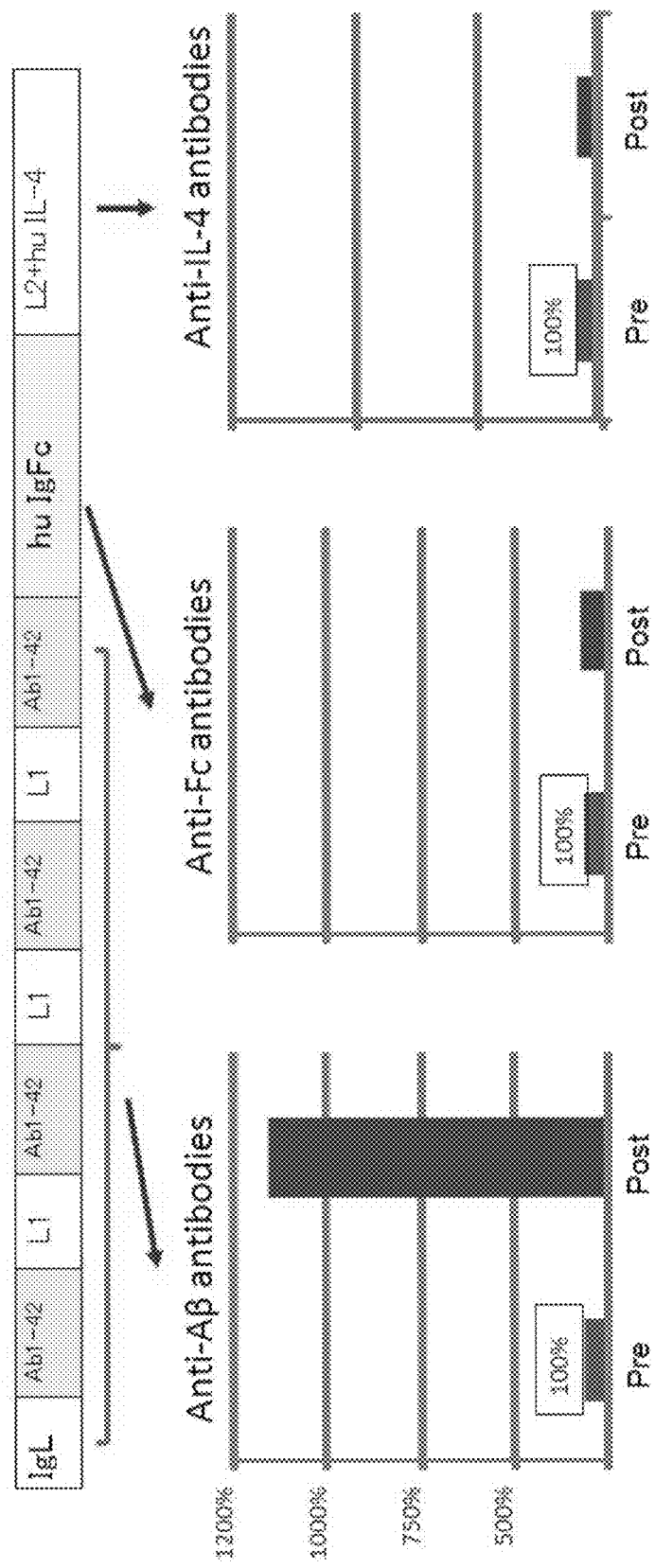
FIG. 27 shows detection of antibodies against parts of YM3711 products (Aβ, Fc and IL4).

In Example 2, the present inventors have demonstrated that YM3711 vaccination induced a significant elevation of anti-Aβ, anti-Aβ species and anti-amyloidogenic-peptide antibodies in mice, rabbits and/or monkeys. It is also important to characterize the nature of raised antibodies in more detail. For this purpose, the levels of antibodies directed at components of translated YM3711 products, Aβ1-42, human Fc portion and recombinant IL-4 were respectively coated onto ELISA plates and antibody titers for these components were determined using plasma taken from cynomolgus monkeys before and after the vaccination (FIG. 27). Anti-AP antibodies were elevated about 10 folds after vaccination compared with those of preimmune plasma (FIG. 27, left panel). In contrast, YM3711 vaccination of monkeys did not induced antibodies against the Fc and IL-4 portions (FIG. 27, middle and right panels, respectively). Since Aβ deposition was not noted in aged cynomolgus monkeys (our observation in Tokita et al, 2010), exogenous Aβ induced profound anti-Aβ antibody elevation. In contrast, the sequences of human Fc and IL-4 are highly homologous to those of monkeys so that the antibody-inducing abilities of these components would be minimal.

(3) Characterization of Antibodies Induced by YM3711 Vaccination with Binding and Competition Assays Using YM3711 Products (YM3711P)

To further characterize the nature of antibodies raised by YM3711 vaccination, the present inventors prepared YM3711 products (YM3711P) (FIG. 28) and anti-YM3711P antibodies and examined them by binding and competition assays. For the binding assay, YM3211P obtained from the culture supernatant of YM3711-transfected HEK 239 cells were coated onto 96-well plates. Then, biotinylated anti-YM3711P IgG that had been purified from plasma of YM3711-vaccinated rabbits. The results are summarized in FIG. 29. Purified IgG contained high titers of anti-YM3711P antibodies, whereas anti-Aβ1-42 antibody titer was low. This finding strongly suggests that a large part of antibodies in YM3711-vaccinated rabbits are directed at conformational epitopes of the Aβ complex.

Then, the present inventors performed a competition assay (FIG. 30). Microtiter wells coated with YM3711P were incubated with a mixture of biotinylated anti-YM3711P IgG and various unlabeled competitors at 0.1 to 100 ratios. As expected, cold anti-YM3711 IgG showed strong competing abilities in a dose-dependent manner, whereas two anti-Aβ mAbs and anti-pEAβ3-42 antibodies exhibited relatively weak competing abilities. Although Western blot analysis (data not shown) suggested that pyroglutamation does not take place soon after in vitro YM3711 product formation, they may form at a very low level because anti-pEAβ3-42 antibodies showed some competing abilities.

(4) Switch of the Specificity in the Antibody Pool of Vaccinated Animals

Figure 31:
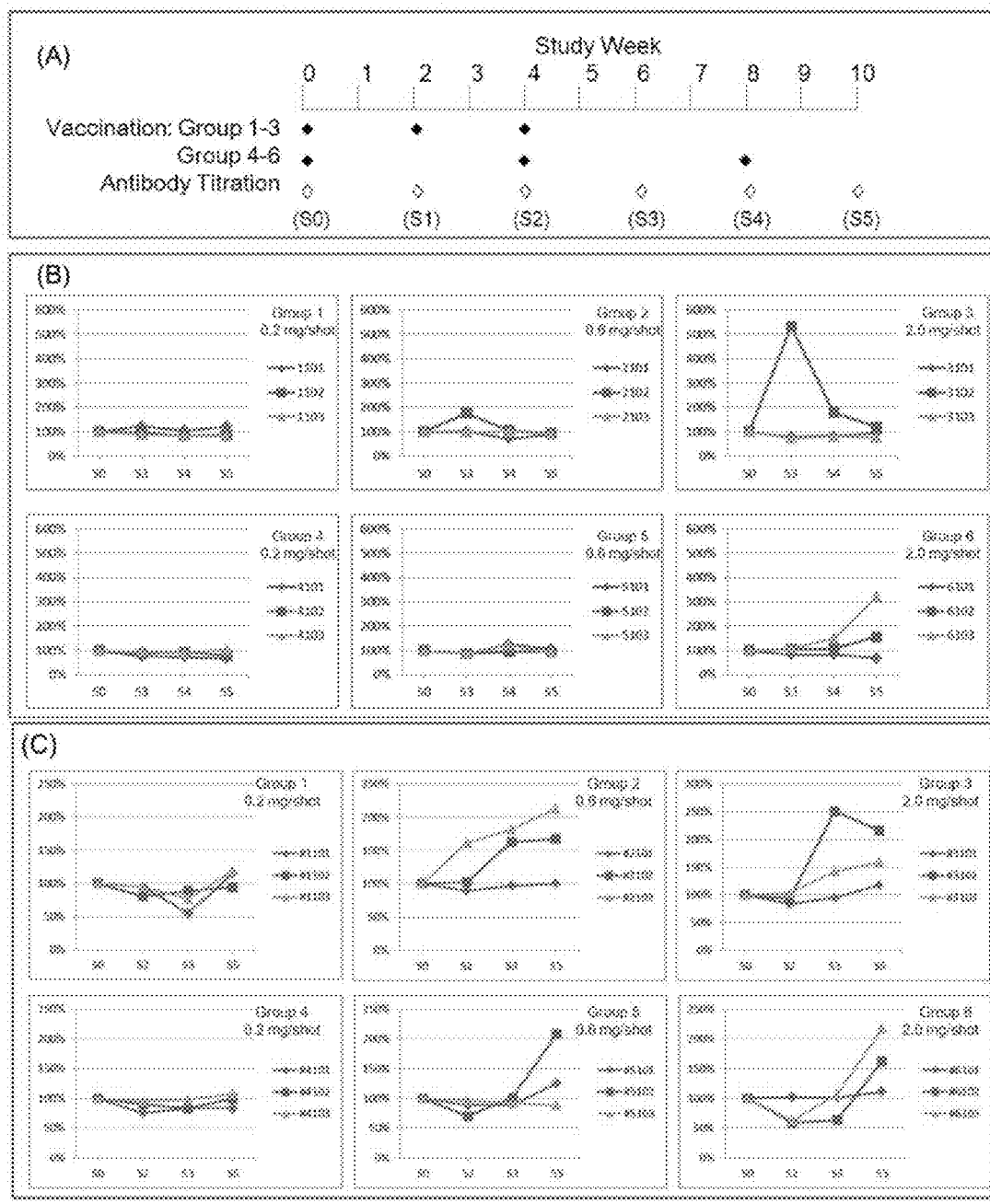
FIG. 31 shows kinetics of antibody titers against Aβ1-42 (FIG. 31B) and YM3711P (FIG. 31C) in plasma of monkeys.

To further characterize the nature of antibodies raised by YM3711 vaccination, the present inventors measured anti-YM3711P antibody titers in plasma of monkeys that had been immunized with YM3711 according to the protocol shown in FIG. 31A. Then, kinetics of anti-YM3711P antibody titers in plasma of monkeys that had been immunized with YM3711 at doses of 200 μg (FIG. 31C, left), 600 μg (FIG. 31C, middle) and 2000 μg (FIG. 31C, right) was determined and compared with that of anti-Aβ1-42 antibody titers (FIG. 31B). While anti-Aβ1-42 antibodies elevated transiently during or soon after vaccination and declined thereafter (FIG. 31B), anti-YM3711P antibodies elevated similarly but maintained plateau levels till the end of examination (FIG. 31C). These findings suggest that YM3711 vaccination initially induces antibodies to linear epitopes in Aβ1-42. At the same time, repeated vaccination elicits antibodies to conformational epitopes in the Aβ complex and this elevation persists for a relatively long period even after cessation of the vaccination. As shown above, plasma of YM3711-vaccinated animals did not react with Fc or IL-4 in the ELISA assay (FIG. 27). Thus, it is expected that several YM3711 injections would induce a sufficient titer of antibodies reacting with a wide range of Aβ, Aβ oligomer and other Aβ species and reduce Aβ burden in the brain of patients with Alzheimer's disease.

Figure 32:
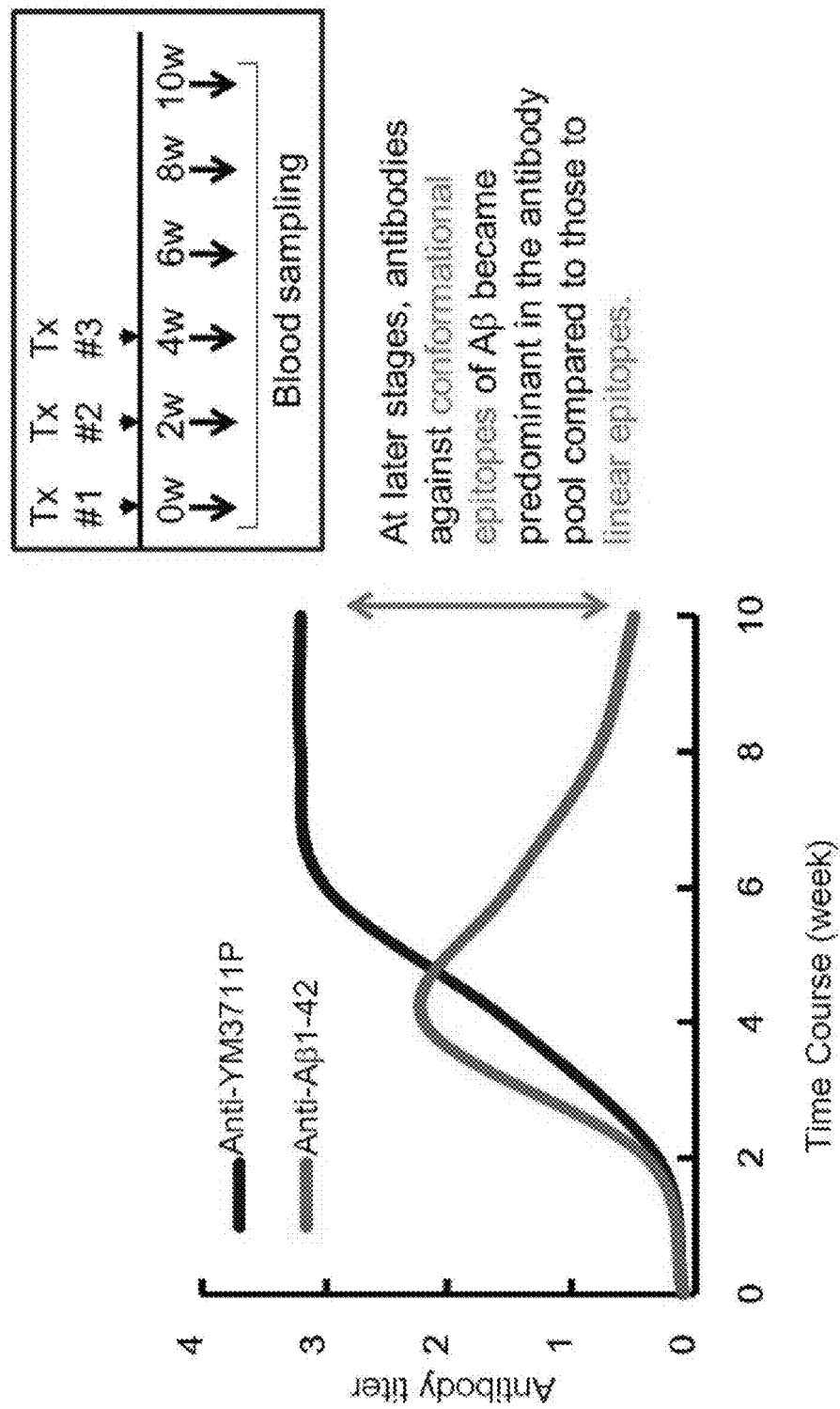
FIG. 32 shows schematic drawing of switch of the specificity in the antibody pool of vaccinated animals.

These findings indicate that at the beginning of YM3711 vaccination, antibodies directed at linear epitope(s) of Aβ were induced. However, at later stages, antibodies against conformational epitopes of Aβ became predominant in the antibody pool compared to those to linear epitopes. Thus, switch of the specificity in the antibody pool occurs in animals during vaccination (FIG. 32).

Figure 33:
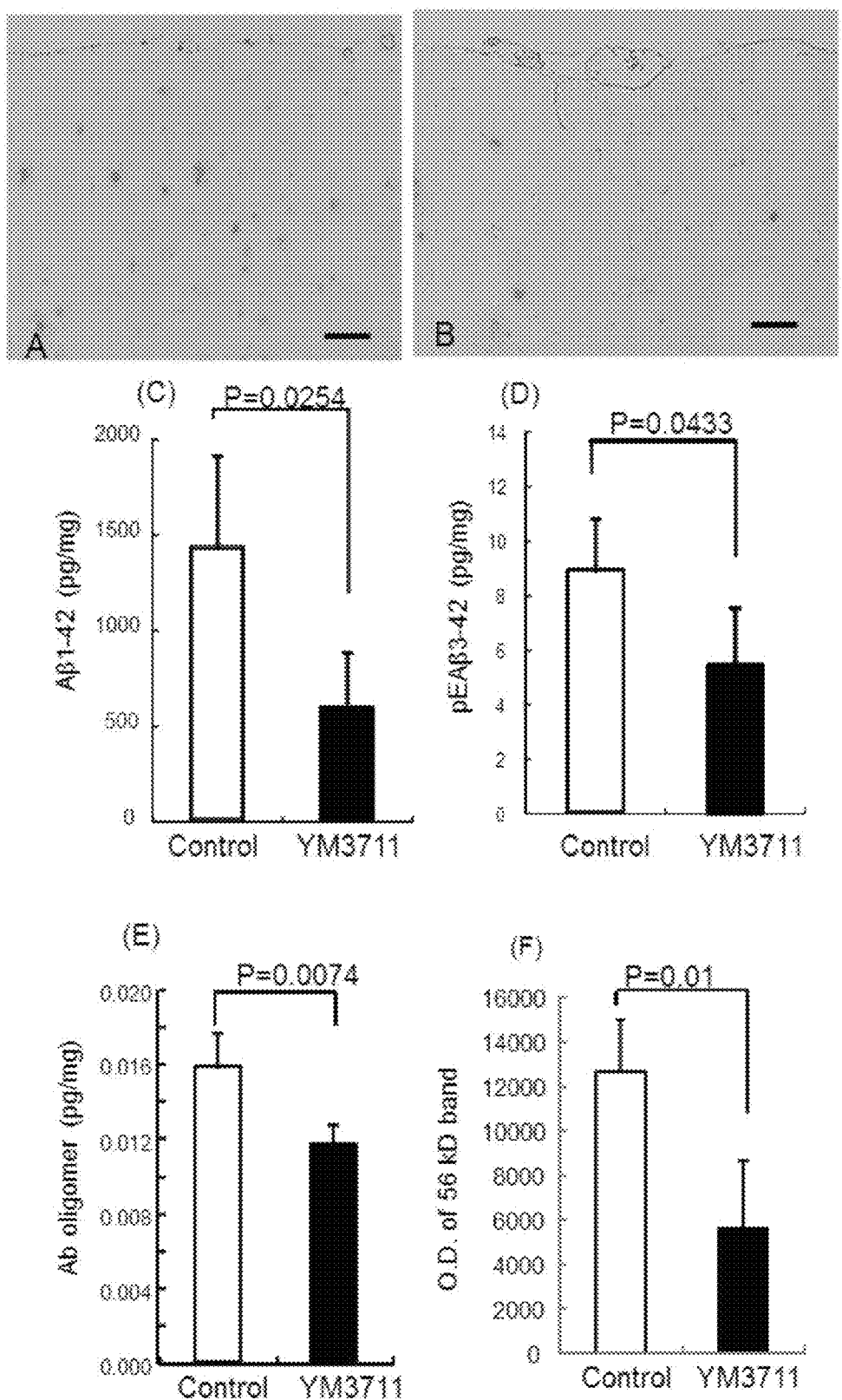
FIG. 33 shows that YM3711 vaccination effectively reduced not only Aβ1-42 but also other Aβ species. (A) and (B): bar=100 μm. (C) to (F): closed columns, Aβ in the cerebral cortex of vaccinated mice (n=4); Open columns, Aβ in the cerebral cortex of age-matched control mice (n=5).

(5) In Vivo Administration of YM3711 Reduces not Only Aβ1-42 but Also Other Aβ Species in Model Mice YM3711 at a dose of 100 μg was injected weekly to model mice for 6 weeks and brains were taken at 8 weeks. Immunostaining for Aβ in the brain revealed that compared with untreated control mice (FIG. 33A), Aβ deposits in the frontal cortex were clearly decreased in vaccinated mice (FIG. 33B).

Quantitative analysis by a sandwich ELISA (FIG. 33C-E) demonstrated a significant reduction of Aβ1-42 in treated mice (FIG. 33C) (p=0.0254). Furthermore, pEAβ3-42 (FIG. 33D) and Aβ oligomer (FIG. 33E) quantitation revealed significant reduction in the YM3711-treated group (p=0.0433 and p=0.0074, respectively). In addition, Aβ species recognized by anti-Aβ fibrils monoclonal antibody in treated and control model mice were semiquantitated by measuring densities of 56 kDa bands in Western blots. As clearly shown, Aβ fibrils were significantly reduced in treated monkeys (p=0.0099, FIG. 33F).

(6) Toxicology Study of YM3711 in Monkeys and Mice

YM3711 was injected six times to monkeys (FIG. 34A) and mice (FIG. 34B) according to the protocol shown in FIG. 34. Monkeys were injected with PBS (Control) or YM3711 (Low dose, 2000 μg/shot; High dose, 4000 μg/shot). Mice received PBS (Control) or mouse-type YM3711 at doses of 100 μg/shot (Low dose) and 300 μg/shot (High dose). At end points, brains were removed and processed for hematoxylin and eosin or other staining. Then, histological examination of brains was performed extensively to determine the presence or absence of adverse events such as hemorrhage and inflammation. Consequently, none of monkeys and mice showed hemorrhage and inflammation in all groups examined. Furthermore, extensive studies with biochemical analysis of blood and histological examinations of almost all organs revealed no pathological changes after YM3711 vaccination (data not shown).

3. Discussion

In Example 2, the present inventors did in vitro and in vivo studies to characterize the nature of a newly developed DNA vaccine (Code name, YM3711) and its Aβ reduction effects. Aβ production and Aβ secretion abilities were evaluated using YM3711-transfected cultured cells. YM3711-transfected cells produced 5-6 fold larger amount of Aβ and secreted Aβ 3-4 fold higher in the culture supernatant compared with previously developed DNA vaccines. Anti-Aβ, anti-Aβ species and anti-amyloidogenic-peptide antibody-inducing and Aβ-reducing abilities were determined using plasma and brains from YM3711-vaccinated animals. When vaccinated to mice and rabbits, YM3711 induced not only anti-Aβ antibodies, but also antibodies against Aβ species and amyloidogenic peptides. Importantly, YM3711 vaccination induced reduction of Aβ and Aβ species in model mice.

In this application, the present inventors showed that YM3711 vaccination not only induced anti-Aβ and anti-Aβ species antibodies but also induced Aβ-related antibodies other than anti-Aβ1-42 antibodies. As reported recently (Vasilevko V et al, Neurobiol Dis 2010, 39: 301-310), repeated Aβ peptide vaccination induced antibodies recognizing conformational epitopes especially at later stages. Antibodies induced by YM3711 may possess similar characteristics. Competition assay revealed that YM3711-induced antibodies also contain antibodies directed at linear epitopes of the Aβ molecules, indicating that YM3711 vaccination elicits a wide variety of antibodies against Aβ and Aβ-related molecules.

Further studies were conducted to determine whether anti-IgFc antibody and anti-IL-4 antibody were induced upon YM3711 immunization, there was no induction of these antibodies. The reason is not clear why antibody against repeats of Aβ is induced, whereas no antibody is induced against the IgFc or IL-4 moiety. However, human IgFc and IL-4 molecules are similar to those of monkeys and hence are recognized as self-components by the monkey's body, so that antibodies against these molecules would be difficult to induce. In contrast, Aβ molecules, which are of self origin, abnormally aggregate and hence the body will recognize the aggregate as a foreign substance to cause antibody production.

This finding is important for clinical use of the vaccine in avoiding unwanted immune responses and in enhancing vaccine safety.

Recently, a large number of reports showed that main neurotoxic Aβ species are Aβ dimers and oligomers (reviewed in Haass and Selkoe, Nat Rev Mol Cell Biol 2007; 8: 101-112). Among them, Aβ species that have molecular weight, 48-56 kDa, and exhibit a special structure such as globulomer are reported to be most neurotoxic (Barghorn S et al, J Neurochem 2005, 95: 834-847; Hillen H et al, J Neurosci 2010, 30: 10369-10379; Ma B et al, J Biol Chem 2010, 285: 37102-37110). Therefore, it is essential to reduce such Aβ species to obtain sufficient therapeutic effects. It was clearly demonstrated that YM3711 vaccination reduced not only Aβ but also a variety of Aβ species including that with molecular weight of 56 kDa in model mice. These findings strongly suggest that YM3711 could be able to achieve significant Aβ reduction in patients with Alzheimer's disease.

In summary, vaccination with YM3711 induces a wide variety of antibodies against Aβ and Aβ species and reduces Aβ and Aβ-related deposits. Importantly, YM3711 vaccination did not induce any adverse effects such as hemorrhage and inflammation in the brain. Thus, YM3711 could have potentials to treat Alzheimer's disease.

In view of the foregoing, the vaccines of the present invention were found not only to induce a wide variety of antibodies against various neurotoxic molecules, including predominantly Aβ, in Alzheimer's disease, but also to eliminate Aβ deposition. No DNA vaccine showing such a mechanism of action has been reported in the past.

INDUSTRIAL APPLICABILITY

The present invention provides DNA vaccines for prevention or treatment of Alzheimer's disease. The vaccines of the present invention remarkably suppress Aβ accumulation and hence are useful as pharmaceutical compositions for treatment or prevention of Alzheimer's disease.

SEQUENCE LISTING FREE TEXT

SEQ ID NO: 1: synthetic DNA
SEQ ID NO: 2: synthetic peptide
SEQ ID NO: 3: synthetic DNA
SEQ ID NO: 4: synthetic peptide
SEQ ID NO: 5: synthetic DNA
SEQ ID NO: 6: synthetic peptide
SEQ ID NO: 7: synthetic DNA
SEQ ID NO: 8: synthetic peptide
SEQ ID NO: 9: synthetic DNA
SEQ ID NO: 10: synthetic peptide
SEQ ID NO: 11: synthetic DNA
SEQ ID NO: 12: synthetic peptide
SEQ ID NO: 13: synthetic DNA
SEQ ID NO: 14: synthetic peptide
SEQ ID NO: 15: synthetic DNA
SEQ ID NO: 16: synthetic peptide
SEQ ID NO: 21: synthetic DNA
SEQ ID NO: 22: synthetic DNA
SEQ ID NO: 23: synthetic DNA SEQ ID NO: 24: synthetic DNA
SEQ ID NO: 25: synthetic DNA
SEQ ID NO: 26: synthetic DNA
SEQ ID NO: 27: synthetic DNA
SEQ ID NO: 28: synthetic DNA SEQ ID NO: 29: synthetic DNA
SEQ ID NO: 30: synthetic DNA
SEQ ID NO: 31: synthetic DNA
SEQ ID NO: 34: synthetic DNA
SEQ ID NO: 35: synthetic DNA

The invention claimed is:

1. A recombinant expression vector, which comprises repeats of Amyloid β 1-42 (Aβ1-42) coding sequence, an immunoglobulin Fc (IgFc) coding sequence, a second spacer coding sequence and an interleukin-4 (IL-4) coding sequence in this order, wherein the repeats of the Aβ1-42 coding sequence contain a first spacer coding sequence between the individual Aβ1-42 coding sequences, and the vector is capable of expressing a fusion protein combining repeats of the Aβ1-42 sequence, the IgFc sequence, the second spacer sequence and the IL-4 sequence, and wherein the IgFc coding sequence comprises SEQ ID NO: 32.

2. A DNA vaccine for treatment of Alzheimer's disease or the elimination of brain Aβ, or a pharmaceutical composition for inducing anti-Aβ antibody, which comprises:
the recombinant vector according to claim 1; and
a pharmaceutically acceptable carrier.

3. A method for treating Alzheimer's disease, comprising administrating to a subject having Alzheimer's disease an effective amount of the recombinant vector according to claim 1 to treat the Alzheimer's disease.

4. A method of reducing brain Aβ, comprising administrating to a subject having excess brain Aβ an effective amount of the recombinant vector according to claim 1 to reduce brain Aβ.

5. A method of inducing anti-Aβ antibody, comprising administrating to a subject in need of anti-Aβ antibody an effective amount of the recombinant vector according to claim 1 to induce anti-Aβ antibody.

6. The recombinant expression vector of claim 1, wherein the interleukin-4 coding sequence comprises SEQ ID NO: 17.

7. The recombinant expression vector of claim 1, wherein the fusion protein comprises 2 to 4 Aβ1-42 repeats.

8. A method for treating Alzheimer's disease, comprising administrating to a subject having Alzheimer's disease an effective amount of the recombinant vector according to claim 7 to treat the Alzheimer's disease.

9. A method of reducing brain Aβ, comprising administrating to a subject having excess brain Aβ an effective amount of the recombinant vector according to claim 7 to reduce brain Aβ.

10. A method of inducing anti-Aβ antibody, comprising administrating to a subject in need of anti-Aβ antibody an effective amount of the recombinant vector according to claim 7 to induce anti-Aβ antibody.

11. The recombinant expression vector of claim 1, which further comprises an Ig leader (IgL) coding sequence in an order before the repeats of the Aβ1-42 coding sequence, and wherein the IgL sequence is capable of being expressed in an order before the Aβ1-42 repeats and the IgL sequence is part of the fusion protein.

12. The recombinant expression vector of claim 11, wherein the fusion protein comprises 2 to 4 Aβ1-42 repeats.

13. A recombinant vector, which comprises the nucleotide sequence shown in SEQ ID NO: 28 or 29.

14. A DNA vaccine for treatment of Alzheimer's disease or the elimination of brain Aβ, or a pharmaceutical composition for induction of anti-Aβ antibody, which comprises:
the recombinant vector according to claim 13; and
a pharmaceutically acceptable carrier.

15. A method for treating Alzheimer's disease, comprising administrating to a subject having Alzheimer's disease an effective amount of the recombinant vector according to claim 13 to treat the Alzheimer's disease.

16. A method of reducing brain Aβ, comprising administrating to a subject having excess brain Aβ an effective amount of the recombinant vector according to claim 13 to reduce brain Aβ.

17. A method of inducing anti-Aβ antibody, comprising administrating to a subject in need of anti-Aβ antibody an effective amount of the recombinant vector according to claim 13 to induce anti-Aβ antibody.

* * * * *